US009327092B2

(12) United States Patent
Brambilla

(10) Patent No.: US 9,327,092 B2
(45) Date of Patent: *May 3, 2016

(54) VENTILATION MASK WITH INTEGRATED PILOTED EXHALATION VALVE

(71) Applicant: Breathe Technologies, Inc., Irvine, CA (US)

(72) Inventor: Enrico Brambilla, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 553 days.

This patent is subject to a terminal disclaimer.

(21) Appl. No.: 13/784,561

(22) Filed: Mar. 4, 2013

(65) Prior Publication Data

US 2013/0184602 A1 Jul. 18, 2013

Related U.S. Application Data

(63) Continuation-in-part of application No. 13/411,348, filed on Mar. 2, 2012, now Pat. No. 8,844,533.

(60) Provisional application No. 61/499,950, filed on Jun. 22, 2011, provisional application No. 61/512,750, filed on Jul. 28, 2011.

(51) Int. Cl.
*A61M 11/00* (2006.01)
*A61M 16/06* (2006.01)
(Continued)

(52) U.S. Cl.
CPC ............. *A61M 16/0666* (2013.01); *A61B 5/03* (2013.01); *A61B 5/087* (2013.01); *A61B 5/097* (2013.01);
(Continued)

(58) Field of Classification Search
CPC .......... A61M 16/0666; A61M 16/201; A61M 16/1045; A61M 16/0875; A61M 16/207; A61M 16/0833
USPC ............. 128/207.13, 201.13, 205.24, 207.18, 128/204.18
See application file for complete search history.

(56) References Cited

U.S. PATENT DOCUMENTS

| 8,413 A | 10/1851 | St. John |
|---|---|---|
| 42,346 A | 4/1864 | Ghambeblin |

(Continued)

FOREIGN PATENT DOCUMENTS

| AU | 2003217098 A1 | 12/2003 |
|---|---|---|
| CA | 1315174 C | 3/1993 |

(Continued)

OTHER PUBLICATIONS

Heat and Moisture Exchangers in Artificial Ventilation: An Experimental Study of the Effect of Gas Leakage S. E. Tilling and B. Hayes Br. J. Anaesth. (1987) 59(9): 1181-1188.

(Continued)

*Primary Examiner* — Steven Douglas
(74) *Attorney, Agent, or Firm* — Stetina Brunda Garred & Brucker

(57) ABSTRACT

A mask for achieving positive pressure mechanical ventilation (inclusive of CPAP, ventilator support, critical care ventilation, emergency applications), and a method for a operating a ventilation system including such mask. The mask includes a piloted exhalation valve that is used to achieve the target pressures/flows to the patient. The pilot for the valve may be pneumatic and driven from the gas supply tubing from the ventilator. The pilot may also be a preset pressure derived in the mask, a separate pneumatic line from the ventilator, or an electro-mechanical control. The mask of the present invention may further include a heat and moisture exchanger (HME) which is integrated therein.

20 Claims, 14 Drawing Sheets

(51) Int. Cl.
  *A61M 16/20*  (2006.01)
  *A61M 16/00*  (2006.01)
  *A61B 5/087*  (2006.01)
  *A61B 5/00*   (2006.01)
  *A61B 5/097*  (2006.01)
  *A61B 5/03*   (2006.01)
  *A61M 16/08*  (2006.01)
  *A61M 16/10*  (2006.01)

(52) U.S. Cl.
  CPC .......... *A61B 5/4836* (2013.01); *A61M 16/0066* (2013.01); *A61M 16/0833* (2014.02); *A61M 16/0875* (2013.01); *A61M 16/20* (2013.01); *A61M 16/201* (2014.02); *A61M 16/207* (2014.02); *A61M 16/1045* (2013.01)

(56) References Cited

U.S. PATENT DOCUMENTS

| | | |
|---|---|---|
| 53,694 A | 4/1866 | Smith |
| 53,695 A | 4/1866 | Somes |
| 189,153 A | 4/1877 | Towle et al. |
| 252,515 A | 1/1882 | Ebdshaw |
| 306,346 A | 10/1884 | Pabaf-Javal |
| 321,600 A | 7/1885 | Heckee |
| 416,701 A | 12/1889 | Yocom |
| 430,380 A | 6/1890 | Evarts |
| 432,325 A | 7/1890 | McIntyre |
| 474,434 A | 5/1892 | Banker |
| 516,494 A | 3/1894 | La Veck |
| 539,217 A | 5/1895 | Chapman |
| 546,673 A | 9/1895 | Meyer |
| 694,089 A | 2/1902 | Brewer |
| 3,326,214 A | 6/1967 | McCoy |
| 3,726,275 A | 4/1973 | Jackson et al. |
| 3,802,431 A | 4/1974 | Farr |
| 3,881,482 A | 5/1975 | Lindholm et al. |
| 3,902,486 A | 9/1975 | Guichard |
| 4,062,359 A | 12/1977 | Geaghan |
| 4,121,583 A | 10/1978 | Chen |
| 4,245,633 A | 1/1981 | Erceg |
| 4,266,540 A | 5/1981 | Panzik et al. |
| 4,278,082 A | 7/1981 | Blackmer |
| 4,318,398 A | 3/1982 | Oetjen |
| 4,325,365 A | 4/1982 | Barbuto |
| 4,458,679 A | 7/1984 | Ward |
| 4,535,767 A | 8/1985 | Tiep et al. |
| 4,559,941 A | 12/1985 | Timmons et al. |
| 4,572,177 A | 2/1986 | Tiep et al. |
| 4,620,537 A | 11/1986 | Brown |
| 4,699,139 A | 10/1987 | Marshall |
| 4,739,757 A | 4/1988 | Edwards |
| 4,771,770 A | 9/1988 | Artemenko et al. |
| 4,787,105 A | 11/1988 | Phillips et al. |
| 4,793,343 A | 12/1988 | Cummins et al. |
| 4,836,200 A | 6/1989 | Clark et al. |
| 4,913,140 A | 4/1990 | Orec |
| 4,949,733 A | 8/1990 | Sampson et al. |
| D311,609 S | 10/1990 | Stoneburner |
| 5,018,519 A | 5/1991 | Brown |
| 5,025,805 A | 6/1991 | Nutter |
| 5,062,145 A | 10/1991 | Zwaan et al. |
| 5,065,756 A | 11/1991 | Rapoport |
| 5,072,729 A | 12/1991 | DeVries |
| 5,111,809 A | 5/1992 | Gamble et al. |
| 5,117,820 A | 6/1992 | Robitaille |
| 5,134,995 A | 8/1992 | Gruenke et al. |
| 5,193,534 A | 3/1993 | Peppler |
| 5,245,995 A | 9/1993 | Sullivan et al. |
| 5,284,160 A | 2/1994 | Dryden |
| 5,303,699 A | 4/1994 | Bonassa et al. |
| 5,331,957 A | 7/1994 | Liu |
| 5,353,788 A | 10/1994 | Miles et al. |
| 5,367,604 A | 11/1994 | Murray |
| 5,383,447 A | 1/1995 | Lang |
| 5,400,776 A | 3/1995 | Bartholomew |
| 5,433,192 A | 7/1995 | Ebeling |
| 5,435,298 A | 7/1995 | Anthony |
| 5,445,143 A | 8/1995 | Sims |
| 5,462,048 A | 10/1995 | Lambert et al. |
| 5,492,113 A | 2/1996 | Estes et al. |
| 5,503,146 A | 4/1996 | Froehlich et al. |
| 5,503,147 A | 4/1996 | Bertheau |
| 5,505,768 A | 4/1996 | Altadonna |
| 5,529,060 A | 6/1996 | Salmon et al. |
| 5,537,996 A | 7/1996 | McPhee |
| 5,537,997 A | 7/1996 | Mechlenburg et al. |
| 5,542,416 A | 8/1996 | Chalvignac |
| 5,546,930 A | 8/1996 | Wikefeldt |
| 5,551,419 A | 9/1996 | Froehlich et al. |
| 5,558,084 A | 9/1996 | Daniell et al. |
| 5,586,551 A | 12/1996 | Hilliard |
| 5,588,423 A | 12/1996 | Smith |
| 5,595,173 A | 1/1997 | Dodd |
| 5,598,837 A | 2/1997 | Sirianne et al. |
| 5,598,838 A | 2/1997 | Servidio |
| 5,617,913 A | 4/1997 | DeGregoria et al. |
| 5,640,951 A | 6/1997 | Huddart et al. |
| 5,645,047 A | 7/1997 | Akers |
| 5,645,049 A | 7/1997 | Foley |
| 5,647,344 A | 7/1997 | Turnbull |
| 5,655,522 A | 8/1997 | Mechlenburg et al. |
| 5,666,950 A | 9/1997 | Smith |
| 5,673,687 A | 10/1997 | Dobson et al. |
| 5,685,296 A | 11/1997 | Zdrojkowski et al. |
| 5,694,923 A | 12/1997 | Hete et al. |
| 5,701,891 A | 12/1997 | Groenke |
| 5,704,916 A | 1/1998 | Byrd |
| 5,709,204 A | 1/1998 | Lester |
| 5,730,122 A | 3/1998 | Lurie |
| 5,735,267 A | 4/1998 | Tobia |
| 5,813,399 A | 9/1998 | Isaza et al. |
| 5,836,303 A | 11/1998 | Hurst et al. |
| 5,848,590 A | 12/1998 | Smith |
| 5,853,884 A | 12/1998 | Nichols et al. |
| 5,860,418 A | 1/1999 | Lundberg |
| 5,937,855 A | 8/1999 | Zdrojkowski et al. |
| 5,957,131 A | 9/1999 | Hutchinson et al. |
| 5,964,219 A | 10/1999 | Pekka |
| 6,014,890 A | 1/2000 | Breen |
| 6,017,374 A | 1/2000 | Huxham |
| 6,026,811 A | 2/2000 | Settle |
| 6,050,260 A | 4/2000 | Daniell et al. |
| 6,078,730 A | 6/2000 | Huddart et al. |
| 6,095,135 A | 8/2000 | Clawson et al. |
| 6,116,235 A | 9/2000 | Walters et al. |
| 6,135,432 A | 10/2000 | Hebblewhite et al. |
| 6,165,105 A | 12/2000 | Boutellier et al. |
| 6,201,223 B1 | 3/2001 | Nitta |
| 6,272,933 B1 | 8/2001 | Gradon et al. |
| 6,305,372 B1 | 10/2001 | Servidio |
| 6,308,706 B1 | 10/2001 | Lammers et al. |
| 6,318,366 B1 | 11/2001 | Davenport |
| 6,318,369 B1 | 11/2001 | Gregory |
| 6,332,463 B1 | 12/2001 | Farrugia et al. |
| 6,338,473 B1 | 1/2002 | Hebblewhite et al. |
| 6,349,722 B1 | 2/2002 | Gradon et al. |
| 6,363,930 B1 | 4/2002 | Clawson et al. |
| 6,367,474 B1 | 4/2002 | Berthon-Jones |
| 6,394,084 B1 | 5/2002 | Nitta |
| 6,397,841 B1 | 6/2002 | Kenyon |
| 6,398,197 B1 | 6/2002 | Dickinson |
| 6,425,395 B1 | 7/2002 | Brewer et al. |
| 6,435,178 B1 | 8/2002 | Lin |
| 6,478,026 B1 | 11/2002 | Wood |
| 6,505,624 B1 | 1/2003 | Campbell, Sr. |
| 6,516,798 B1 | 2/2003 | Davies |
| 6,523,538 B1 | 2/2003 | Wikefeldt |
| 6,536,432 B2 | 3/2003 | Truschel |
| 6,536,436 B1 | 3/2003 | McGlothen |
| 6,543,449 B1 | 4/2003 | Woodring et al. |
| 6,550,476 B1 | 4/2003 | Ryder |
| 6,554,260 B1 | 4/2003 | Lipscombe et al. |

(56) References Cited

U.S. PATENT DOCUMENTS

| | | |
|---|---|---|
| 6,557,551 B2 | 5/2003 | Nitta |
| 6,561,193 B1 | 5/2003 | Noble |
| 6,584,972 B2 | 7/2003 | McPhee |
| 6,584,977 B1 | 7/2003 | Serowski |
| 6,595,215 B2 | 7/2003 | Wood |
| 6,598,604 B1 | 7/2003 | Seakins |
| 6,629,531 B2 | 10/2003 | Gleason et al. |
| 6,662,802 B2 | 12/2003 | Smith |
| 6,668,828 B1 | 12/2003 | Figley et al. |
| 6,679,264 B1 | 1/2004 | Deem et al. |
| 6,679,265 B2 | 1/2004 | Strickland et al. |
| 6,694,974 B1 | 2/2004 | George-Gradon et al. |
| 6,733,556 B1 | 5/2004 | Luigi |
| 6,766,800 B2 | 7/2004 | Chu et al. |
| 6,772,758 B2 | 8/2004 | Lambert |
| 6,772,999 B2 | 8/2004 | Lipscombe et al. |
| 6,776,158 B1 | 8/2004 | Anderson et al. |
| 6,802,314 B2 | 10/2004 | McPhee |
| 6,805,120 B1 | 10/2004 | Jeffrey et al. |
| 6,807,966 B2 | 10/2004 | Wright |
| 6,817,361 B2 | 11/2004 | Berthon-Jones |
| 6,851,425 B2 | 2/2005 | Paul et al. |
| 6,863,069 B2 | 3/2005 | Wood |
| 6,886,562 B2 | 5/2005 | Ishizuka |
| 6,899,102 B1 | 5/2005 | McGlothen |
| 6,918,389 B2 | 7/2005 | Seakins et al. |
| 6,921,417 B2 | 7/2005 | Persson |
| 6,923,181 B2 | 8/2005 | Tuck |
| 6,935,337 B2 | 8/2005 | Virr et al. |
| 6,953,354 B2 | 10/2005 | Edirisuriya |
| 6,976,488 B2 | 12/2005 | Halperin |
| 6,986,353 B2 | 1/2006 | Wright |
| 6,990,977 B1 | 1/2006 | Calluaud |
| 6,994,089 B2 | 2/2006 | Wood |
| 6,997,177 B2 | 2/2006 | Wood |
| 7,004,162 B1 | 2/2006 | Foley et al. |
| 7,013,361 B2 | 3/2006 | Liron |
| 7,032,592 B2 | 4/2006 | Castor |
| 7,043,979 B2 | 5/2006 | Smith |
| 7,047,974 B2 | 5/2006 | Strickland et al. |
| 7,051,733 B2 | 5/2006 | Gradon et al. |
| 7,069,928 B1 | 7/2006 | Waldo, Jr. |
| 7,086,399 B2 | 8/2006 | Makinson et al. |
| 7,106,955 B2 | 9/2006 | Thudor et al. |
| 7,111,624 B2 | 9/2006 | Thudor et al. |
| 7,120,354 B2 | 10/2006 | Mackie et al. |
| 7,137,388 B2 | 11/2006 | Virr et al. |
| 7,137,389 B2 | 11/2006 | Berthon-Jones |
| 7,140,367 B2 | 11/2006 | White |
| 7,146,976 B2 | 12/2006 | McKown |
| 7,146,979 B2 | 12/2006 | Seakins et al. |
| 7,188,624 B2 | 3/2007 | Wood |
| 7,192,550 B2 | 3/2007 | Berger et al. |
| 7,225,811 B2 | 6/2007 | Ruiz et al. |
| RE39,724 E | 7/2007 | Gradon et al. |
| 7,237,770 B2 | 7/2007 | Lipscombe et al. |
| 7,263,994 B2 | 9/2007 | Gradon et al. |
| 7,270,128 B2 | 9/2007 | Berthon-Jones |
| 7,306,205 B2 | 12/2007 | Huddart et al. |
| 7,396,995 B2 | 7/2008 | Laurent et al. |
| 7,406,966 B2 | 8/2008 | Wondka |
| 7,428,902 B2 | 9/2008 | Du et al. |
| 7,438,073 B2 | 10/2008 | Delache et al. |
| 7,469,698 B1 | 12/2008 | Childers |
| 7,481,222 B2 | 1/2009 | Reissmann |
| 7,487,774 B2 | 2/2009 | Acker |
| 7,493,902 B2 | 2/2009 | White et al. |
| 7,506,647 B2 | 3/2009 | Worthington |
| 7,525,663 B2 | 4/2009 | Kwok et al. |
| RE40,806 E | 6/2009 | Gradon et al. |
| 7,549,419 B2 | 6/2009 | Carlsen et al. |
| 7,568,482 B2 | 8/2009 | Jaffre et al. |
| 7,588,029 B2 | 9/2009 | Smith et al. |
| 7,594,509 B2 | 9/2009 | Burk |
| 7,614,398 B2 | 11/2009 | Virr et al. |
| 7,616,871 B2 | 11/2009 | Kramer |
| 7,624,731 B2 | 12/2009 | Walstrom |
| 7,634,998 B1 | 12/2009 | Fenley |
| 7,658,189 B2 | 2/2010 | Davidson et al. |
| 7,708,017 B2 | 5/2010 | Davidson et al. |
| 7,717,113 B2 | 5/2010 | Andrieux |
| 7,770,579 B2 | 8/2010 | O'Connor et al. |
| 7,798,148 B2 | 9/2010 | Doshi et al. |
| 7,849,852 B2 | 12/2010 | Bremner et al. |
| 7,856,979 B2 | 12/2010 | Doshi et al. |
| 7,870,857 B2 | 1/2011 | Dhuper et al. |
| 7,913,497 B2 | 3/2011 | Dickerson |
| 7,913,640 B2 | 3/2011 | MacDonald et al. |
| 7,926,485 B2 | 4/2011 | Nguyen et al. |
| 7,942,148 B2 | 5/2011 | Davidson et al. |
| 7,958,891 B2 | 6/2011 | Smith et al. |
| 7,962,018 B2 | 6/2011 | Hunt et al. |
| 7,987,847 B2 | 8/2011 | Wickham et al. |
| 7,987,852 B2 | 8/2011 | Doshi et al. |
| 7,992,564 B2 | 8/2011 | Doshi et al. |
| 7,997,270 B2 | 8/2011 | Meier |
| 8,006,691 B2 | 8/2011 | Kenyon et al. |
| 8,015,971 B2 | 9/2011 | Kwok |
| 8,020,551 B2 | 9/2011 | Virr et al. |
| RE42,843 E | 10/2011 | Strickland et al. |
| 8,028,693 B2 | 10/2011 | Trevor-Wilson et al. |
| 8,037,882 B2 | 10/2011 | Smith et al. |
| 8,042,535 B2 | 10/2011 | Kenyon et al. |
| 8,052,127 B2 | 11/2011 | Nichols et al. |
| 8,061,355 B2 | 11/2011 | Jaffre et al. |
| 8,061,357 B2 | 11/2011 | Pierce et al. |
| 8,069,854 B2 | 12/2011 | Colla et al. |
| 8,313,440 B2 | 11/2012 | Friedman et al. |
| 2002/0083947 A1 | 7/2002 | Seakins |
| 2003/0079748 A1 | 5/2003 | Seakins |
| 2003/0079751 A1 | 5/2003 | Kwok |
| 2004/0035431 A1 | 2/2004 | Wright |
| 2004/0065327 A1 | 4/2004 | Gradon et al. |
| 2004/0211421 A1 | 10/2004 | Blansfield |
| 2005/0011521 A1 | 1/2005 | Sprinkle et al. |
| 2005/0121038 A1 | 6/2005 | Christopher |
| 2005/0126573 A1 | 6/2005 | Jaffre et al. |
| 2007/0056590 A1 | 3/2007 | Wolfson |
| 2007/0062534 A1 | 3/2007 | Fisher et al. |
| 2007/0079826 A1 | 4/2007 | Kramer et al. |
| 2007/0267023 A1 | 11/2007 | Ging et al. |
| 2007/0277825 A1 | 12/2007 | Bordewick et al. |
| 2008/0047560 A1 | 2/2008 | Veliss et al. |
| 2008/0060649 A1 | 3/2008 | Veliss et al. |
| 2008/0066745 A1 | 3/2008 | Janbakhsh et al. |
| 2008/0099013 A1 | 5/2008 | Graham |
| 2008/0105257 A1 | 5/2008 | Klasek et al. |
| 2008/0142015 A1 | 6/2008 | Groll |
| 2008/0156330 A1 | 7/2008 | Smith et al. |
| 2008/0190436 A1 | 8/2008 | Jaffe et al. |
| 2008/0223367 A1 | 9/2008 | Cox et al. |
| 2008/0257343 A1 | 10/2008 | Peterson |
| 2008/0302361 A1 | 12/2008 | Snow et al. |
| 2009/0000620 A1 | 1/2009 | Virr |
| 2009/0044808 A1 | 2/2009 | Guney et al. |
| 2009/0050153 A1 | 2/2009 | Brunner |
| 2009/0065005 A1 | 3/2009 | Ades |
| 2009/0065729 A1 | 3/2009 | Worboys et al. |
| 2009/0095295 A1 | 4/2009 | Wruck et al. |
| 2009/0114221 A1 | 5/2009 | Nagorny |
| 2009/0114229 A1 | 5/2009 | Frater et al. |
| 2009/0133700 A1 | 5/2009 | Martin |
| 2009/0151719 A1 | 6/2009 | Wondka et al. |
| 2009/0151728 A1 | 6/2009 | McConnell et al. |
| 2009/0174092 A1 | 7/2009 | Kwok |
| 2009/0194106 A1 | 8/2009 | Smith et al. |
| 2009/0223514 A1 | 9/2009 | Smith et al. |
| 2009/0229606 A1 | 9/2009 | Tang et al. |
| 2009/0241948 A1 | 10/2009 | Clancy et al. |
| 2009/0247967 A1 | 10/2009 | Delli Paoli, Jr. |
| 2009/0277448 A1 | 11/2009 | Ahlmen et al. |
| 2009/0277452 A1 | 11/2009 | Lubke et al. |
| 2009/0293881 A1 | 12/2009 | Graham |
| 2009/0301478 A1 | 12/2009 | Ohmura et al. |

(56) References Cited

U.S. PATENT DOCUMENTS

| | | |
|---|---|---|
| 2009/0320840 A1 | 12/2009 | Klasek et al. |
| 2010/0018534 A1 | 1/2010 | Veliss et al. |
| 2010/0043796 A1 | 2/2010 | Meynink et al. |
| 2010/0071693 A1 | 3/2010 | Allum et al. |
| 2010/0078017 A1 | 4/2010 | Andrieux et al. |
| 2010/0083965 A1 | 4/2010 | Virr et al. |
| 2010/0095966 A1 | 4/2010 | Dureus |
| 2010/0101575 A1 | 4/2010 | Fedorko et al. |
| 2010/0101584 A1 | 4/2010 | Bledstein et al. |
| 2010/0132717 A1 | 6/2010 | Davidson et al. |
| 2010/0147299 A1 | 6/2010 | Row et al. |
| 2010/0154796 A1 | 6/2010 | Smith et al. |
| 2010/0180895 A1 | 7/2010 | Kwok et al. |
| 2010/0206308 A1 | 8/2010 | Klasek et al. |
| 2010/0206312 A1 | 8/2010 | O'Leary |
| 2010/0236549 A1 | 9/2010 | Selvarajan et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0282247 A1 | 11/2010 | Kadrichu et al. |
| 2011/0017212 A1 | 1/2011 | Kenyon et al. |
| 2011/0023874 A1 | 2/2011 | Bath et al. |
| 2011/0023877 A1 | 2/2011 | Kenyon et al. |
| 2011/0030691 A1 | 2/2011 | Campbell |
| 2011/0067704 A1 | 3/2011 | Kooij et al. |
| 2011/0073111 A1 | 3/2011 | Stone et al. |
| 2011/0094518 A1 | 4/2011 | Cipollone et al. |
| 2011/0120462 A1 | 5/2011 | Tatkov et al. |
| 2011/0126834 A1 | 6/2011 | Winter et al. |
| 2011/0126835 A1 | 6/2011 | Winter et al. |
| 2011/0162647 A1 | 7/2011 | Huby et al. |
| 2011/0203595 A1 | 8/2011 | Hashemieh |
| 2011/0209709 A1 | 9/2011 | Davidson et al. |
| 2011/0214676 A1 | 9/2011 | Allum et al. |
| 2011/0247619 A1 | 10/2011 | Formica et al. |
| 2011/0253136 A1 | 10/2011 | Sweeney et al. |
| 2011/0253147 A1 | 10/2011 | Gusky et al. |
| 2011/0265796 A1 | 11/2011 | Amarasinghe et al. |
| 2011/0283999 A2 | 11/2011 | Smith et al. |
| 2011/0297150 A1 | 12/2011 | Kwok |

FOREIGN PATENT DOCUMENTS

| | | |
|---|---|---|
| CA | 2193906 A1 | 6/1997 |
| CA | 2408983 A1 | 4/2003 |
| CH | 685678 A5 | 9/1995 |
| CN | 1878589 A | 12/2006 |
| CN | 2880043 Y | 3/2007 |
| CN | 101069764 A | 11/2007 |
| CN | 200995037 Y | 12/2007 |
| CN | 201123948 Y | 10/2008 |
| CN | 201161072 Y | 12/2008 |
| CN | 201239409 Y | 5/2009 |
| CN | 201249002 Y | 6/2009 |
| CN | 101474449 A | 7/2009 |
| CN | 201279335 Y | 7/2009 |
| CN | 201356075 Y | 12/2009 |
| CN | 101816466 A | 9/2010 |
| DE | 3829115 A1 | 3/1989 |
| DE | 4011873 A1 | 10/1990 |
| DE | 4434236 A1 | 3/1996 |
| DE | 69211011 T2 | 12/1996 |
| DE | 69724996 T2 | 7/2004 |
| DE | 60213428 T2 | 3/2007 |
| DE | 60031249 T2 | 5/2007 |
| DE | 60215955 T2 | 6/2007 |
| DE | 60213427 T2 | 9/2007 |
| DE | 20122844 U1 | 6/2008 |
| EP | 265163 A3 | 2/1989 |
| EP | 317417 A1 | 1/1992 |
| EP | 504977 A1 | 9/1992 |
| EP | 409402 B1 | 8/1993 |
| EP | 417026 A1 | 7/1994 |
| EP | 588214 B1 | 12/1998 |
| EP | 604399 B1 | 12/1998 |
| EP | 1005878 A2 | 6/2000 |
| EP | 686408 A2 | 8/2000 |
| EP | 1100591 B1 | 11/2004 |
| EP | 1314445 A1 | 9/2005 |
| EP | 1163923 A2 | 11/2005 |
| EP | 1629859 A1 | 3/2006 |
| EP | 1854494 A1 | 11/2007 |
| EP | 1042034 B1 | 2/2008 |
| EP | 1938856 A1 | 7/2008 |
| EP | 2039387 A8 | 11/2009 |
| EP | 2113275 A1 | 11/2009 |
| EP | 2229973 A3 | 11/2010 |
| EP | 2269681 A2 | 1/2011 |
| EP | 2272557 A2 | 1/2011 |
| EP | 2296740 A1 | 3/2011 |
| EP | 2301615 A1 | 3/2011 |
| FR | 2915106 A3 | 10/2008 |
| JP | 10248947 A | 9/1998 |
| JP | 2004215996 A | 8/2004 |
| JP | 2006289093 A | 10/2006 |
| JP | 2008113922 A | 5/2008 |
| JP | 2008136826 A | 6/2008 |
| JP | 2010264183 A | 11/2010 |
| RU | 2336907 C2 | 10/2008 |
| WO | 2008113424 A1 | 9/2008 |
| WO | 2009109005 A1 | 9/2009 |
| WO | 2009118718 A1 | 10/2009 |
| WO | 2009127049 A1 | 10/2009 |
| WO | 2009149284 A1 | 12/2009 |
| WO | 2009149289 A1 | 12/2009 |
| WO | 2009149290 A1 | 12/2009 |
| WO | 2010044034 A1 | 4/2010 |
| WO | 2010044035 A1 | 4/2010 |
| WO | 2010044039 A2 | 4/2010 |
| WO | 2010076704 A1 | 7/2010 |
| WO | 2010096467 A1 | 8/2010 |
| WO | WO2012177562 | 12/2012 |

OTHER PUBLICATIONS

Randomised, Multi-Centre Study of the Usefulness of the Heat and Moisture Exchanger (Provox Hme(®)) in Laryngectomised Patients. Dassonville O, Mérol JC, Bozec A, Swierkosz F, Santini J, Chaës A, Marcy PY, Giacchero P, Chamorey.

The Effect of a Newly Developed Heat and Moisture Exchanger for Pulmonary Rehabilitation of Laryngectomized Patients on the Endotracheal Temperature and Humidity. Scheenstra R, Muller S, Vincent A, Ackerstaff A, Jacobi I, Hilgers F. Respir Care. Jan. 27, 2011.

Endotracheal Temperature and Humidity in Laryngectomized Patients in a Warm and Dry Environment and the Effect of a Heat and Moisture Exchanger. Scheenstra RJ, Muller SH, Hilgers FJ. Head Neck. Oct. 27, 2010.

In Vitro Evaluation of an Active Heat-And-Moisture Exchanger: The Hygrovent Gold. Pelosi P, Severgnini P, Selmo G, Corradini M, Chiaranda M, Novario R, Park GR. Respir Care. Apr. 2010;55(4):460-6.

Short-Term Endotracheal Climate Changes and Clinical Effects of a Heat and Moisture Exchanger With an Integrated Electrostatic Virus and Bacterial Filter Developed for Laryngectomized Individuals. Scheenstra RJ, Muller SH, Vincent A, Ackerstaff AH, Jacobi I, Hilgers FJ.

Humidification and Secretion Volume In Mechanically Ventilated Patients. Solomita M, Palmer LB, Daroowalla F, Liu J, Miller D, LeBlanc DS, Smaldone GC. Respir Care. Oct. 2009;54(10):1329-35.

The Clinical and Microbiological Comparison of the Use of Heated Humidifiers and Heat and Moisture Exchanger Filters With Booster in Mechanically Ventilated Patients]. Nadir Ozi_T, Ozcan Kanat D, O_uzülgen IK, Aydo_du M, Hizel K, Gürsel G.

Pulmonary Rehabilitation After Total Laryngectomy Using a Heat and Moisture Exchanger (Hme)]. Lorenz KJ, Maier H. Laryngorhinootologie. Aug. 2009;88(8):513-22. Epub Jul. 30, 2009.

(56) References Cited

OTHER PUBLICATIONS

Evaluating Humidity Recovery Efficiency of Currently Available Heat and Moisture Exchangers: A Respiratory System Model Study. Lucato JJ, Adams AB, Souza R, Torquato JA, Carvalho CR, Marini JJ.
The Effect of a Heat and Moisture Exchanger (Provox Hme) on Pulmonary Protection After Total Laryngectomy: A Randomized Controlled Study Bie_S, Okla S, van As-Brooks CJ, Ackerstaff AH. Eur Arch Otorhinolaryngol. Mar. 2010;267(3):429-35.
The Influence of a Heat and Moisture Exchanger on Tracheal Climate in a Cold Environment. Zuur JK, Muller SH, Vincent A, Sinaasappel M, de Jongh FH, Hilgers FJ. Med Eng Phys. Sep. 2009;31(7):852-7. Epub May 28, 2009.
Water Content of Delivered Gases During Non-Invasive Ventilation in Healthy Subjects. Lellouche F, Maggiore SM, Lyazidi A, Deye N, TailléS, Brochard L. Intensive Care Med. Jun. 2009;35(6):987-95. Epub Mar. 18, 2009.
Prospective Controlled Study of Microbial Colonization of the Trachea in Tracheotomized and Laryngectomized Patients With Hme (Heat and Moisture Exchanger) Kramp B, Donat M, Dommerich S, Pau HW, Podbielski A. Acta Otolaryngol. Oct. 2009;129(10):1136-44.
Heat and Moisture Exchanger: Importance of Humidification in Anaesthesia and Ventilatory Breathing System. Parmar V. J Indian Med Assoc. Aug. 2008;106(8):533-5, 537.
Tracheostoma Humidifier: Influence on Secretion and Voice of Patients With Total Laryngectomy. Masson AC, Fouquet ML, Gonçalves AJ. Pro Fono. Jul.-Sep. 2008;20(3):183-9.
Comparison of Two Humidification Systems for Long-Term Noninvasive Mechanical Ventilation. Nava S, Cirio S, Fanfulla F, Carlucci A, Navarra A, Negri A, Ceriana P. Eur Respir J. Aug. 2008;32(2):460-4.
Assessment of Tracheal Temperature and Humidity in Laryngectomized Individuals and the Influence of a Heat and Moisture Exchanger on Tracheal Climate Zuur JK, Muller SH, Vincent A, Sinaasappel M, de Jongh FH, Hilgers FJ.
Ventilator-Associated Pneumonia in Adults in Developing Countries: A Systematic Review. Arabi Y, Al-Shirawi N, Memish Z, Anzueto A. Int J Infect Dis. Sep. 2008;12(5):505-12.
The Effect of Heat-Moisture Exchanger and Closed-Circuit Technique on Airway Climate During Desflurane Anesthesia. Lu CC, Ho ST, Liaw WJ, Chen RM, Chen TL, Lin CY. J Anesth. 2008;22(1):7-12. Epub Feb. 27, 2008.
[Humidification Assessment of Four Heat and Moisture Exchanger Filters According to Iso 9360: 2000 Standard]. Lannoy D, Décaudin B, Resibois JP, Barrier F, Wierre L, Horrent S, Batt C, Moulront S, Odou P.
Montreal'S Experience With Cyranose Heat and Moisture Exchanger Use in 15 Laryngectomized Patients. Dupuis P, Guertin L, Rainville MS, Prud'homme DL, Lavigne F. J Otolaryngol. Aug. 2007;36(4):208-12.
Secretion Management in The Mechanically Ventilated Patient. Branson RD. Respir Care. Oct. 2007;52(10):1328-42; discussion 1342-7.
Influence of Heat and Moisture Exchanger Respiratory Load on Transcutaneous Oxygenation in Laryngectomized Individuals: A Randomized Crossover Study. Zuur JK, Muller SH, Sinaasappel M, Hart GA, van Zandwijk N, Hilgers FJ.
Moisturizing and Mechanical Characteristics of a New Counter-Flow Type Heated Humidifier. Schumann S, Stahl CA, Möller K, Priebe HJ, Guttmann J. Br J Anaesth. Apr. 2007;98(4):531-8. Epub Feb. 27, 2007.
Efficacy of a Heat and Moisture Exchanger in Inhalation Anesthesia At Two Different Flow Rates. Yamashita K, Yokoyama T, Abe H, Nishiyama T, Manabe M. J Anesth. 2007;21(1):55-8. Epub Jan. 30, 2007.
Airway Humidification With a Heat and Moisture Exchanger in Mechanically Ventilated Neonates : A Preliminary Evaluation. Fassassi M, Michael F, Thomachot L, Nicaise C, Vialet R, Jammes Y, Lagier P, Martin C.

The Effects of Apparatus Dead Space on P(Aco2) in Patients Receiving Lung-Protective Ventilation. Hinkson CR, Benson MS, Stephens LM, Deem S. Respir Care. Oct. 2006;51(10):1140-4.
Effect of Humidifying Devices on the Measurement of Tidal Volume By Mechanical Ventilators. Fujita Y, Imanaka H, Fujino Y, Takeuchi M, Tomita T, Mashimo T, Nishimura M. J Anesth. 2006;20(3):166-72.
Effect of Heat and Moisture Exchanger (Hme) Positioning on Inspiratory Gas Humidification. Inui D, Oto J, Nishimura M. BMC Pulm Med. Aug. 2006;6:19.
Ventilator-Associated Pneumonia Using a Heated Humidifier or a Heat and Moisture Exchanger: A Randomized Controlled Trial [Isrctn88724583] Lorente L, Lecuona M, Jiménez A, Mora ML, Sierra A. Crit Care. 2006;10(4):R116.
Under-Humidification and Over-Humidification During Moderate Induced Hypothermia With Usual Devices. Lellouche F, Qader S, Taille S, Lyazidi A, Brochard L. Intensive Care Med. Jul. 2006;32(7):1014-21.
[Intensive Care Medicine—Update 2005]. Flohë S, Lendemans S, Schmitz D, Waydhas C. Zentralbl Chir. Jun. 2006;131(3):175-87.
Effect of Ventilation Equipment on Imposed Work of Breathing. French CJ, Bellomo R, Buckmaster J. Crit Care Resusc. Sep. 2001;3(3):148-52.
Double-Heater-Wire Circuits and Heat-And-Moisture Exchangers and the Risk of Ventilator-Associated Pneumonia. Boots RJ, George N, Faoagali JL, Druery J, Dean K, Heller RF. Crit Care Med. Mar. 2006;34(3):687-93.
Influence of Passive Humidification on Respiratory Heat Loss in Tracheotomized Patients. Rozsasi A, Leiacker R, Fischer Y, Keck T. Head Neck. Jul. 2006;28(7):609-13.
Partial Liquid Ventilation: Effects of Closed Breathing Systems, Heat-And-Moisture-Exchangers and Sodalime Absorbers on Perfluorocarbon Evaporation. Wilms CT, Schober P, Kalb R, Loer SA. Eur J Anaesthesiol. Jan. 2006;23(1):31-5.
Bench-To-Bedside Review: Adjuncts to Mechanical Ventilation in Patients With Acute Lung Injury. Rouby JJ, Lu Q. Crit Care. Oct. 5, 2005;9(5):465-71. Epub Jun. 28, 2005.
Prolonged Sedation in the Pediatric Intensive Care Unit May Be Difficult Because of Tolerance, Drug Dependence and Withdrawal, Drug Interactions and Unwanted Drug Effects. We Present Three Patients Sedated With Isoflurane Via the Anesthetic Conserving Dev Sackey PV, Martling CR, Radell PJ. Paediatr Anaesth. Oct. 2005;15(10):879-85.
Comparison of the Bain System and Uniflow Universal Anaesthetic Breathing Systems in Spontaneously Breathing Young Pigs. Almubarak A, Clarke K, Jackson TL. Vet Anaesth Analg. Sep. 2005;32(5):314-21.
Impact of Humidification Systems on Ventilator-Associated Pneumonia: A Randomized Multicenter Trial. Lacherade JC, Auburtin M, Cerf C, Van de Louw A, Soufir L, Rebufat Y, Rezaiguia S, Ricard JD, Lellouche Am J Respir Crit Care Med. Nov. 15, 2005;172(10):1276-82. Epub 2005.
Compliance, Quality of Life and Quantitative Voice Quality Aspects of Hands-Free Speech. Op de Coul BM, Ackerstaff AH, van As-Brooks CJ, van den Hoogen FJ, Meeuwis CA, Manni JJ, Hilgers FJ. Acta Otolaryngol. Jun. 2005;125(6):629-37.
Volume-Guaranteed Pressure-Support Ventilation Facing Acute Changes in Ventilatory Demand. Jaber S, Delay JM, Matecki S, Sebbane M, Eledjam JJ, Brochard.
Inhalational Anaesthetics in the Icu: Theory and Practice of Inhalational Sedation in the Icu, Economics, Risk-Benefit. Meiser A, Laubenthal H. Best Pract Res Olin Anaesthesiol. Sep. 2005;19(3):523-38.
Tracheal Climate in Laryngectomees After Use of a Heat and Moisture Exchanger. Keck T, Dürr J, Leiacker R, Rettinger G, Rozsasi A. Laryngoscope. Mar. 2005;115(3):534-7.
Automatic Speaking Valve in Speech Rehabilitation for Laryngectomized Patients. Tervonen H, Bäck L, Juvas A, Räsänen P, Mäkitie AA, Sintonen H, Roine RP, Vilkman E, Aaltonen LM. Eur Arch Otorhinolaryngol. Oct. 2005;262(10):816-20. Epub Mar. 2005.
Periodically Changing Ventilator Circuits Is Not Necessary to Prevent Ventilator-Associated Pneumonia When a Heat and Moisture

(56) References Cited

OTHER PUBLICATIONS

Exchanger Is Used. Lorente L, Lecuona M, Galván R, Ramos MJ, Mora ML, Sierra A. Infect Control Hosp Epidemiol. Dec. 2004;25(12):1077-82.

Inhalation Rewarming From Hypothermia: An Evaluation in -20 Degrees C Simulated Field Conditions. Mekjavi_IB, Eiken O. Aviat Space Environ Med. May 1995;66(5):424-9.

Mechanical Ventilation With Heated Humidifiers or Heat and Moisture Exchangers: Effects on Patient Colonization and Incidence of Nosocomial Pneumonia. Dreyfuss D, Djedaïni K, Gros I, Mier L, Le Bourdellés G, Cohen Y, Estagnasië P, Coste F, Boussougant.

Preservation of Humidity and Heat of Respiratory Gases in Patients With a Minute Ventilation Greater Than 10 L/Min. Martin C, Papazian L, Perrin G, Saux P, Gouin F. Crit Care Med. Nov. 1994;22(11):1871-6.

Bair Hugger Forced-Air Warming Maintains Normothermia More Effectively Than Thermo-Lite Insulation. Borms SF, Engelen SL, Himpe DG, Suy MR, Theunissen WJ. J Clin Anesth. Jul.-Aug. 1994;6(4):303-7.

Improvements in Respiratory and Psychosocial Functioning Following Total Laryngectomy by the Use of a Heat and Moisture Exchanger Ackerstaff AH, Hilgers FJ, Aaronson NK, Balm AJ, van Zandwijk N. Ann Otol Rhinol Laryngol. Nov. 1993;102(11):878-83.

Oesophageal Thermal Tube for Intraoperative Hypothermia in Liver Transplantation. Steib A, Beller JP, von Bandel M, Beck F, Chabrol JL, Otteni JC. Acta Anaesthesiol Scand. Feb. 1993;37(2):199-202.

Performance of a Hydrophobic Heat and Moisture Exchanger At Different Ambient Temperatures. Croci M, Elena A, Solca M. Intensive Care Med. 1993;19(6):351-2.

An Active Heat and Moisture Exchanger. Kapadia F, Shelly MP, Anthony JM, Park GR. Br J Anaesth. Dec. 1992;69(6):640-2.

Effects of Surgical Site and Inspired Gas Warming Devices on Body Temperature During Lower Abdominal and Thoracic Surgery. Harioka T, Sone T, Nomura K, Kakuyama M. J Anesth. Oct. 1992;6(4):467-73.

Use of a Heat and Moisture Exchanger During Long-Term Mechanical Ventilation. Sottiaux T. Chest. Sep. 1992;102(3):979-80.

Heat and Moisture Exchangers With Bacterial Filters: A Laboratory Evaluation. Mebius C. Acta Anaesthesiol Scand. Aug. 1992;36(6):572-6.

[Are Humidity Filters Necessary in the Inspired Air in the Breathing Circuit? A New In Vivo Method of Measuring Humidity in the Air Breathed] Kohler P, Rimek A, Albrecht M, Frankenberger H, Mertins W, van Ackern K.

[Is the Lithium Chloride-Coated Heat and Moisture Exchanger a Danger for Patients?]. Rathgeber J, Zielmann S, Kietzmann D, Züchner K, Warnecke G. Anaesthesist. Apr. 1992;41(4):204-7.

Disablement of a Ventilator Disconnect Alarm by a Heat and Moisture Exchanger. Milligan KA. Anaesthesia. Mar. 1992;47(3):279.

Comparison of Hydrophobic Heat and Moisture Exchangers With Heated Humidifier During Prolonged Mechanical Ventilation. Roustan JP, Kienlen J, Aubas P, Aubas S, du Cailar J. Intensive Care Med. 1992;18(2):97-100.

Do Heated Humidifiers and Heat and Moisture Exchangers Prevent Temperature Drop During Lower Abdominal Surgery? Goldberg ME, Epstein R, Rosenblum F, Larijani GE, Marr A, Lessin J, Torjman M, Seltzer J.

Effect of a Passive Heat and Moisture Exchanger on Esophageal Temperature in Tumor-Bearing Dogs During.Whole-Body Hyperthermia Meyer RE, Page RL, Thrall DE. Am J Vet Res. Oct. 1991;52(10):1688-91.

Heat and Moisture Exchanger Vs Heated Humidifier During Long-Term Mechanical Ventilation. A Prospective Randomized Study. Misset B, Escudier B, Rivara D, Leclercq B, Nitenberg G. Chest. Jul. 1991;100(1):160-3.

[Treatment of Primary and Secondary Therapy Failure in Patients With Sleep Apnea Treated With Nasal Cpap]. Becker H, Fett I, Nees E, Peter JH, von Wichert P. Pneumologie. May 1991;45 Suppl 1:301-5.

Mucociliary Transport With and Without the Use of a Heat and Moisture Exchanger. An Animal Study. The importance to mucociliary transport (MCT) and the condition of the mucus of using a heat and Acta Anaesthesiol Scand. May 1991;35(4):297-301.

The Influence of a Heat and Moisture Exchanger (Hme) on the Respiratory Symptoms After Total Laryngectomy. Hilgers FJ, Aaronson NK, Ackerstaff AH, Schouwenburg PF, van Zandwikj N.

The Use of an Artificial Nose (Hme: Heat-Moisture Exchanger) In Controlled Ventilation]. Sottiaux T. Rev Med Liege. Apr. 1991;46(4):204-12.

Assessment of a Hygroscopic Heat and Moisture Exchanger for Paediatric Use. Wilkinson KA, Cranston A, Hatch DJ, Fletcher ME. Assessment of a hygroscopic heat and moisture exch . . . [Anaesthesia. 1991]—PubMed.

[Changes in Ventilation During Use of Heat and Humidity Exchangers]. Croci M, Corrado F, Sibilla E, Tiby A, Vercesi G, Proietti D, Vannucci A. Minerva Anestesiol. Jan.-Feb. 1991;57(1-2):13-6.

[Physical and Psychosocial Sequelae of Total Larynx Extirpation and the Use of a Heat and Moisture Exchanger]. Ackerstaff AH, Hilgers FJ, Aaronson NK, Schouwenburg PF, van Zandwijk N.

[Experimental Evaluation of a Prototype of Absolute Antibacterial Filter As a Moisture and Heat Exchanger]. Elena A, Solca M, Croci M, Noto A. Minerva Anestesiol. Oct. 1990;56(10):1253-4.

[Anesthetic Management of a Patient With Sjögren's Syndrome and Pulmonary Fibrosis]. Takahashi S, Ogasawara H, Tsubo T, Ishihara H, Matsuki A. Masui. Oct. 1990;39(10):1393-6.

Heat and Moisture Exchangers and the Body Temperature: A Peroperative Study. Eckerbom B, Lindholm CE. Acta Anaesthesiol Scand. Oct. 1990;34(7):538-42.

Maintenance of Body Temperature in Elderly Patients Who Have Joint Replacement Surgery. A Comparison Between the Heat and Moisture Exchanger and Heated Humidifier Yam PC, Carli F. Anaesthesia. Jul. 1990;45(7):563-5.

Complications Related to the Use of a Heat and Moisture Exchanger. Prasad KK, Chen L. Anesthesiology. May 1990;72(5):958.

153 Passive Warming of Airway Gases (Artificial Nose) Improves Accuracy of Esophageal Temperature Monitoring. Siegel MN, Gravenstein N. J Clin Monit. Apr. 1990;6(2):89-92.

Heat and Moisture Exchangers and Vaporizing Humidifiers in the Intensive Care Unit. Martin C, Perrin G, Gevaudan MJ, Saux P, Gouin F. Chest. Jan. 1990;97(1):144-9.

Bacterial Contamination and Frequency of Changing Ventilator Circuitry. Cadwallader HL, Bradley CR, Ayliffe GA J Hosp Infect. Jan. 1990;15(1):65-72.

Passive or Active Inspired Gas Humidification Increases Thermal Steady-State Temperatures in Anesthetized Infants. Bissonnette B, Sessler DI. Anesth Analg. Dec. 1989;69(6):783-7.

A Dangerous Defect in a Heat and Moisture Exchanger. Prados W. Anesthesiology. Nov. 1989;71(5):804.

Tracheal Tube Biofilm As a Source of Bacterial Colonization of the Lung. Inglis TJ, Millar MR, Jones JG, Robinson DA. J Clin Microbiol. Sep. 1989;27(9):2014-8.

Passive and Active Inspired Gas Humidification in Infants and Children. Bissonnette B, Sessler DI, LaFlamme P Anesthesiology. Sep. 1989;71(3):350-4.

Failure of a Heat and Moisture Exchanger As a Cause of Disconnection During Anaesthesia. Bengtsson M, Johnson A. Acta Anaesthesiol Scand. Aug. 1989;33(6):522-3.

Intraoperative Temperature Monitoring Sites in Infants and Children and the Effect of Inspired Gas Warming on Esophageal Temperature Bissonnette B, Sessler DI, LaFlamme P. Anesth Analg. Aug. 1989;69(2):192-6.

Physiological Effects of a Mouth-Borne Heat Exchanger During Heavy Exercise in a Cold Environment. Eiken O, Kaiser P, Holmér I, Baer R. Ergonomics. Jun. 1989;32(6):645-53.

Study of Humidification Potential of a Heat and Moisture Exchanger in Tracheotomized Dogs. Myer CM 3rd, McDonald JS, Hubbell RN, Stith J. Ann Otol Rhinol Laryngol. May-Jun. 1988;97(3 Pt 1):322-5.

Endotracheal Tube Occlusion Associated With the Use of Heat and Moisture Exchangers in the Intensive Care Unit. Cohen IL, Weinberg PF, Fein IA, Rowinski GS. Crit Care Med. Mar. 1988;16(3):277-9.

The Heat and Moisture Exchanger Does Not Preserve Body Temperature or Reduce Recovery Time in Outpatients Undergoing Sur-

(56) References Cited

OTHER PUBLICATIONS gery and Anesthesia. Goldberg ME, Jan R, Gregg CE, Berko R, Marr AT, Larijani GE. Anesthesiology. Jan. 1988;68(1):122-3.
Effectiveness of a Heat and Moisture Exchanger in Preventing Hyperpnoea Induced Bronchoconstriction in Subjects With Asthma. Gravelyn TR, Capper M, Eschenbacher WL. Thorax. Nov. 1987;42(11):877-80.
An Evaluation of Six Disposable Heat and Moisture Exchangers. Turtle MJ, Ilsley AH, Rutten AJ, Runciman WB. Anaesth Intensive Care. Aug. 1987;15(3):317-22.
Contamination Control in Long-Term Ventilation. A Clinical Study Using a Heat-and Moisture-Exchanging Filter. Gallagher J, Strangeways JE, Allt-Graham J. Anaesthesia. May 1987;42(5):476-81.
Effects of a Heat and Moisture Exchanger on Carbon Dioxide Equilibrium During Mechanical Ventilation With the Bain Circuit. Romano E, Gullo A, Vacri A, Bonifacio R, Caristi D. Eur J Anaesthesiol. May 1987;4(3):183-6.
The Heat and Moisture Exchanger in Post-Tracheotomy Care. Myer CM 3rd. Otolaryngol Head Neck Surg. Feb. 1987;96(2):209-10.
Moistening of Inspired Air During Respirator Treatment. Comparison Between the Water-Bath Evaporator and Hygroscopic Moisture Heat Exchanger]. Kirkegaard L, Andersen BN, Jensen S. Ugeskr Laeger. Jan. 12, 1987;149(3):152-5.
Portable Lung Ventilators: The Potential Risk From Bacterial Colonisation. Shelly MP, Park GR, Warren RE, Whetstone RJ. Intensive Care Med. 1986;12(4):328-31.
PCT Search Report and Written Opinion for PCT/US14/20418, issued Jun. 5, 2014, 11 Pages.
The Effects of Two Kinds of Mask (With or Without Exhaust Valve) on Clothing Microclimates Inside the Mask in Participants Wearing Protective Clothing for Spraying Pesticides Hayashi C, Tokura H. Int Arch Occup Environ Health. Jan. 2004;77(1):73-8. Epub Aug. 30, 2003.
Evaluation on Masks With Exhaust Valves and With Exhaust Holes From Physiological and Subjective Responses Guo YP, Yi L, Tokura H, Wong TK, Chung JW, Gohel MD, Leung PH, Newton E. J Physiol Anthropol. Mar. 2008;27(2):93-102.
Effect of a Nonrebreathing Exhalation Valve on Long-Term Nasal Ventilation Using a Bilevel Device Hill NS, Carlisle C, Kramer NR. Chest. Jul. 2002;122(1):84-91.
Facial or Nasal Mask Pressure Support Ventilation in Managing Acute Exacerbation of Chronic Respiratory Failure in Chronic Obstructive Pulmonary Diseases Chen RC. Zhonghua Jie He He Hu Xi Za Zhi. Oct. 1992;15(5):285-7, 319.
Sleep and Neuromuscular Disease: Bilevel Positive Airway Pressure by Nasal Mask As a Treatment for Sleep Disordered Breathing in Patients With Neuromuscular Disease Guilleminault C, Philip P, Robinson A. J Neurol Neurosurg Psychiatry. Aug. 1998;65(2):225-32.
Nocturnal Assisted Ventilation Using Bilevel Positive Airway Pressure: The Effect of Expiratory Positive Airway Pressure Elliott MW, Simonds AK. Eur Respir J. Mar. 1995;8(3):436-40.
Effect of Nasal Valve Dilation on Effective Cpap Level in Obstructive Sleep Apnea Schönhofer B, Kerl J, Suchi S, Köhler D, Franklin KA. Respir Med. Sep. 2003;97(9):1001-5.
Continuous Positive Airway Pressure: New Generations Roux FJ, Hilbert J. Clin Chest Med. Jun. 2003;24(2):315-42.
A Sleep Laboratory Evaluation of an Automatic Positive Airway Pressure System for Treatment of Obstructive Sleep Apnea Behbehani K, Yen FC, Lucas EA, Burk JR. Sleep. Aug. 1, 1998;21(5):485-91.
CPAP Via Nasal Mask: A Treatment for Occlusive Sleep Apnea Sanders MH, Moore SE, Eveslage J. Chest. Jan. 1983;83(1):144-5.
CPAP Therapy Via Oronasal Mask for Obstructive Sleep Apnea Sanders MH, Kern NB, Stiller RA, Strollo PJ Jr, Martin TJ, Atwood CW Jr. Chest. Sep. 1994;106(3):774-9.

Nasal Continuous Positive Airway Pressure and Noninvasive Positive Ventilation in the Treatment of Sleep Apnea/Hypopnea Syndrome Ohi M, Tachibana N, Taniguchi M. Nippon Rinsho. Aug. 2000;58(8):1675-9.
The Nasal Valve: A Rhinomanometric Evaluation of Maximum Nasal Inspiratory Flow and Pressure Curves Santiago-Diez de Bonilla J, McCaffrey TV, Kern EB. Ann Otol Rhinol Laryngol. May-Jun. 1986;95(3 Pt 1):229-32.
The Four Components of the Nasal Valve Cole P Am J Rhinol. Mar.-Apr. 2003;17(2):107-10.
Oral Continuous Positive Airway Pressure for Sleep Apnea: Effectiveness, Patient Preference, and Adherence Beecroft J, Zanon S, Lukic D, Hanly P. Chest. Dec. 2003;124(6):2200-8.
Oral Appliance Therapy for Obstructive Sleep Apnea Ng A, Gotsopoulos H, Darendeliler AM, Cistulli PA. Treat Respir Med. 2005;4(6):409-22.
Potential Rebreathing After Continuous Positive Airway Pressure Failure During Sleep Farré R, Montserrat JM, Ballester E, Navajas D. Chest. Jan. 2002;121(1):196-200.
Continuous Positive Airway Pressure Therapy Improves Cardiovascular Autonomic Function for Persons With Sleep-Disordered Breathing Maser RE, Lenhard MJ, Rizzo AA, Vasile AA. Chest. Jan. 2008;133(1):86-91. Epub Oct. 20, 2007.
Analysis of Expiratory Pressure Reduction (C-Flex method) During CPAP Therapy Rühle KH, Domanski U, Happel A, Nilius G. Pneumologie. Feb. 2007;61(2):86-9.
Efficacy and Patient Satisfaction With Autoadjusting CPAP With Variable Expiratory Pressure Vs Standard CPAP: A Two-Night Randomized Crossover Trial Mulgrew AT, Cheema R, Fleetham J, Ryan CF, Ayas NT. Sleep Breath. Mar. 2007;11(1):31-7.
Nasal CPAP Therapy of Obstructive Sleep Apnea Syndrome With Expiratory Pressure Reduction: A Prospective Randomized Study of Acceptance of Treatment During Therapy Initiation Ficker JH, Müller D, Wiest G, Lehnert G, Dertinger SH, Katalinic A, Hahn EG. Pneumologie. Jun. 1997;51(6):586-91.
Dynamics of Pressure and Flow Curves of Various Expiratory Pressure Valves Raschke F, Fischer J. Med Klin (Munich). Apr. 28, 1997;92 Suppl 1:82-4.
Continuous Positive Airway Pressure (CPAP)—Does the Equipment Live Up to Its Name? Christensen EF, Nørregaard OF, Anker-Møller E, Spangsberg NL, Petersen KD, Schønemann NK. Ugeskr Laeger. May 25, 1992;154(22):1568-71.
Jet Flow-Regulated Expiratory Resistance to Maintain Constant CPAP During the Entire Respiratory Phase Nishimura M, Takezawa J, Imanaka H, Taenaka N, Yoshiya I. Chest. Apr. 1989;95(4):876-80.
Effects of Expiratory Flow Resistance on Inspiratory Work of Breathing Banner MJ, Downs JB, Kirby RR, Smith RA, Boysen PG, Lampotang S. Chest. Apr. 1988;93(4):795-9.
Augmented Spontaneous Breathing Hachenberg T. Anaesthesist. Sep. 1996;45(9):839-55.
Quantitative Comparison of Ventilator-Induced Work During Simulated CPAP in Eight Demand-Flow Valve Ventilators Nishimura M, Imanaka H, Taenaka N, Yoshiya I, Takezawa J. Masui. Aug. 1989;38(8):1017-29.
N95 Respirator Surgical Mask with Exhalation Valve NA NA.
Exhalation Pressure Relief Defined NA NA.
MV2000 Ventilator NA NA.
Swivel CPAP Exhalation Valve NA NA.
ComfortSelect NA NA.
Sleep Apnea Pillow CPAP Nasal Pillow & Mask Device Pillow NA NA.
A Proximal System for Positive End-Expiratory Pressure (PEEP) and Continuous Positive Airway Pressure (CPAP) Dupuis YG, Vergilio GC, Spoerel WE. Can Anaesth Soc J. Jul. 1979;26(4):331-4.
Flexicare NA NA.
Critical Care Transport NA Critical Care Transport by University of Maryland, American Academy of Orthopaedic Surgeons, Chapter 6, p. 174.
Comfort Classic NA NA.
Respironics ComfortSelect Cpap Mask Small/Wide NA NA.
Porto2Vent NA NA.
Infant Ventilator NA NA.

(56) References Cited

OTHER PUBLICATIONS

The Biomedical Engineering Handbook NA The Biomedical Engineering Handbook, Mechanical Ventilation, p. 82-85.
Positive End-Expiratory Pressure Devices NA NA.
FullLife NA NA.
TBird Legacy NA NA.
Ventilator NA NA.
Muski NA NA.
Martindale NA NA.
Mestel NA NA.
Circadiance NA NA.
Position of Exhalation Port and Mask Design Affect Co2 Rebreathing During Noninvasive Positive Pressure Ventilation Schettino GP, Chatmongkolchart S, Hess DR, Kacmarek RM. Crit Care Med. Aug. 2003;31(8):2178-82.
Mechanical Ventilation of the Surgical Patient Thomas W Shields General Thoracic Surgery, Chapter 42, p. 585.
A Randomized Study of Out-Of-Hospital Continuous Positive Airway Pressure for Acute Cardiogenic Pulmonary Oedema: Physiological and Clinical Effects Plaisance P, Pirracchio R, Berton C, Vicaut E, Payen D. Eur Heart J. Dec. 2007;28(23):2895-901. Epub Oct. 29, 2007.
ComfortFusion NA NA.
Active Exhalation Valve Control: Evaluation of Its Performance in Expiratory Resistance and Pressure Release John Newhart CRT; Chi-Yuan Chuang NA.
Evita 2 Intensive Care Ventilator NA.
Long-Term Compliance of Laryngectomized Patients With a Specialized Pulmonary Rehabilitation Device: Provox Stormfilter. Ackerstaff AH, Hilgers FJ, Balm AJ, Tan IB. Laryngoscope. Feb. 1998;108(2):257-60.
Airway Humidification in Mechanically Ventilated Neonates and Infants: A Comparative Study of a Heat and Moisture Exchanger Vs. A Heated Humidifier Using a New Fast-Response Capacitive Humidity Sensor Schiffmann H, Rathgeber J, Singer D, Harms K, Bolli A, Züchner K.
Clinical Utility of Hygroscopic Heat and Moisture Exchangers in Intensive Care Patients. Boots RJ, Howe S, George N, Harris FM, Faoagali J. Crit Care Med. Oct. 1997;25(10):1707-12.
Correlation Between Simple Clinical Parameters and The In Vitro Humidification Characteristics of Filter Heat and Moisture Exchangers. Groupe De Travail Sur Les Respirateurs. Beydon L, Tong D, Jackson N, Dreyfuss D. Chest. Sep. 1997;112(3):739-44.
Prevention of Patient Bacterial Contamination of Anaesthesia-Circle-Systems: A Clinical Study of the Contamination Risk and Performance of Different Heat and Moisture Exchangers With Electret Filter (Hmef). Rathgeber J, Kietzmann D, Mergeryan H, Hub R, Züchner K.
Unfavorable Mechanical Effects of Heat and Moisture Exchangers in Ventilated Patients. Iotti GA, Olivei MC, Palo A, Galbusera C, Veronesi R, Comelli A, Brunner JX, Braschi A. Intensive Care Med. Apr. 1997;23(4):399-405.
Acute Intraoperative Endotracheal Tube Obstruction Associated With a Heat and Moisture Exchanger in an Infant. Casta A, Houck CS. Anesth Analg. Apr. 1997;84(4):939-40.
Safety of Combined Heat and Moisture Exchanger Filters in Long-Term Mechanical Ventilation. Hurni JM, Feihl F, Lazor R, Leuenberger P, Perret C. Chest. Mar. 1997;111(3):686-91.
Patient Ventilator Interfaces: Practical Aspects in the Chronic Situation. Clini E. Monaldi Arch Chest Dis. Feb. 1997;52(1):76-9.
The Effect of a Heat and Moisture Exchanger on Humidity in a Low-Flow Anaesthesia System. Henriksson BA, Sundling J, Hellman.
Anaesthesia. Feb. 1997;52(2):144-9 108 [Artificial Humidification of Inspired Gas—Status of Knowledge and Technique]. Henze D, Menzel M, Radke J. Anaesthesiol Reanim. 1997;22(6):153-8. 109

The Benefit of Using a Heat and Moisture Exchanger During Short Operations in Young Children. Monrigal JP, Granry JC. Paediatr Anaesth. 1997;7(4):295-300.
Remarks on the Work of J. Rathgeber Et Al. Respiratory Gas Acclimatization With an Efficient Hme (Heat and Moisture Exchanger)—An Effective and Cost Saving Alternative to Active Humidifying of the Ventilated Patient. Anaesthesist (1996) 45: 518-525 Thäle H, Hares W. Anaesthesist. Dec. 1996;45(12):1270-2.
Gradual Reduction of Endotracheal Tube Diameter During Mechanical Ventilation Via Different Humidification Devices. Villafane MC, Cinnella G, Lofaso F, Isabey D, Hart A, Lemaire F, Brochard L.
The Effect of Convection Warming During Abdominal Surgery on the Early Postoperative Heat Balance]. Kaudasch G, Schempp P, Skierski P, Turner E. Anaesthesist. Nov. 1996;45(11):1075-81.
A New Heat and Moisture Exchanger With Speech Valve (Provox Stomafilter). Hilgers FJ, Ackerstaff AH, Balm AJ, Gregor RT. Clin Otolaryngol Allied Sci. Oct. 1996;21(5):414-8.
[The Effect of a Heat and Moisture Exchanger (Hme) on Bronchial Mucus Transport in a Closed Inhalation Anesthesia System]. Konrad F, Mezödy M, Goertz A, Marx T, Georgieff M. Anaesthesist. Sep. 1996;45(9):802-6.
Failure of Ventilation in an Infant Due to Increased Resistance of a Disposable Heat and Moisture Exchanger. Barnes SD, Normoyle DA. Anesth Analg. Jul. 1996;83(1):193.
[Air Conditioning With a High-Performance Hme (Heat and Moisture Exchanger)—An Effective and Economical Alternative to Active Humidifiers in Ventilated Patients. A Prospective and Randomized Clinical Study]. Rathgeber J, Henze D, Züchner K. Anaesthesist. Jun. 1996;45(6):518-25.
Monitoring Body-Core Temperature From the Trachea: Comparison Between Pulmonary Artery, Tympanic, Esophageal, and Rectal Temperatures. Hayes JK, Collette DJ, Peters JL, Smith KW. J Clin Monit. May 1996;12(3):261-9.
Control of Body Temperature During Abdominal Aortic Surgery. Gregorini P, Cangini D. Acta Anaesthesiol Scand. Feb. 1996;40(2):187-90.
[Microbiological Studies of a Nasal Positive Pressure Respirator With and Without a Humidifier System]. Hetzel J, Herb S, Hetzel M, Rusteberg T, Kleiser G, Weber J, Kochs M, Hombach V. Wien Med Wochenschr. 1996;146(13-14):354-6.
Heat and Moisture Exchangers As a Treatment Option in the Post-Operative Rehabilitation of Laryngectomized Patients. Ackerstaff AH, Hilgers FJ, Aaronson NK, De Boer MF, Meeuwis CA, Knegt PP, Spoelstra HA, Van.
Shivering and Rewarming After Cardiac Surgery: Comparison of Ventilator Circuits With Humidifier and Heated Wires to Heat and Moisture Exchangers. McEvoy MT, Carey TJ. Am J Crit Care. Jul. 1995;4(4):293-9.
A Hazardous Modification of a Heat and Moisture Exchanger. Ferguson AJ, Orr DA. Anaesthesia. May 1995;50(5):479.
Mechanical Ventilation With Heated Humidifiers or Heat and Moisture Exchangers: Effects on Patient Colonization and Incidence of Nosocomial Pneumonia. Dreyfuss D, Djedaïni K, Gros I, Mier L, Le Bourdellés G, Cohen Y, Estagnasié P, Coste F, Boussougant.
Effect of a Passive Heat and Moisture Exchanger on Esophageal Temperature in Tumor-Bearing Dogs During Whole-Body Hyperthermia Meyer RE, Page RL, Thrall DE. Am J Vet Res. Oct. 1991;52(10):1688-91.
[The Use of an Artificial Nose (Hme: Heat-Moisture Exchanger) in Controlled Ventilation]. Sottiaux T. Rev Med Liege. Apr. 1991;46(4):204-12.
Assessment of a Hygroscopic Heat and Moisture Exchanger for Paediatric Use. Wilkinson KA, Cranston A, Hatch DJ, Fletcher ME. Assessment of a hygroscopic heat and moisture exch . . . [Anaesthesia. 1991—PubMed result.
Physical and Psychosocial Sequelae of Total Larynx Extirpation and the Use of a Heat and Moisture Exchanger]. Ackerstaff AH, Hilgers FJ, Aaronson NK, Schouwenburg PF, van Zandwijk N.
Extended European Search Report mailed May 28, 2015 for European Patent Application No. EP 12 80 2913.

VENTILATION MASK WITH INTEGRATED PILOTED EXHALATION VALVE

CROSS-REFERENCE TO RELATED APPLICATIONS

The present application is a continuation-in-part of U.S. application Ser. No. 13/411,348 entitled VENTILATION MASK WITH INTEGRATED PILOTED EXHALATION VALVE filed Mar. 2, 2012, which claims priority to U.S. Provisional Patent Application Ser. No. 61/499,950 entitled VENTILATION MASK WITH INTEGRATED PILOTED EXHALATION VALVE filed Jun. 22, 2011, and U.S. Provisional Patent Application Ser. No. 61/512,750 entitled VENTILATION MASK WITH INTEGRATED PILOTED EXHALATION VALVE AND METHOD OF VENTILATING A PATIENT USING THE SAME filed Jul. 28, 2011, the disclosures of which are incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates to systems and methods for controlling delivery of a pressurized flow of breathable gas to a patient and, more particularly, to a ventilation mask such as a full face mask, nasal mask, nasal prongs mask or nasal pillows mask for use in critical care ventilation, respiratory insufficiency or OSA (obstructive sleep apnea) with CPAP (Continuous Positive Airway Pressure) therapy and incorporating a piloted exhalation valve inside the mask.

2. Description of the Related Art

As is known in the medical arts, mechanical ventilators comprise medical devices that either perform or supplement breathing for patients. Early ventilators, such as the "iron lung", created negative pressure around the patient's chest to cause a flow of ambient air through the patient's nose and/or mouth into their lungs. However, the vast majority of contemporary ventilators instead use positive pressure to deliver gas to the patient's lungs via a patient circuit between the ventilator and the patient. The patient circuit typically consists of one or two large bore tubes (e.g., from 22 mm ID for adults to 8 mm ID for pediatric) that interface to the ventilator on one end, and a patient mask on the other end. Most often, the patient mask is not provided as part of the ventilator system, and a wide variety of patient masks can be used with any ventilator. The interfaces between the ventilator, patient circuit and patient masks are standardized as generic conical connectors, the size and shape of which are specified by regulatory bodies (e.g., ISO 5356-1 or similar standards).

Current ventilators are designed to support either "vented" or "leak" circuits, or "non-vented" or "non-leak" circuits. In vented circuits, the mask or patient interface is provided with an intentional leak, usually in the form of a plurality of vent openings. Ventilators using this configuration are most typically used for less acute clinical requirements, such as the treatment of obstructive sleep apnea or respiratory insufficiency. In non-vented circuits, the patient interface is usually not provided with vent openings. Non-vented circuits can have single limb or dual limb patient circuits, and an exhalation valve. Ventilators using non-vented patient circuits are most typically used for critical care applications.

Vented patient circuits are used only to carry gas flow from the ventilator to the patient and patient mask, and require a patient mask with vent openings. When utilizing vented circuits, the patient inspires fresh gas from the patient circuit, and expires $CO_2$-enriched gas, which is purged from the system through the vent openings in the mask. This constant purging of flow through vent openings in the mask when using single-limb circuits provides several disadvantages: 1) it requires the ventilator to provide significantly more flow than the patient requires, adding cost/complexity to the ventilator and requiring larger tubing; 2) the constant flow through the vent openings creates and conducts noise, which has proven to be a significant detriment to patients with sleep apnea that are trying to sleep while wearing the mask; 3) the additional flow coming into proximity of the patient's nose and then exiting the system often causes dryness in the patient, which often drives the need for adding humidification to the system; and 4) patient-expired $CO_2$ flows partially out of the vent holes in the mask and partially into the patient circuit tubing, requiring a minimum flow through the tubing at all times in order to flush the $CO_2$ and minimize the rebreathing of exhaled $CO_2$. To address the problem of undesirable flow of patient-expired $CO_2$ back into the patient circuit tubing, currently known CPAP systems typically have a minimum-required pressure of 4 cm $H_2O$ whenever the patient is wearing the mask, which often produces significant discomfort, claustrophobia and/or feeling of suffocation to early CPAP users and leads to a high (approximately 50%) non-compliance rate with CPAP therapy.

When utilizing non-vented dual limb circuits, the patient inspires fresh gas from one limb (the "inspiratory limb") of the patient circuit and expires $CO_2$-enriched gas from the second limb (the "expiratory limb") of the patient circuit. Both limbs of the dual limb patient circuit are connected together in a "Y" proximal to the patient to allow a single conical connection to the patient mask. When utilizing non-vented single limb circuits, an expiratory valve is placed along the circuit, usually proximal to the patient. During the inhalation phase, the exhalation valve is closed to the ambient and the patient inspires fresh gas from the single limb of the patient circuit. During the exhalation phase, the patient expires $CO_2$-enriched gas from the exhalation valve that is open to ambient. The single limb and exhalation valve are usually connected to each other and to the patient mask with conical connections.

In the patient circuits described above, the ventilator pressurizes the gas to be delivered to the patient inside the ventilator to the intended patient pressure, and then delivers that pressure to the patient through the patient circuit. Very small pressure drops develop through the patient circuit, typically around 1 cm $H_2O$, due to gas flow though the small amount of resistance created by the tubing. Some ventilators compensate for this small pressure drop either by mathematical algorithms, or by sensing the tubing pressure more proximal to the patient.

Ventilators that utilize a dual limb patient circuit typically include an exhalation valve at the end of the expiratory limb proximal to the ventilator, while ventilators that utilize a single limb, non-vented patient circuit typically include an exhalation valve at the end of the single limb proximal to the patient as indicated above. Exhalation valves can have fixed or adjustable PEEP (positive expiratory end pressure), typically in single limb configurations, or can be controlled by the ventilator. The ventilator controls the exhalation valve, closes it during inspiration, and opens it during exhalation. Less sophisticated ventilators have binary control of the exhalation valve, in that they can control it to be either open or closed.

More sophisticated ventilators are able to control the exhalation valve in an analog fashion, allowing them to control the pressure within the patient circuit by incrementally opening or closing the valve. Valves that support this incremental control are referred to as active exhalation valves. In existing ventilation systems, active exhalation valves are most typically implemented physically within the ventilator, and the remaining few ventilation systems with active exhalation valves locate the active exhalation valve within the patient circuit proximal to the patient. Active exhalation valves inside ventilators are typically actuated via an electromagnetic coil in the valve, whereas active exhalation valves in the patient circuit are typically pneumatically piloted from the ventilator through a separate pressure source such a secondary blower, or through a proportional valve modulating the pressure delivered by the main pressure source.

BRIEF SUMMARY OF THE INVENTION

In accordance with the present invention, there is provided a mask (e.g., a nasal pillows mask) for achieving positive pressure mechanical ventilation (inclusive of CPAP, ventilatory support, critical care ventilation, emergency applications), and a method for a operating a ventilation system including such mask. The mask preferably includes a pressure sensing modality proximal to the patient connection. Such pressure sensing modality may be a pneumatic port with tubing that allows transmission of the patient pressure back to the ventilator for measurement, or may include a transducer within the mask. The pressure sensing port is used in the system to allow pressure sensing for achieving and/or monitoring the therapeutic pressures. Alternately or additionally, the mask may include a flow sensing modality located therewithin for achieving and/or monitoring the therapeutic flows.

The mask of the present invention also includes a piloted exhalation valve that is used to achieve the target pressures/flows to the patient. In the preferred embodiment, the pilot for the valve is pneumatic and driven from the gas supply tubing from the ventilator. The pilot can also be a preset pressure derived in the mask, a separate pneumatic line from the ventilator, or an electro-mechanical control. In accordance with the present invention, the valve is preferably implemented with a diaphragm.

One of the primary benefits attendant to including the valve inside the mask is that it provides a path for patient-expired $CO_2$ to exit the system without the need for a dual-limb patient circuit, and without the disadvantages associated with a single-limb patient circuit, such as high functional dead space. For instance, in applications treating patients with sleep apnea, having the valve inside the mask allows patients to wear the mask while the treatment pressure is turned off without risk of re-breathing excessive $CO_2$.

Another benefit for having the valve inside the mask is that it allows for a significant reduction in the required flow generated by the ventilator for ventilating the patient since a continuous vented flow for $CO_2$ washout is not required. Lower flow in turn allows for the tubing size to be significantly smaller (e.g., 2-9 mm ID) compared to conventional ventilators (22 mm ID for adults; 8 mm ID for pediatric). However, this configuration requires higher pressures than the patient's therapeutic pressure to be delivered by the ventilator. In this regard, pressure from the ventilator is significantly higher than the patient's therapeutic pressure, though the total pneumatic power delivered is still smaller than that delivered by a low pressure, high flow ventilator used in conjunction with a vented patient circuit and interface. One obvious benefit of smaller tubing is that it provides less bulk for patient and/or caregivers to manage. For today's smallest ventilators, the bulk of the tubing is as significant as the bulk of the ventilator. Another benefit of the smaller tubing is that is allows for more convenient ways of affixing the mask to the patient. For instance, the tubing can go around the patient's ears to hold the mask to the face, instead of requiring straps (typically called "headgear") to affix the mask to the face. Along these lines, the discomfort, complication, and non-discrete look of the headgear is another significant factor leading to the high non-compliance rate for CPAP therapy. Another benefit to the smaller tubing is that the mask can become smaller because it does not need to interface with the large tubing. Indeed, large masks are another significant factor leading to the high non-compliance rate for CPAP therapy since, in addition to being non-discrete, they often cause claustrophobia. Yet another benefit is that smaller tubing more conveniently routed substantially reduces what is typically referred to as "tube drag" which is the force that the tube applies to the mask, displacing it from the patient's face. This force has to be counterbalanced by headgear tension, and the mask movements must be mitigated with cushion designs that have great compliance. The reduction in tube drag in accordance with the present invention allows for minimal headgear design (virtually none), reduced headgear tension for better patient comfort, and reduced cushion compliance that results in a smaller, more discrete cushion.

The mask of the present invention may further include a heat and moisture exchanger (HME) which is integrated therein. The HME can fully or at least partially replace a humidifier (cold or heated pass-over; active or passive) which may otherwise be included in the ventilation system employing the use of the mask. The HME is positioned within the mask so as to be able to intercept the flow delivered from a flow generator to the patient in order to humidify it, and further to intercept the exhaled flow of the patient in order to capture humidity and heat for the next breath. The HME can also be used as a structural member of the mask, adding a cushioning effect and simplifying the design of the cushion thereof.

The present invention is best understood by reference to the following detailed description when read in conjunction with the accompanying drawings.

BRIEF DESCRIPTION OF THE DRAWINGS

These, as well as other features of the present invention, will become more apparent upon reference to the drawings wherein.

Common reference numerals are used throughout the drawings and detailed description to indicate like elements.

DETAILED DESCRIPTION OF THE INVENTION

Figure 1:
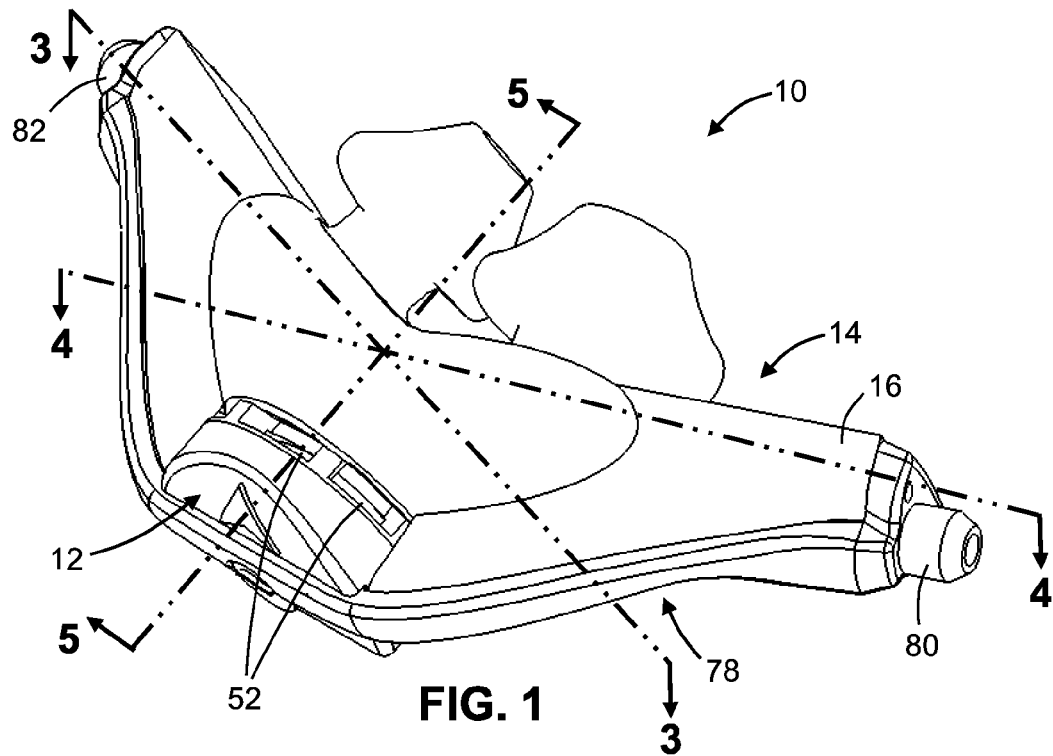
FIG. 1 is top perspective view of a nasal pillows mask constructed in accordance with one embodiment of the present invention and including an integrated diaphragm-based piloted exhalation valve.

Referring now to the drawings wherein the showings are for purposes of illustrating various embodiments of the present invention only, and not for purposes of limiting the same, FIGS. 1-4 depict a ventilation mask 10 (e.g., a nasal pillows mask) constructed in accordance with the present invention. Though the mask 10 is depicted as a nasal pillows mask, those skilled in the art will recognize that other ventilation masks are contemplated herein, such as nasal prongs masks, nasal masks, fill face masks and oronasal masks. As such, for purposes of this application, the term mask and/or ventilation mask is intended to encompass all such mask structures. The mask 10 includes an integrated, diaphragm-implemented, piloted exhalation valve 12, the structural and functional attributes of which will be described in more detail below.

Figure 2:
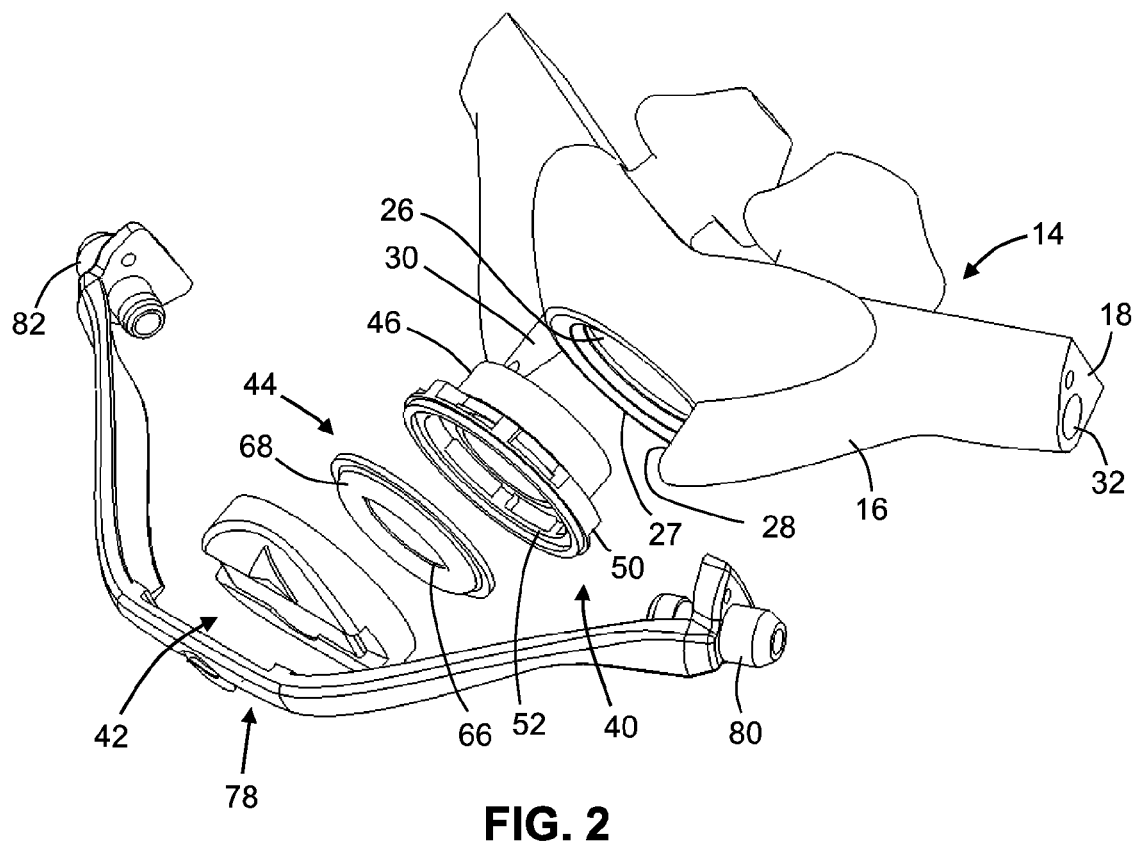
FIG. 2 is an exploded view of the nasal pillows mask shown in FIG. 1.
Figure 3:
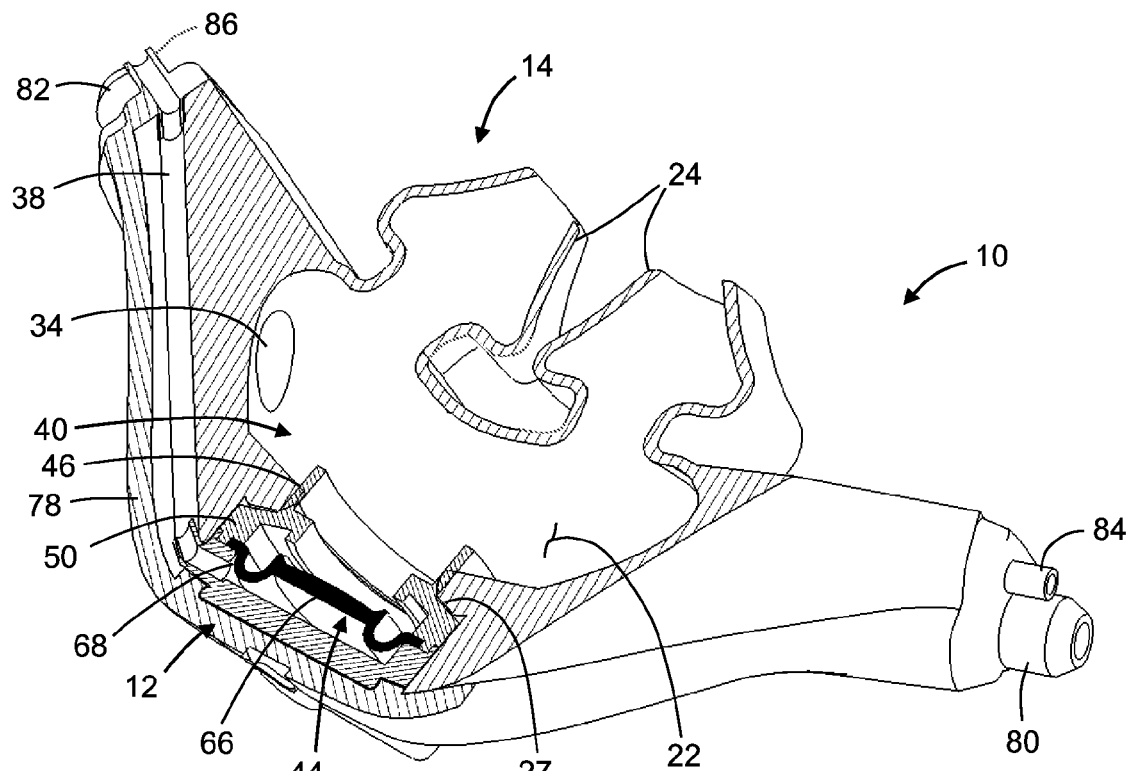
FIG. 3 is a partial cross-sectional view of the nasal pillows mask shown in FIG. 1 taken along lines 3-3 thereof, and depicting the valve pilot lumen extending through the cushion of the mask.
Figure 4:
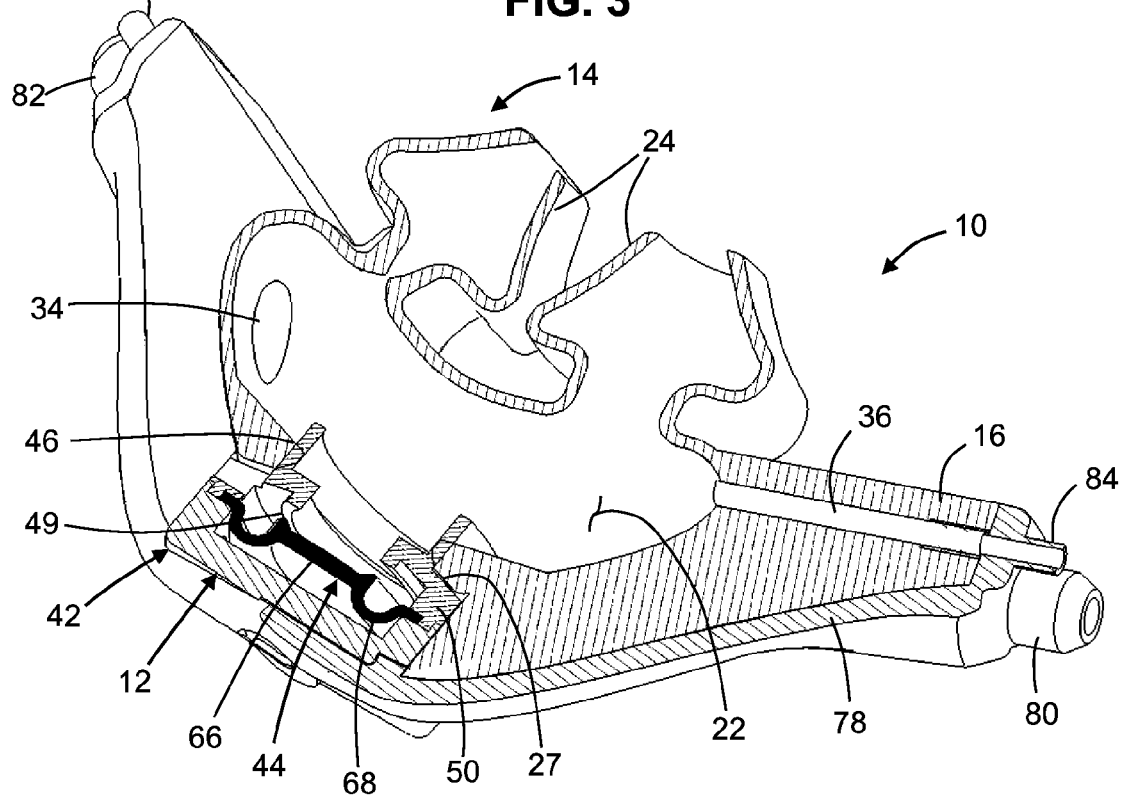
FIG. 4 is a partial cross-sectional view of the nasal pillows mask shown in FIG. 1 taken along lines 4-4 thereof, and depicting the pressure sensing lumen extending through the cushion of the mask.

As shown in FIGS. 1-5, the mask 10 comprises a housing or cushion 14. The cushion 14, which is preferably fabricated from a silicone elastomer having a Shore A hardness in the range of from about 20 to 60 and preferably about 40, is formed as a single, unitary component, and is shown individually in FIG. 6. The cushion 14 includes a main body portion 16 which defines a first outer end surface 18 and an opposed second outer end surface 20. The main body portion 16 further defines an interior fluid chamber 22 which is of a prescribed volume. In addition to the main body portion 16, the cushion 14 includes an identically configured pair of hollow pillow portions 24 which protrude from the main body portion 16 in a common direction and in a prescribed spatial relationship relative to each other. More particularly, in the cushion 14, the spacing between the pillow portions 24 is selected to facilitate the general alignment thereof with the nostrils of an adult patient when the mask 10 is worn by such patient. As seen in FIGS. 3 and 4, each of the pillow portions 24 fluidly communicates with the fluid chamber 22.

As shown in FIG. 2, the main body portion 16 of the cushion 14 includes an enlarged, circularly configured valve opening 26 which is in direct fluid communication with the fluid chamber 22. The valve opening 26 is positioned in generally opposed relation to the pillow portions 24 of the cushion 14, and is circumscribed by an annular valve seat 27 also defined by the main body portion 16. As also shown in FIG. 2, the main body portion 16 further defines opposed first and second inner end surfaces 28, 30 which protrude outwardly from the periphery of the valve opening 26, and are diametrically opposed relative thereto so as to be spaced by an interval of approximately 180°. The valve opening 26, valve seat 27, and first and second inner end surfaces 28, 30 are adapted to accommodate the exhalation valve 12 of the mask 10 in a manner which will be described in more detail below.

Figure 5:
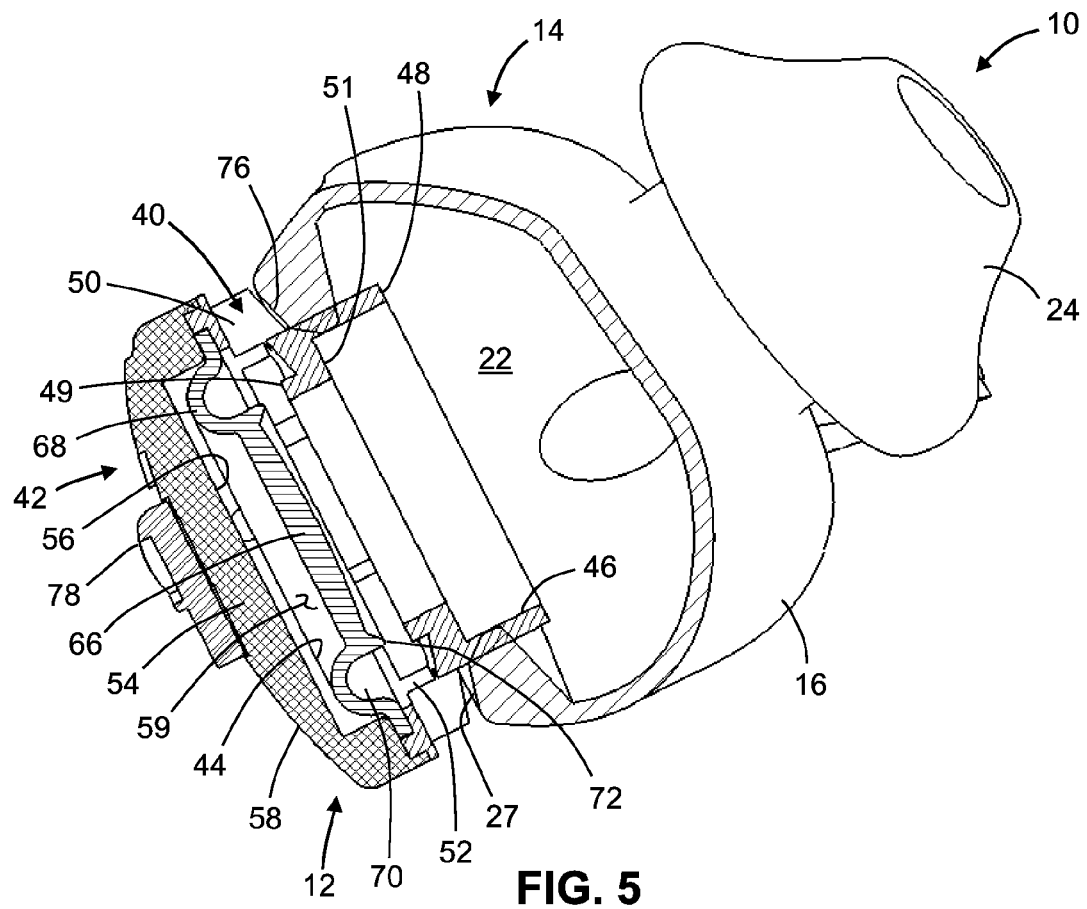
FIG. 5 is a cross-sectional view of the nasal pillows mask shown in FIG. 1 taken along lines 5-5 thereof.
Figure 6:
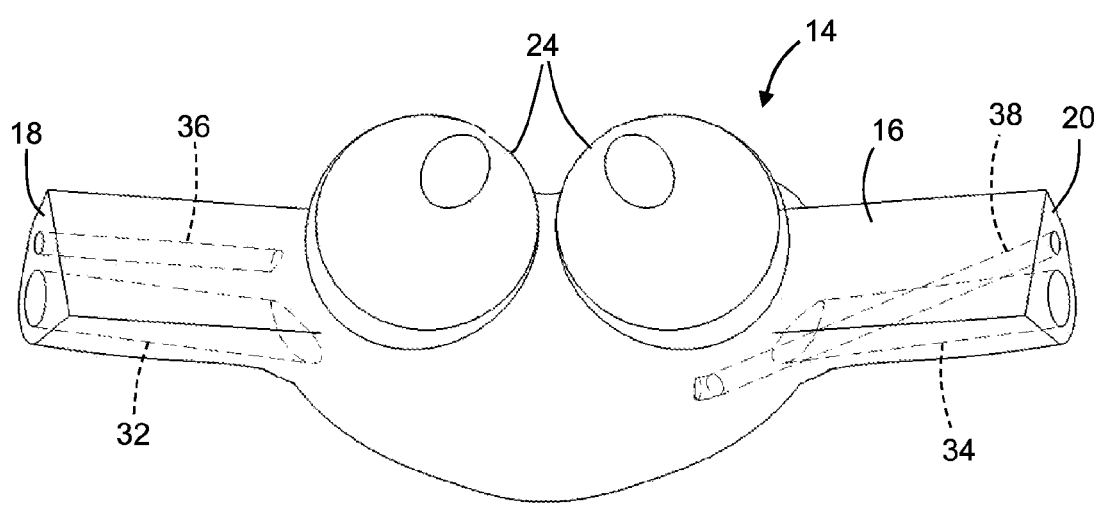
FIG. 6 is a top perspective view of cushion of the nasal pillows mask shown in FIG. 1.

As shown FIGS. 3-6, the main body portion 16 of the cushion 14 further defines first and second gas delivery lumens 32, 34 which extend from respective ones of the first and second outer end surfaces 18, 20 into fluid communication with the fluid chamber 22. Additionally, a pressure sensing lumen 36 defined by the main body portion extends from the first outer end surface 18 into fluid communication with the fluid chamber 22. The main body portion 16 further defines a valve pilot lumen 38 which extends between the second outer end surface 20 and the second inner end surface 30. The use of the first and second gas delivery lumens 32, 34, the pressure sensing lumen 36, and the valve pilot lumen 38 will also be discussed in more detail below. Those of ordinary skill in the art will recognize that the gas delivery lumens 32, 34, may be substituted with a single gas delivery lumen and/or positioned within the cushion 14 in orientations other than those depicted in FIG. 6. For example, the gas delivery lumen(s) of the cushion 14 may be positioned frontally, pointing upwardly, pointing downwardly, etc. rather than extending laterally as shown in FIG. 6.

Referring now to FIGS. 2-5 and 7-9, the exhalation valve 12 of the mask 10 is made of three (3) parts or components, and more particularly a seat member 40, a cap member 42, and a diaphragm 44 which is operatively captured between the seat and cap members 40, 42. The seat and cap members 40, 42 are each preferably fabricated from a plastic material, with the diaphragm 44 preferably being fabricated from an elastomer having a Shore A hardness in the range of from about 20-40.

Figure 7:
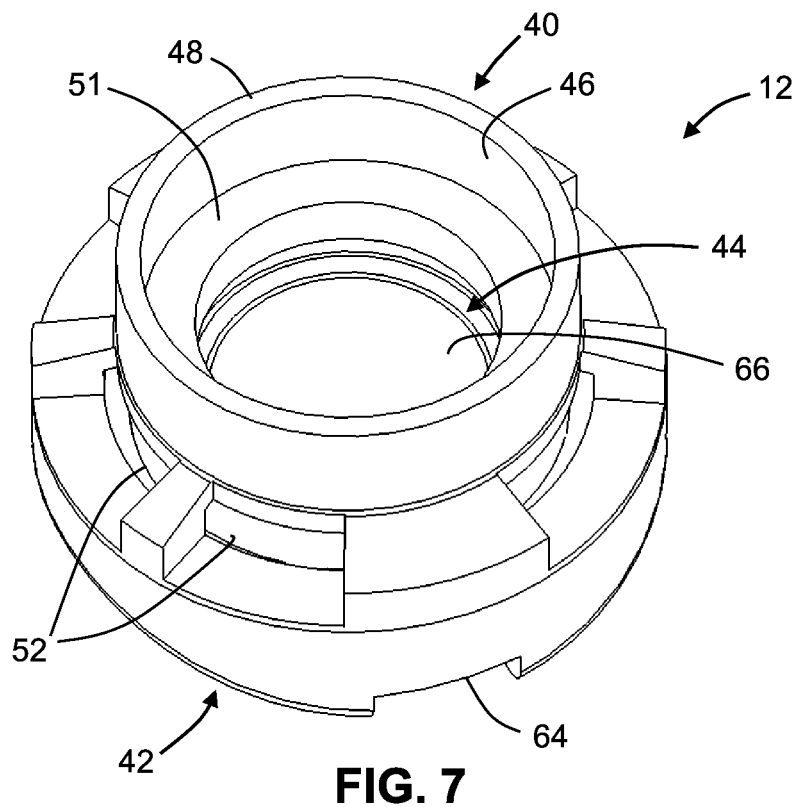
FIG. 7 is a top perspective view of exhalation valve of the nasal pillows mask shown in FIG. 1.
Figure 9:
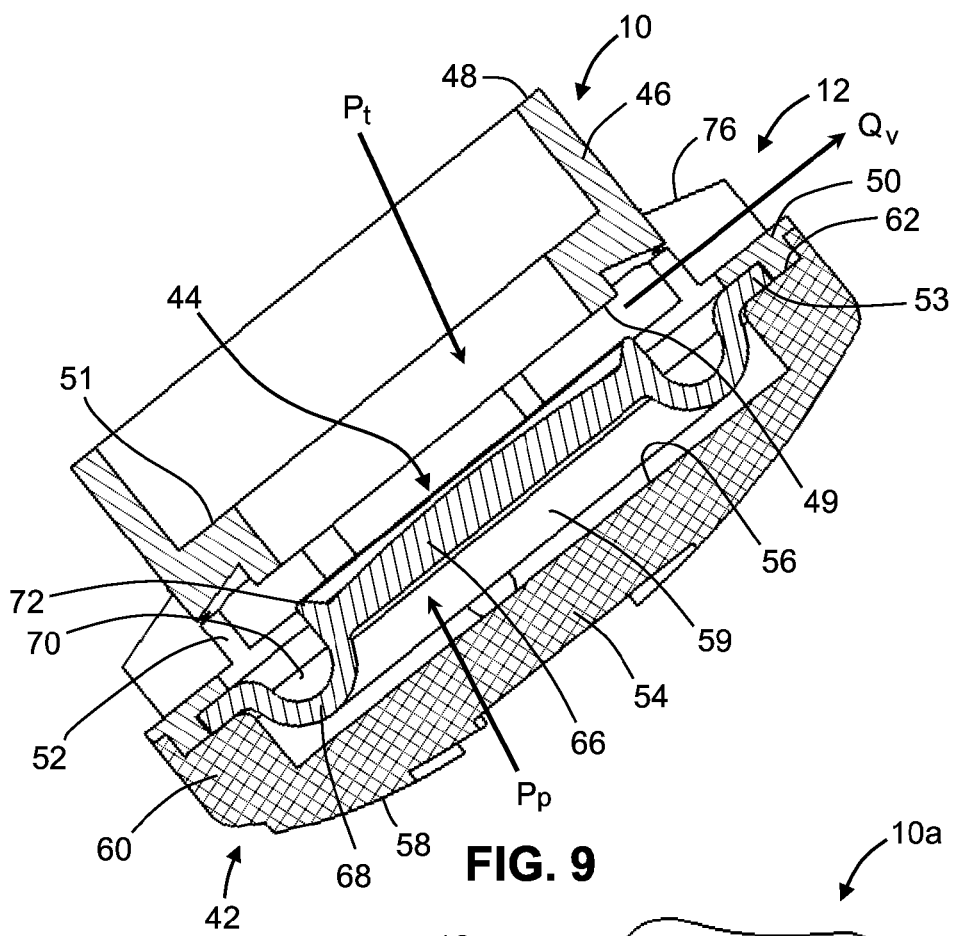
FIG. 9 is a cross-sectional view of exhalation valve shown in FIGS. 7 and 8.

As is most easily seen in FIGS. 2, 7 and 9, the seat member 40 includes a tubular, generally cylindrical wall portion 46 which defines a distal, annular outer rim 48 and an opposed annular inner seating surface 49. As shown in FIG. 9, the diameter of the outer rim 48 exceeds that of the seating surface 49. Along these lines, the inner surface of the wall portion 46 is not of a uniform inner diameter, but rather is segregated into first and second inner surface sections which are of differing inner diameters, and separated by an annular shoulder 51. In addition to the wall portion 46, the seat member 40 includes an annular flange portion 50 which protrudes radially from that end of the wall portion 46 opposite the outer rim 48. As shown in FIGS. 2 and 7, the flange portion 50 includes a plurality of exhaust vents 52 which are located about the periphery thereof in a prescribed arrangement and spacing relative to each other. Additionally, as is apparent from FIG. 9, the seat member 40 is formed such that each of the exhaust vents 52 normally fluidly communicates with the bore or fluid conduit defined by the wall portion 46.

Figure 8:
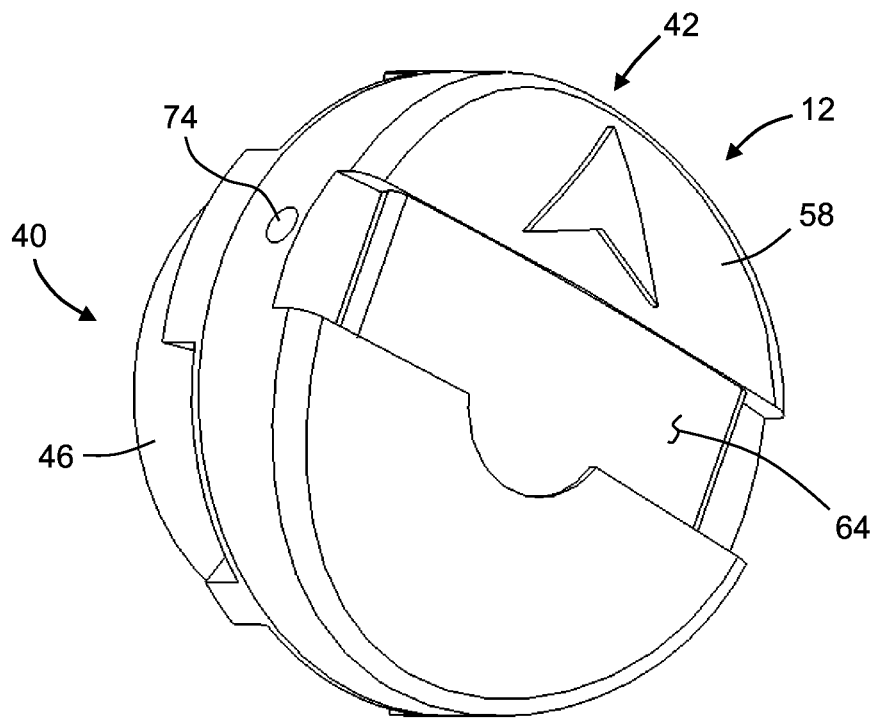
FIG. 8 is a bottom perspective view of exhalation valve shown in FIG. 7.

The cap member 42 of the exhaust valve 12 comprises a circularly configured base portion 54 which defines an inner surface 56 and an opposed outer surface 58. In addition to the base portion 54, the cap member 42 includes an annular flange portion 60 which circumvents and protrudes generally perpendicularly relative to the inner surface 56 of the base portion 60. The flange portion 60 defines a distal annular shoulder 62. As shown in FIG. 9, the shoulder 62 and inner surface 56 extend along respective ones of a spaced, generally parallel pair of planes. Further, as shown in FIG. 8, formed in the outer surface 58 of the base portion 54 is an elongate groove 64 which extends diametrically across the outer surface 58. The use of the groove 64 will be described in more detail below. The seat and cap members 40, 42, when attached to each other in the fully assembled exhalation valve 12, collectively define an interior valve chamber 59 of the exhalation valve 12. More particularly, such valve chamber 59 is generally located between the inner surface 56 defined by the base portion 54 of the cap member 42 and the seating surface 49 defined by the wall portion 46 of the seat member 40.

The diaphragm 44 of the exhalation valve 12, which resides within the valve chamber 59, has a circularly configured, central body portion 66, and a peripheral flange portion 68 which is integrally connected to and circumvents the body portion 66. The body portion 66 includes an annular lip 72 which circumvents and protrudes upwardly from one side or face thereof. The flange portion 68 includes an arcuately contoured primary region and a distal region which protrudes radially from the primary region. As such, the primary region of the flange portion 68 extends between the distal region thereof and the body portion 66, and defines a continuous, generally concave channel 70.

In the exhalation valve 12, the flange portion 68 of the diaphragm 44 is operatively captured between the flange portions 50, 60 of the seat and cap members 40, 42. More particularly, the annular distal region of the flange portion 68 is compressed (and thus captured) between the shoulder 62 defined by the flange portion 60 of the cap member 42, and a complimentary annular shoulder 53 which is defined by the flange portion 50 of the seat member 40 proximate the exhaust vents 52. The orientation of the diaphragm 44 within the valve chamber 59 when captured between the seat and cap members 40, 42 is such that the channel 70 defined by the arcuately contoured primary region of the flange portion 68 is directed toward or faces the seating surface 49 defined by the wall portion 46 of the seat member 40.

The diaphragm 44 (and hence the exhalation valve 12) is selectively moveable between an open position (shown in FIGS. 3-5 and 9) and a closed position. When in its normal, open position, the diaphragm 44 is in a relaxed, unbiased state. Importantly, in either of its open or closed positions, the diaphragm 44 is not normally seated directly against the inner surface 56 defined by the base portion 54 of the cap member 42. Rather, a gap is normally maintained between the body portion 66 of the diaphragm 44 and the inner surface 56 of the base portion 54. The width of such gap when the diaphragm 44 is in its open position is generally equal to the fixed distance separating the inner surface 56 of the base portion 54 from the shoulder 62 of the flange portion 60. Further, when the diaphragm 44 is in its open position, the body portion 66, and in particular the lip 72 protruding therefrom, is itself disposed in spaced relation to the seating surface 49 defined by the wall portion 46 of the seat member 40. As such, when the diaphragm 44 is in its open position, fluid is able to freely pass through the fluid conduit defined by the wall portion 46, between the seating surface 49 and diaphragm 44, and through the exhaust vents 52 to ambient air. As shown in FIGS. 3, 8 and 9, the flange portion 60 of the cap member 42 is further provided with a pilot port 74 which extends therethrough and, in the fully assembled exhalation valve 12, fluidly communicates with that portion of the valve chamber 59 disposed between the body portion 66 of the diaphragm 44 and the inner surface 56 of the base portion 54. The use of the pilot port 74 will also be described in more detail below.

As will be discussed in more detail below, in the exhalation valve 12, the diaphragm 44 is resiliently deformable from its open position (to which it may be normally biased) to its closed position. An important feature of the present invention is that the diaphragm 44 is normally biased to its open position which provides a failsafe to allow a patient to inhale ambient air through the exhalation valve 12 and exhale ambient air therethrough (via the exhaust vents 52) during any ventilator malfunction or when the mask 10 is worn without the therapy being delivered by the ventilator. When the diaphragm 44 is moved or actuated to its closed position, the lip 72 of the body portion 66 is firmly seated against the seating surface 49 defined by the wall portion 46 of the seat member 40. The seating of the lip 72 against the seating surface 49 effectively blocks fluid communication between the fluid conduit defined by the wall portion 46 and the valve chamber 59 (and hence the exhaust vents 52 which fluidly communicate with the valve chamber 59).

In the mask 10, the cooperative engagement between the exhalation valve 12 and the cushion 14 is facilitated by the advancement of the wall portion 46 of the seat member 40 into the valve opening 26 defined by the cushion 14. As best seen in FIG. 5, such advancement is limited by the ultimate abutment or engagement of a beveled seating surface 76 defined by the flange portion 50 of the seat member 40 against the complimentary valve seat 27 of the cushion 14 circumventing the valve opening 26. Upon the engagement of the seating surface 76 to the valve seat 27, the fluid chamber 22 of the cushion 14 fluidly communicates with the fluid conduit defined by the wall portion 46 of the seat member 40. As will be recognized, if the diaphragm 44 resides in its normal, open position, the fluid chamber 22 is further placed into fluid communication with the valve chamber 59 via the fluid conduit defined by the wall portion 46, neither end of which is blocked or obstructed by virtue of the gap defined between the lip 72 of the diaphragm 44 and the seating surface 49 of the wall portion 46.

When the exhalation valve 12 is operatively coupled to the cushion 14, in addition to the valve seat 27 being seated against the seating surface 76, the first and second inner end surfaces 28, 30 of the cushion 14 are seated against respective, diametrically opposed sections of the flange portion 68 defined by the cap member 42. As best seen in FIGS. 3 and 4, the orientation of the exhalation valve 12 relative to the cushion 14 is such that the end of the valve pilot lumen 38 extending to the second inner end surface 30 is aligned and fluidly communicates with the pilot port 74 within the flange portion 60. As such, in the mask 10, the valve pilot lumen 38 is in continuous, fluid communication with that portion of the valve chamber 59 defined between the inner surface 56 of the base portion 54 and the body portion 66 of the diaphragm 44.

To assist in maintaining the cooperative engagement between the exhalation valve 12 and the cushion 14, the mask 10 is further preferably provided with an elongate frame member 78. The frame member 78 has a generally V-shaped configuration, with a central portion thereof being accommodated by and secured within the complimentary groove 64 formed in the outer surface 58 defined by the base portion 54 of the cap member 42. As shown in FIGS. 3 and 4, the opposed end portions of the frame members 78 are cooperatively engaged to respective ones of the first and second outer end surfaces 18, 20 of the cushion 14. More particularly, as shown in FIG. 2, the frame member 78 includes an identically configured pair of first and second connectors 80, 82 which extend from respective ones of the opposed end portions thereof. An inner portion of the first connector 80 is advanced into and frictionally retained within the first gas delivery lumen 32 of the cushion 14. Similarly, an inner portion of the second connector 82 is advanced into and frictionally retained within the second gas delivery lumen 34 of the cushion 14. In addition to the inner portions advanced into respective ones of the first and second gas delivery lumens 32, 34, the first and second connectors 80, 82 of the frame member 78 each further include an outer portion which, as will be described in more detail below, is adapted to be advanced into and frictionally retained within a corresponding lumen of a respective one of a pair of bi-lumen tubes fluidly coupled to the mask 10.

As shown in FIGS. 3 and 4, the frame member 78 further includes a tubular, cylindrically configured pressure port 84 which is disposed adjacent the first connector 80. The pressure port 84 is aligned and fluidly communicates with the pressure sensing lumen 36 of the cushion 14. Similarly, the frame member 78 is also provided with a tubular, cylindrically configured pilot port 86 which is disposed adjacent the second connector 82. The pilot port 86 is aligned and fluidly communicates with the valve pilot lumen 38 of the cushion 14. As will also be discussed in more detail below, the pressure and pilot ports 84, 86 of the frame member 78 are adapted to be advanced into and frictionally maintained within corresponding lumens of respective ones of the aforementioned pair of bi-lumen tubes which are fluidly connected to the mask 10 within a ventilation system incorporating the same. The receipt of the frame member 78 within the groove 64 of the cap member 42 ensures that the cushion 14, the exhalation valve 12 and the frame member 78 are properly aligned, and prevents relative movement therebetween. Though not shown, it is contemplated that in one potential variation of the mask 10, the cushion 14 may be formed so as not to include the valve pilot lumen 38. Rather, a suitable valve pilot lumen would be formed directly within the frame member 78 so as to extend therein between the pilot port 86 thereof and the pilot port 74 of the exhalation valve 12.

In the mask 10, the exhalation valve 12 is piloted, with the movement of the diaphragm 44 to the closed position described above being facilitated by the introduction of positive fluid pressure into the valve chamber 59. More particularly, it is contemplated that during the inspiratory phase of the breathing cycle of a patient wearing the mask 10, the valve pilot lumen 38 will be pressurized by a pilot line fluidly coupled to the pilot port 86, with pilot pressure being introduced into that portion of the valve chamber 59 normally defined between the body portion 66 of the diaphragm 44 and the inner surface 56 defined by the base portion 54 of the cap member 42 via the pilot port 74 extending through the flange portion 60 of the cap member 42. The fluid pressure level introduced into the aforementioned region of the valve chamber 59 via the pilot port 74 will be sufficient to facilitate the movement of the diaphragm 44 to its closed position described above.

Conversely, during the expiratory phase of the breathing cycle of the patient wearing the mask 10, it is contemplated that the discontinuation or modulation of the fluid pressure through the valve pilot lumen 38 and hence into the aforementioned region of the valve chamber 59 via the pilot port 74, coupled with the resiliency of the diaphragm 44 and/or positive pressure applied to the body portion 66 thereof, will facilitate the movement of the diaphragm 44 back to the open position or to a partially open position. In this regard, positive pressure as may be used to facilitate the movement of the diaphragm 44 to its open position may be provided by air which is exhaled from the patient during the expiratory phase of the breathing circuit and is applied to the body portion 66 via the pillows portions 24 of the cushion 14, the fluid chamber 22, and the fluid conduit defined by the wall portion of the seat member 40. As will be recognized, the movement of the diaphragm 44 to the open position allows the air exhaled from the patient to be vented to ambient air after entering the valve chamber 59 via the exhaust vents 52 within the flange portion 50 of the seat member 40 which, as indicated above, fluidly communicate with the valve chamber 59.

As will be recognized, based on the application of pilot pressure thereto, the diaphragm 44 travels from a fully open position through a partially open position to a fully closed position. In this regard, the diaphragm 44 will be partially open or partially closed during exhalation to maintain desired ventilation therapy. Further, when pilot pressure is discontinued to the diaphragm 44, it moves to an open position wherein the patient can inhale and exhale through the mask 10 with minimal restriction and with minimal carbon dioxide retention therein. This is an important feature of the present invention which allows a patient to wear the mask 10 without ventilation therapy being applied to the mask 10, the aforementioned structural and functional features of the mask 10 making it more comfortable to wear, and further allowing it to be worn without carbon dioxide buildup. This feature is highly advantageous for the treatment of obstructive sleep apnea wherein patients complain of discomfort with ventilation therapy due to mask and pressure discomfort. When it is detected that a patient requires sleep apnea therapy, the ventilation therapy can be started (i.e., in an obstructive sleep apnea situation).

To succinctly summarize the foregoing description of the structural and functional features of the mask 10, during patient inhalation, the valve pilot lumen 38 is pressurized, which causes the diaphragm 44 to close against the seating surface 49, thus effectively isolating the fluid chamber 22 of the mask 10 from the outside ambient air. The entire flow delivered from a flow generator fluidly coupled to the mask 10 is inhaled by the patient, assuming that unintentional leaks at the interface between the cushion 14 and the patient are discarded. This functionality differs from what typically occurs in a conventional CPAP mask, where venting to ambient air is constantly open, and an intentional leak flow is continuously expelled to ambient air. During patient exhalation, the pilot pressure introduced into the valve pilot lumen 38 is controlled so that the exhaled flow from the patient can be exhausted to ambient air through the exhalation valve 12 in the aforementioned manner. In this regard, the pilot pressure is "servoed" so that the position of the diaphragm 44 relative to the seating surface 49 is modulated, hence modulating the resistance of the exhalation valve 12 to the exhaled flow and effectively ensuring that the pressure in the fluid chamber 22 of the mask 10 is maintained at a prescribed therapeutic level throughout the entire length of the exhalation phase. When the valve pilot lumen 38 is not pressurized, the exhalation valve 12 is in a normally open state, with the diaphragm 44 being spaced from the seating surface 49 in the aforementioned manner, thus allowing the patient to spontaneously breathe in and out with minimal pressure drop (also referred to as back-pressure) in the order of less than about 2 cm H2O at 60 l/min. As a result, the patient can comfortably breathe while wearing the mask 10 and while therapy is not being administered to the patient.

Figure 11A:
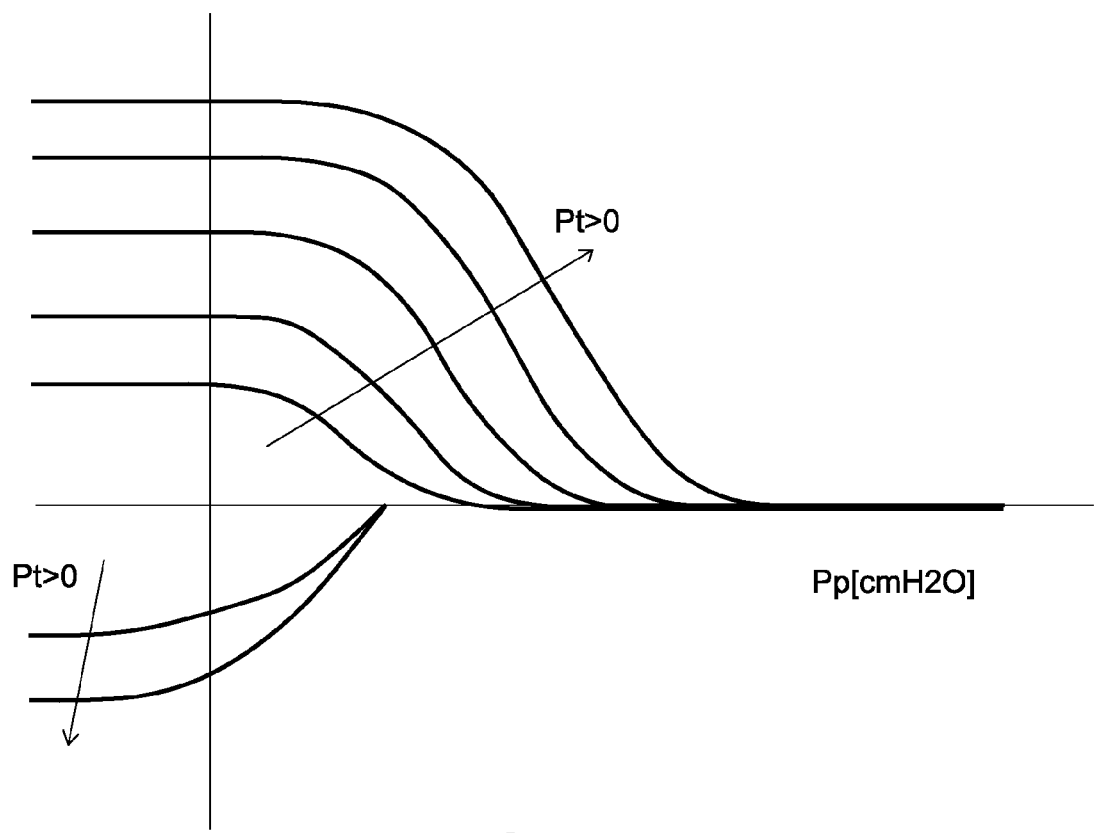
FIGS. 11A, 11B and 11C are a series of graphs which provide visual representations corresponding to exemplary performance characteristics of the exhalation valve subassembly of any nasal pillows mask constructed in accordance with the present invention.
Figure 11B:
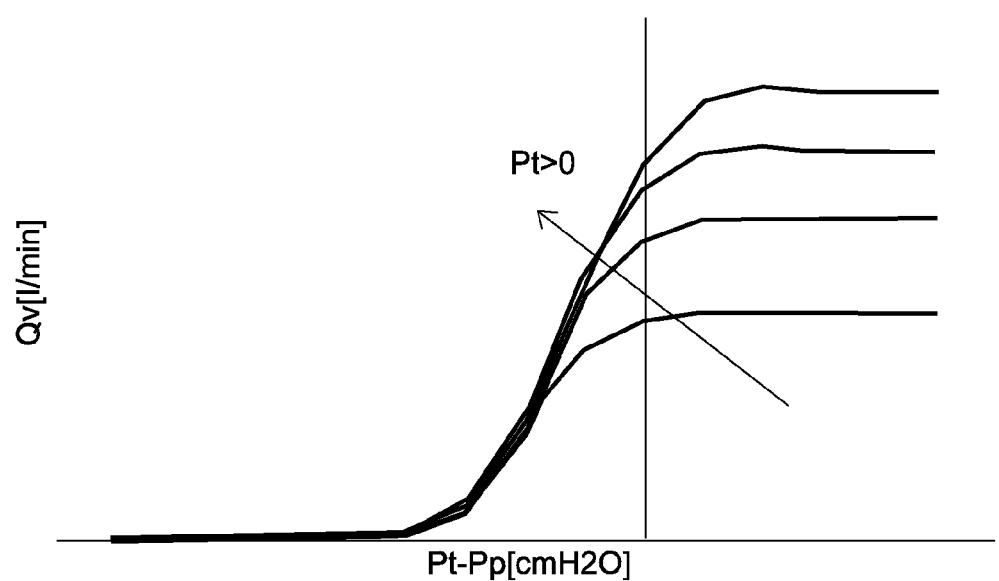
Figure 11C:
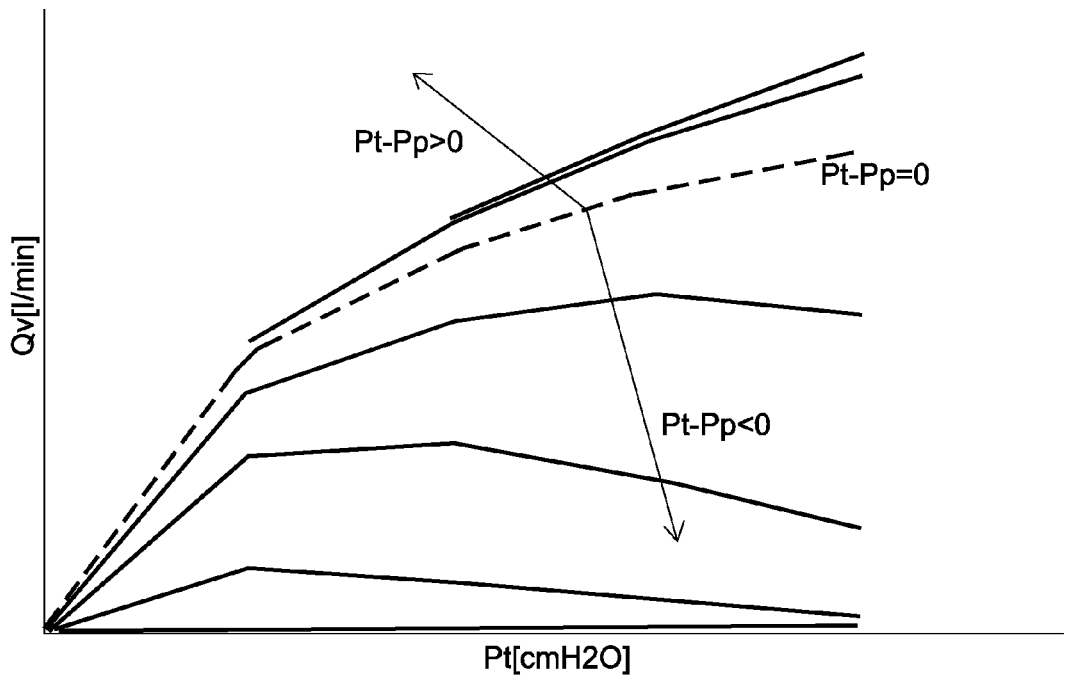

Referring now to FIGS. 11A, 11B and 11C, during use of the mask 10 by a patient, the functionality of the exhalation valve 12 can be characterized with three parameters. These are Pt which is the treatment pressure (i.e., the pressure in the mask 10 used to treat the patient; Pp which is the pilot pressure (i.e., the pressure used to pilot the diaphragm 44 in the exhalation valve 12); and Qv which is vented flow (i.e., flow that is exhausted from inside the exhalation valve 12 to ambient. These three particular parameters are labeled as Pt, Pp and Qv in FIG. 9. When the patient is ventilated, Pt is greater than zero, with the functionality of the exhalation valve 12 being described by the family of curves in the first and second quadrants of FIG. 11A. In this regard, as apparent from FIG. 11A, for any given Pt, it is evident that by increasing the pilot pressure Pp, the exhalation valve 12 will close and the vented flow will decrease. A decrease in the pilot pressure Pp will facilitate the opening of the valve 12, thereby increasing vented flow. The vented flow will increase until the diaphragm 44 touches or contacts the inner surface 56 of the base portion 54 of the cap member 42, and is thus not able to open further. Conversely, when the patient is not ventilated, the inspiratory phase can be described by the third and fourth quadrants. More particularly, Qv is negative and air enters the mask 10 through the valve 12, with the pressure Pt in the mask 10 being less than or equal to zero. Pilot pressure Pp less than zero is not a configuration normally used during ventilation of the patient, but is depicted for a complete description of the functionality of the valve 12. The family of curves shown in FIG. 11A can be described by a parametric equation. Further, the slope and asymptotes of the curves shown in FIG. 11A can be modified by, for example and not by way of limitation, changing the material used to fabricate the diaphragm 44, changing the thickness of the diaphragm 44, changing the area ratio between the pilot side and patient side of the diaphragm 44, changing the clearance between the diaphragm 44 and the seating surface 49, and/or changing the geometry of the exhaust vents 52.

An alternative representation of the functional characteristics of the valve 12 can be described by graphs in which $\Delta P = Pt - Pp$ is shown. For example, the graph of FIG. 11B shows that for any given Pt, the vented flow can be modulated by changing $\Delta P$. In this regard, $\Delta P$ can be interpreted as the physical position of the diaphragm 44. Since the diaphragm 44 acts like a spring, the equation describing the relative position d of the diaphragm 44 from the seating surface 49 of the seat member 40 is $k \cdot d + Pt \cdot At = Pp \cdot Ap$, where At is the area of the diaphragm 44 exposed to treatment pressure Pt and Ap is the area of the diaphragm 44 exposed to the pilot pressure Pp. A similar, alternative representation is provided in the graph of FIG. 11C which shows Pt on the x-axis and $\Delta P$ as the parameter. In this regard, for any given $\Delta P$, the position d of the diaphragm 44 is determined, with the valve 12 thus being considered as a fixed opening valve. In this scenario Pt can be considered the driving pressure pushing air out of the valve 12, with FIG. 11C further illustrating the highly non-linear behavior of the valve 12.

Figure 12:
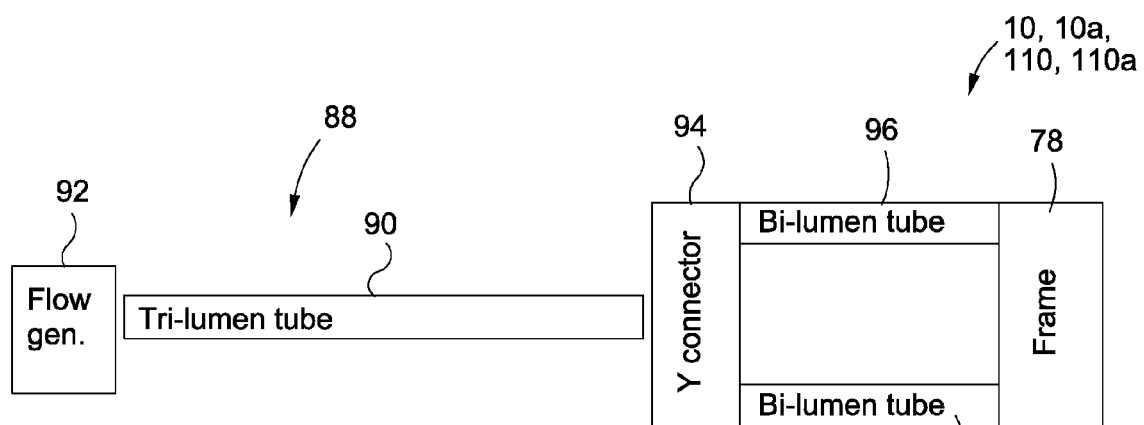
FIG. 12 is a schematic representation of an exemplary ventilation system wherein a tri-lumen tube is used to facilitate the operative interface between any nasal pillows mask constructed in accordance with the present invention a flow generating device.

FIG. 12 provides a schematic representation of an exemplary ventilation system 88 wherein a tri-lumen tube 90 is used to facilitate the fluid communication between the mask 10 and a blower or flow generator 92 of the system 88. As represented in FIG. 12, one end of the tri-lumen tube 90 is fluidly connected to the flow generator 92, with the opposite end thereof being fluidly connected to a Y-connector 94. The three lumens defined by the tri-lumen tube 90 include a gas delivery lumen, a pressure sensing lumen, and a valve pilot lumen. The gas delivery lumen is provided with an inner diameter or ID in the range of from about 2 mm to 15 mm, and preferably about 4 mm to 10 mm. The pressure sensing and valve pilot lumens of the tri-lumen tube 90 are each preferably provided with an ID in the range of from about 0.5 mm to 2 mm. The outer diameter or OD of the tri-lumen tube 90 is preferably less than 17 mm, with the length thereof in the system 88 being about 2 m. The Y-connector 94 effectively bifurcates the tri-lumen tube 90 into the first and second bi-lumen tubes 96, 98, each of which has a length of about 6 inches. The first bi-lumen tube 96 includes a gas delivery lumen having an ID in the same ranges described above in relation to the gas delivery lumen of the tri-lumen tube 90. The gas delivery lumen of the first bi-lumen tube 96 is fluidly coupled to the outer portion of the first connector 80 of the frame member 78. The remaining lumen of the first bi-lumen tube 96 is a pressure sensing lumen which has an ID in the same range described above in relation to the pressure sensing lumen of the tri-lumen tube 90, and is fluidly coupled to the pressure port 84 of the frame member 78. Similarly, the second bi-lumen tube 98 includes a gas delivery lumen having an ID in the same ranges described above in relation to the gas delivery lumen of the tri-lumen tube 90. The gas delivery lumen of the second bi-lumen tube 98 is fluidly coupled to the outer portion of the second connector 82 of the frame member 78. The remaining lumen of the second bi-lumen tube 98 is a valve pilot lumen which has an ID in the same range described above in relation to the valve pilot lumen of the tri-lumen tube 90, and is fluidly coupled to the pilot port 86 of the frame member 78.

In the system 88 shown in FIG. 12, the pilot pressure is generated at the flow generator 92. In the prior art, a secondary blower or proportional valve that modulates the pressure from a main blower is used to generate a pressure to drive an expiratory valve. However, in the system 88 shown in FIG. 12, the outlet pressure of the flow generator 92 is used, with the flow generator 92 further being controlled during patient exhalation in order to have the correct pilot pressure for the exhalation valve 12. This allows the system 88 to be inexpensive, not needing additional expensive components such as proportional valves or secondary blowers.

Figure 13:
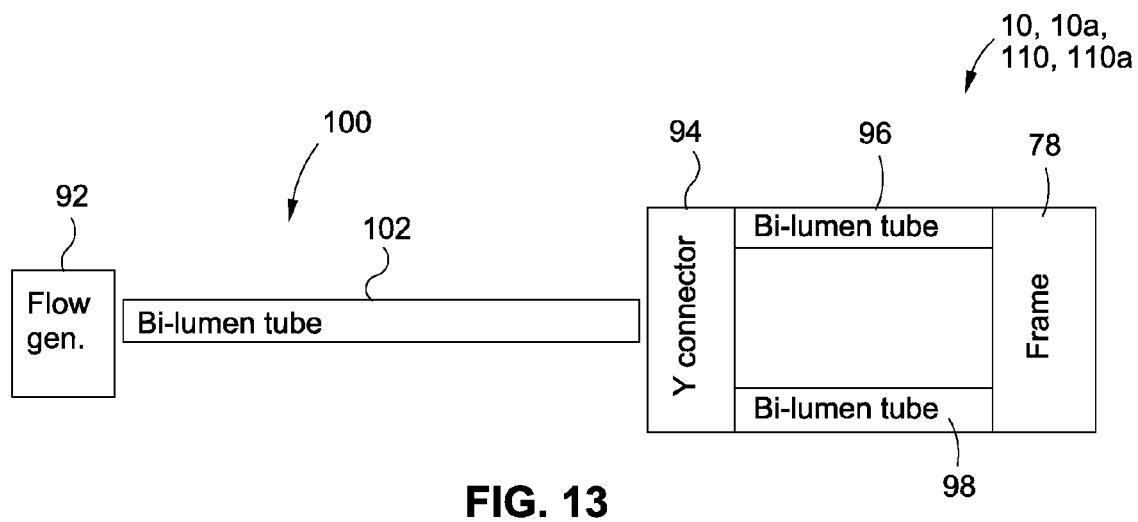
FIG. 13 is a schematic representation of an exemplary ventilation system wherein a bi-lumen tube is used to facilitate the operative interface between any nasal pillows mask constructed in accordance with the present invention and a flow generating device.

FIG. 13 provides a schematic representation of another exemplary ventilation system 100 wherein a bi-lumen tube 102 is used to facilitate the fluid communication between the mask 10 and the blower or flow generator 92 of the system 100. As represented in FIG. 13, one end of the bi-lumen tube 102 is fluidly connected to the flow generator 92, with the opposite end thereof being fluidly connected to the Y-connector 94. The two lumens defined by the bi-lumen tube 102 include a gas delivery lumen and a pressure sensing lumen. The gas delivery lumen is provided with an inner diameter or ID in the range of from about 2 mm to 10 mm, and preferably about 4 mm to 7 mm. The pressure sensing lumen of the bi-lumen tube 102 is preferably provided with an ID in the range of from about 0.5 mm to 2 mm. The outer diameter or OD of the bi-lumen tube 90 is preferably less than 11 mm, with the length thereof being about 2 m. The Y-connector 94 effectively bifurcates the bi-lumen tube 102 into the first and second bi-lumen tubes 96, 98, each of which has a length of about 6 inches. The first bi-lumen tube 96 includes a gas delivery lumen having an ID in the same ranges described above in relation to the gas delivery lumen of the bi-lumen tube 102. The gas delivery lumen of the first bi-lumen tube 96 is fluidly coupled to the outer portion of the first connector 80 of the frame member 78. The remaining lumen of the first bi-lumen tube 96 is a pressure sensing lumen which has an ID in the same range described above in relation to the pressure sensing lumen of the bi-lumen tube 102, and is fluidly coupled to the pressure port 84 of the frame member 78. Similarly, the second bi-lumen tube 98 includes a gas delivery lumen having an ID in the same ranges described above in relation to the gas delivery lumen of the bi-lumen tube 102. The gas delivery lumen of the second bi-lumen tube 98 is fluidly coupled to the outer portion of the second connector 82 of the frame member 78. The remaining lumen of the second bi-lumen tube 98 is a valve pilot lumen which has an ID in the same range described above in relation to the pressure sensing lumen of the bi-lumen tube 102, and is fluidly coupled to the pilot port 86 of the frame member 78.

In the system 100 shown in FIG. 13, the valve pilot lumen 38 is connected to the gas delivery air path at the Y-connector 94. More particularly, the gas delivery lumen of the bi-lumen tube 102 is transitioned at the Y-connector 94 to the valve pilot lumen of the second bi-lumen tube 98. As such, the pilot pressure will be proportional to the outlet pressure of the flow generator 92 minus the pressure drop along the bi-lumen tube 102, which is proportional to delivered flow. This solution is useful when small diameter tubes are used in the system 100, since such small diameter tubes require higher outlet pressure from the flow generator 92 for the same flow. In this regard, since the pressure at the outlet of the flow generator 92 would be excessive for piloting the exhalation valve 12, a lower pressure along the circuit within the system 100 is used. In the system 100, though it is easier to tap in at the Y-connector 94, anywhere along the tube network is acceptable, depending on the pressure level of the flow generator 92 which is the pressure required by the patient circuit in order to deliver the therapeutic pressure and flow at the patient.

In each of the systems 88, 100, it is contemplated that the control of the flow generator 92, and hence the control of therapeutic pressure delivered to the patient wearing the mask 10, may be governed by the data gathered from dual pressure sensors which take measurements at the mask 10 and the output of the flow generator 92. As will be recognized, pressure sensing at the mask 10 is facilitated by the pressure sensing lumen 36 which, as indicated above, is formed within the cushion 14 and fluidly communicates with the fluid chamber 22 thereof. As also previously explained, one of the lumens of the first bi-lumen tube 96 in each of the systems 88, 100 is coupled to the pressure port 84 (and hence the pressure sensing lumen 36). As a result, the first bi-lumen tube 96, Y-connector 94 and one of the tri-lumen or bi-lumen tubes 90, 102 collectively define a continuous pressure sensing fluid path between the mask 10 and a suitable pressure sensing modality located remotely therefrom. A more detailed discussion regarding the use of the dual pressure sensors to govern the delivery of therapeutic pressure to the patient is found in Applicant's co-pending U.S. application Ser. No. 13/411,257 entitled Dual Pressure Sensor Continuous Positive Airway Pressure (CPAP) Therapy filed Mar. 2, 2012, the entire disclosure of which is incorporated herein by reference.

Figure 10:
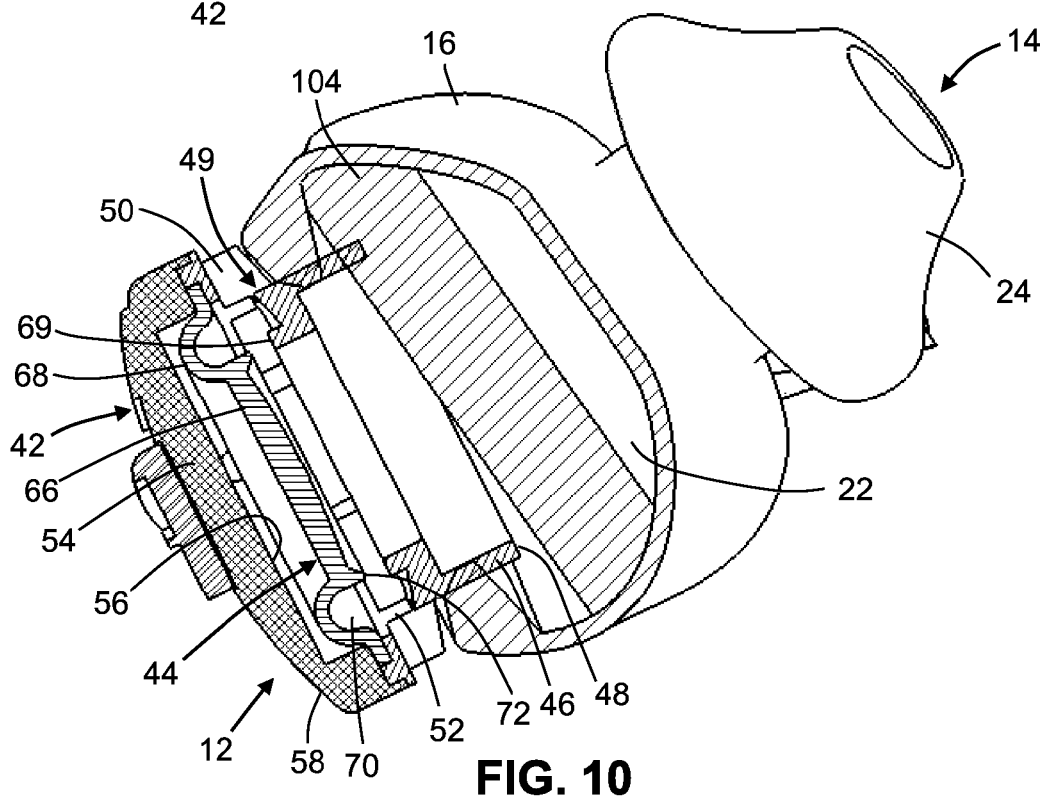
FIG. 10 is a cross-sectional view similar to FIG. 5, but depicting a variant of the nasal pillows mask shown in FIG. 1 wherein an HME is integrated into the cushion thereof.

Referring now to FIG. 10, there is shown a mask 10a which comprises a variant of the mask 10. The sole distinction between the masks 10, 10a lies in the mask 10a including a heat and moisture exchanger or HME 104 which is positioned within the fluid chamber 22 of the cushion 14. The HME 104 is operative to partially or completely replace a humidifier (cold or heated pass-over; active or passive) which would otherwise be fluidly coupled to the mask 10a. This is possible because the average flow through the system envisioned to be used in conjunction with the mask 10a is about half of a prior art CPAP mask, due to the absence of any intentional leak in such system.

The HME 104 as a result of its positioning within the fluid chamber 22, is able to intercept the flow delivered from the flow generator to the patient in order to humidify it, and is further able to capture humidity and heat from exhaled flow for the next breath. The pressure drop created by the HME 104 during exhalation (back-pressure) must be limited, in the order of less than 5 cm H2O at 60 l/min, and preferably lower than 2 cm H2O at 60 l/min. These parameters allow for a low back-pressure when the patient is wearing the mask 10a and no therapy is delivered to the patient.

It is contemplated that the HME 104 can be permanently assembled to the cushion 14, or may alternatively be removable therefrom and thus washable and/or disposable. In this regard, the HME 104, if removable from within the cushion 14, could be replaced on a prescribed replacement cycle. Additionally, it is contemplated that the HME 104 can be used as an elastic member that adds elasticity to the cushion 14. In this regard, part of the elasticity of the cushion 14 may be attributable to its silicone construction, and further be partly attributable to the compression and deflection of the HME 104 inside the cushion 14.

Referring now to FIGS. 15-19, there is shown a ventilation mask 110 (e.g., a nasal pillows mask) constructed in accordance with another embodiment of the present invention. Like the mask 10 described above, the mask 110 includes an integrated, diaphragm-implemented, piloted exhalation valve 112, the structural and functional attributes of which will be described in more detail below.

As shown in FIGS. 15-19, the mask 110 comprises a housing or cushion 114. The cushion 114, which is preferably fabricated from a silicone elastomer having a Shore A hardness in the range of from about 20 to 60 and preferably about 40, is formed as a single, unitary component, and is shown individually in FIG. 20. The cushion 114 includes a main body portion 116 which defines a first outer end surface 118 and an opposed second outer end surface 120. The main body portion 116 further defines an interior fluid chamber 122 which is of a prescribed volume. In addition to the main body portion 116, the cushion 14 includes an identically configured pair of hollow pillow portions 124 which protrude from the main body portion 116 in a common direction and in a prescribed spatial relationship relative to each other. More particularly, in the cushion 114, the spacing between the pillow portions 124 is selected to facilitate the general alignment thereof with the nostrils of an adult patient when the mask 110 is worn by such patient. Each of the pillow portions 124 fluidly communicates with the fluid chamber 122.

Figure 16:
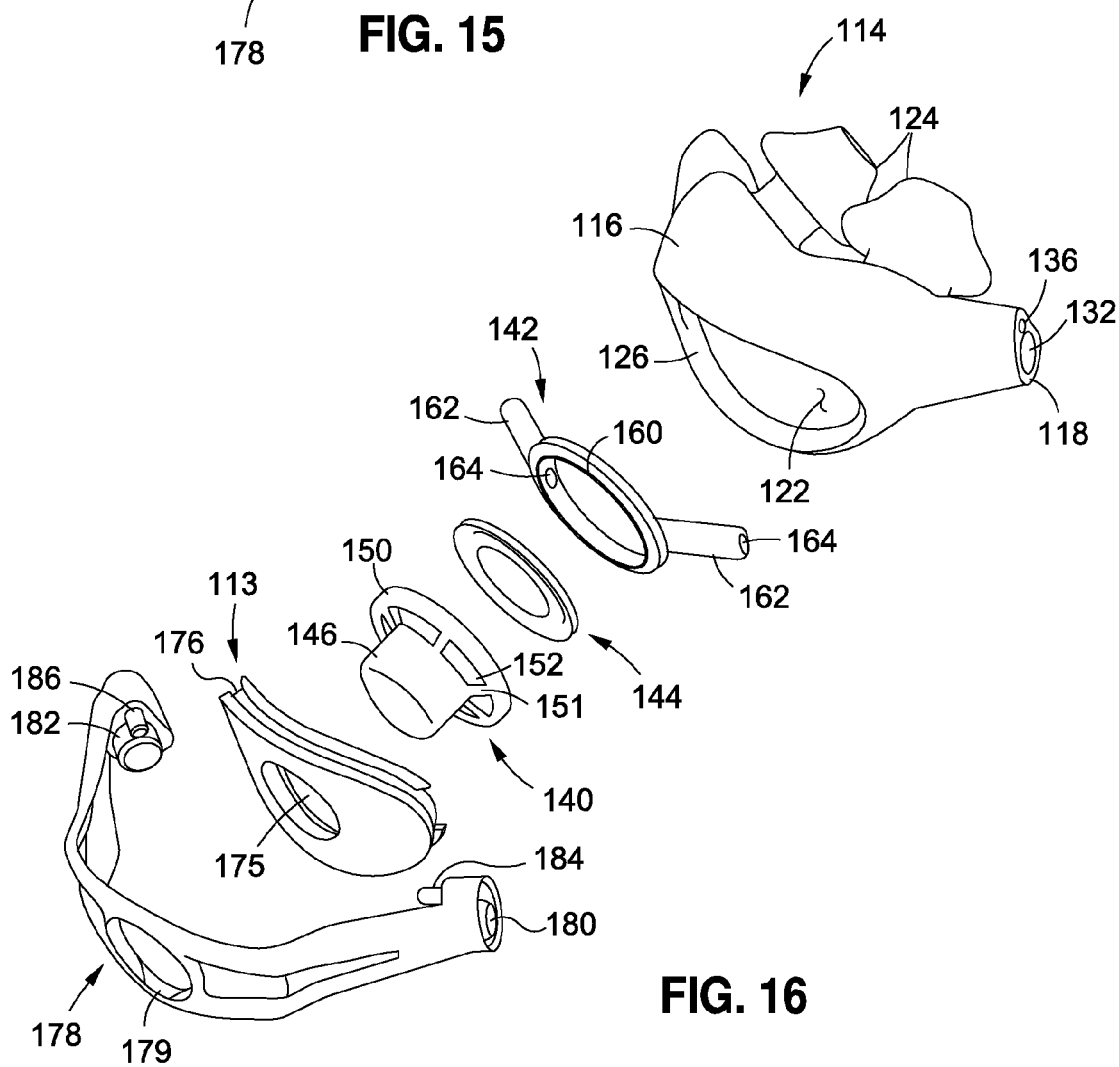
FIG. 16 is an exploded view of the nasal pillows mask shown in FIG. 15.

As shown in FIG. 16, the main body portion 116 of the cushion 114 includes an enlarged, circularly configured valve opening 126 which is in direct fluid communication with the fluid chamber 122. The valve opening 126 is positioned in generally opposed relation to the pillow portions 124 of the cushion 114. The valve opening 126 is adapted to accommodate an exhalation valve subassembly 111 of the mask 110 in a manner which will be described in more detail below.

Figure 18:
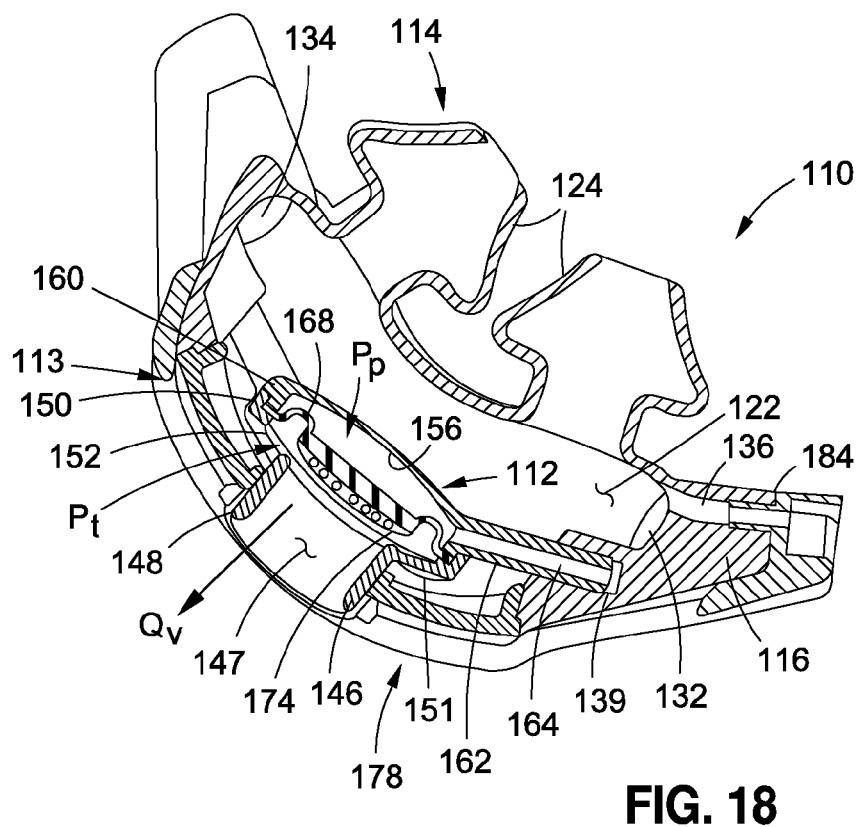
FIG. 18 is a partial cross-sectional view of the nasal pillows mask shown in FIG. 15 taken along lines 18-18 thereof, and depicting the pressure sensing lumen extending through the cushion of the mask.
Figure 19:
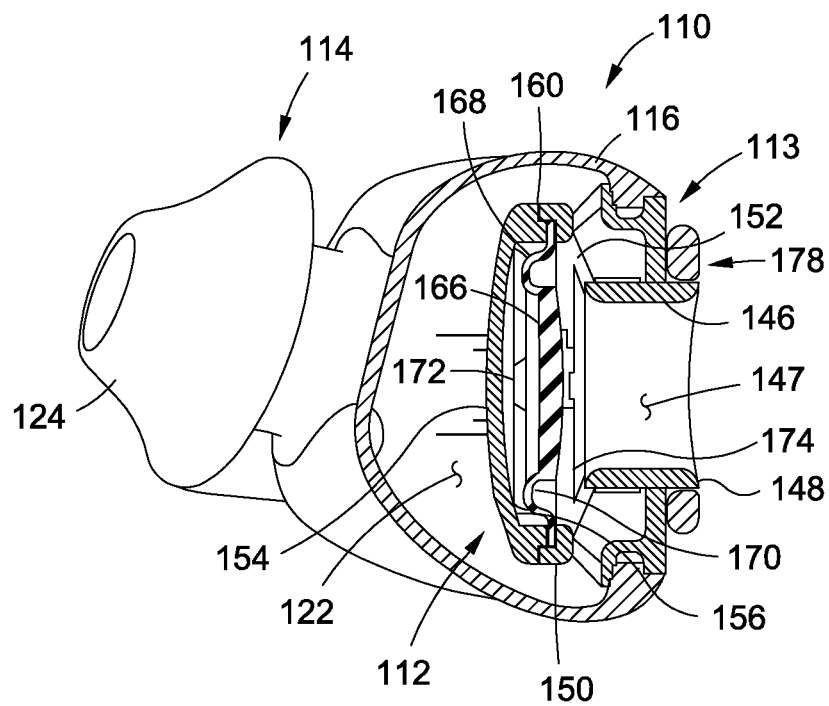
FIG. 19 is a cross-sectional view of the nasal pillows mask shown in FIG. 15 taken along lines 19-19 thereof.
Figure 20:
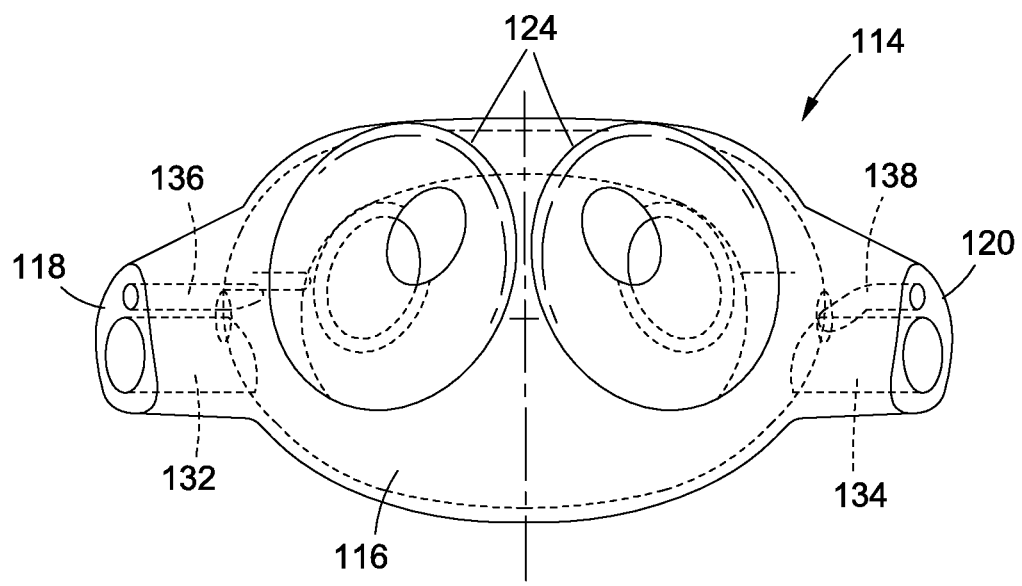
FIG. 20 is a top perspective view of cushion of the nasal pillows mask shown in FIG. 15.
Figure 21:
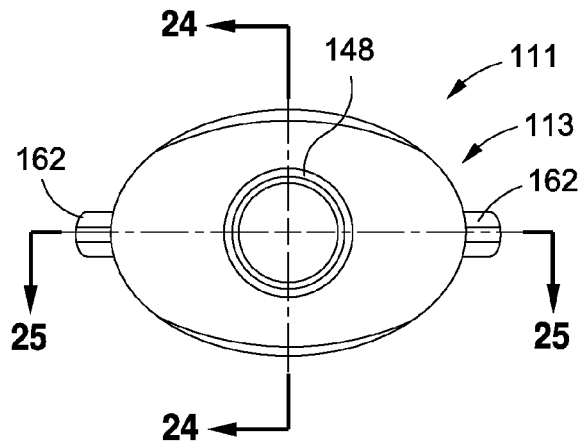
FIG. 21 is a front elevational view of the exhalation valve subassembly for the nasal pillows mask shown in FIG. 15.
Figure 22:
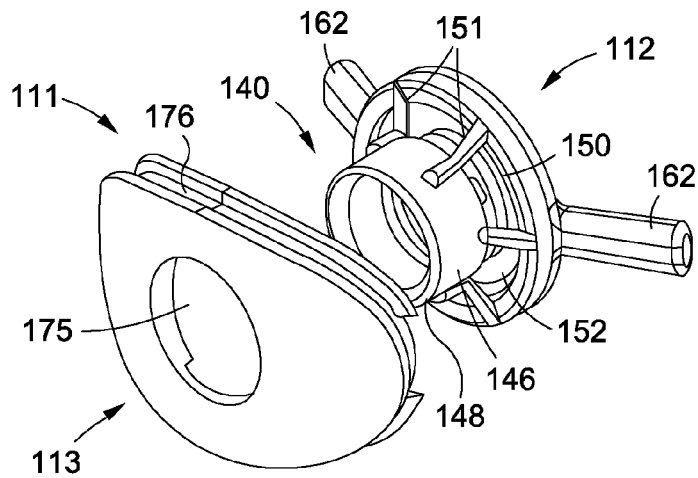
FIG. 22 is a front exploded view of the exhalation valve subassembly shown in FIG. 21, depicting the exhalation valve and the shield plate thereof.
Figure 23:
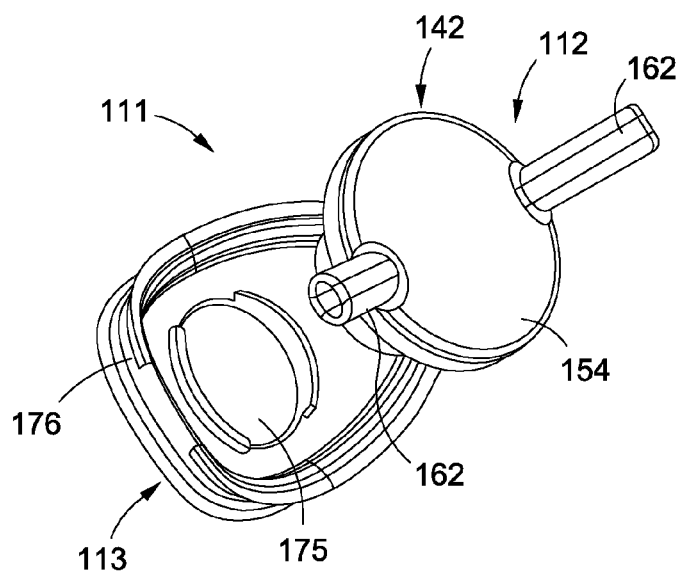
FIG. 23 is a rear exploded view of the exhalation valve subassembly shown in FIG. 21, depicting the exhalation valve and the shield plate thereof.
Figure 24:
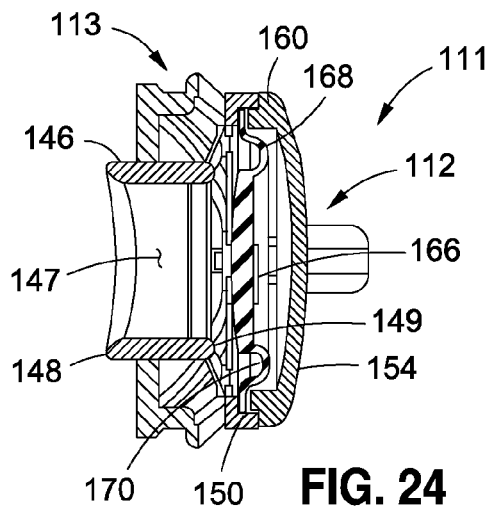
FIG. 24 is a cross-sectional view of the exhalation valve subassembly shown in FIG. 21 taken along lines 24-24 thereof.
Figure 25:
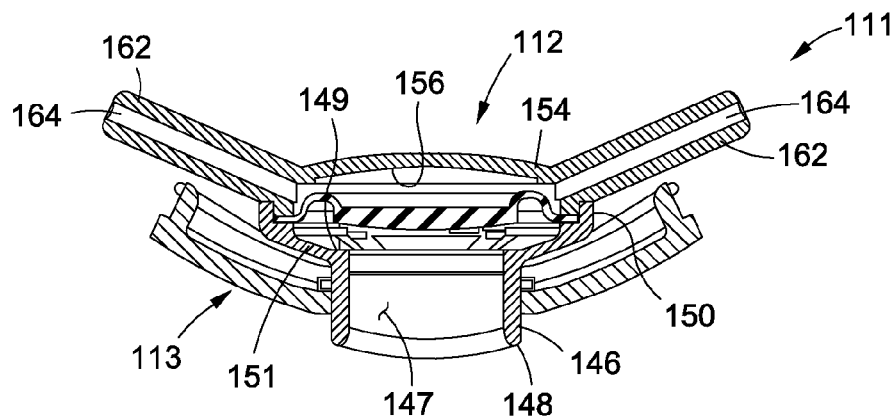
FIG. 25 is a cross-sectional view of the exhalation valve subassembly shown in FIG. 21 taken along lines 25-25 thereof.

The main body portion 116 of the cushion 114 further defines first and second gas delivery lumens 132, 134 which extend from respective ones of the first and second outer end surfaces 118, 120 into fluid communication with the fluid chamber 122. Additionally, a pressure sensing lumen 136 defined by the main body portion 116 extends from the first outer end surface 118 into fluid communication with the fluid chamber 122. The main body portion 116 further defines a valve pilot lumen 138 which extends from the second outer end surface 120 into fluid communication with the fluid chamber. Those of ordinary skill in the art will recognize that the gas delivery lumens 132, 134 may be substituted with a single gas delivery lumen and/or positioned within the cushion 114 in orientations other than those depicted in FIG. 20. For example, the gas delivery lumen(s) of the cushion 114 may be positioned frontally, pointing upwardly, pointing downwardly, etc. rather than extending laterally as shown in FIG. 20. The main body portion 116 of the cushion 114 further includes a mounting aperture 139 formed therein. As seen in FIG. 18, one end of the mounting aperture 139 communicates with the fluid chamber 122, with the opposite simply terminating blindly within the main body portion 116. The use of the first and second gas delivery lumens 132, 134, the pressure sensing lumen 136, the valve pilot lumen 138 and the mounting aperture 139 will be discussed in more detail below.

Referring now to FIGS. 16-19 and 21-26, the exhalation valve subassembly 111 of the mask 110 comprises the aforementioned exhalation valve 112 in combination with a shield plate 113. The exhalation valve 112 of the mask 110 is itself made of three (3) parts or components, and more particularly a seat member 140, a cap member 142, and a diaphragm 144 which is operatively captured between the seat and cap members 140, 142. The seat and cap members 140, 142 are each preferably fabricated from a plastic material, with the diaphragm 144 preferably being fabricated from an elastomer having a Shore A hardness in the range of from about 20-40.

The seat member 140 includes a tubular, generally cylindrical wall portion 146 which defines a distal, annular outer rim 148 and an opposed annular inner seating surface 149. The wall portion further defines an outlet conduit 147 which extends between the outer rim 148 and seating surface 149. In addition to the wall portion 146, the seat member 140 includes an annular flange portion 150 which is integrally connected to the wall portion 146 by a series of spoke portions 151. The spoke portions 151 extend to locations on the wall portion 146 proximate the seating surface 149, with the flange portion 150 being positioned radially outward relative to the wall portion 146. In the seat member 140, the wall, flange and spoke portions 146, 150, 151 collectively define a plurality of exhaust vents 152 which are located about the periphery of the wall portion 146 in a prescribed arrangement and spacing relative to each other. The seat member 140 is formed such that each of the exhaust vents 152 normally fluidly communicates with the outlet conduit 147 defined by the wall portion 146.

The cap member 142 of the exhalation valve 112 comprises a circularly configured base portion 154 which defines an inner surface 156. In addition to the base portion 154, the cap member 142 includes an annular flange portion 160 which circumvents and protrudes generally perpendicularly relative to the inner surface 156 of the base portion 154. The cap member 142 further includes an identically configured pair of tube portions 162 which are integrally connected to the flange portion 160 in diametrically opposed relation to each other (i.e., approximately 180° apart). Each of the tube portions defines a lumen 164 extending therethrough and is used for reasons which will be discussed in more detail below. The seat and cap members 140, 142, when attached to each other in the fully assembled exhalation valve 112, collectively define an interior valve chamber of the exhalation valve 112, such valve chamber generally being located between the inner surface 156 defined by the base portion 154 of the cap member 142 and the seating surface 149 defined by the wall portion 146 of the seat member 140.

The diaphragm 144 of the exhalation valve 112, which resides within the valve chamber, has a circularly configured, central body portion 166, and a peripheral flange portion 168 which is integrally connected to and circumvents the body portion 166. The flange portion 168 includes an arcuately contoured primary region and a distal region which protrudes radially from the primary region. As such, the primary region of the flange portion 168 extends between the distal region thereof and the body portion 166, and defines a continuous, generally concave channel 170. The body portion 166 of the diaphragm 144 may optionally be perforated, i.e., be provided with an array of small apertures which extend therethrough.

In the exhalation valve 112, the flange portion 168 of the diaphragm 144 is operatively captured between complementary engagement surfaces defined by the flange portions 150, 160 of the seat and cap members 140, 142. More particularly, the annular distal region of the flange portion 168 is compressed (and thus captured) between an annular shoulder defined by the flange portion 160 of the cap member 142, and a complimentary annular shoulder which is defined by the flange portion 150 of the seat member 140 proximate the exhaust vents 152. The orientation of the diaphragm 144 within the valve chamber when captured between the seat and cap members 140, 142 is such that the channel 170 defined by the arcuately contoured primary region of the flange portion 168 is directed toward or faces the seating surface 149 defined by the wall portion 146 of the seat member 140.

The capture of the diaphragm 144 between the seat and cap members 140, 142 in the aforementioned manner results in the diaphragm 144 effectively segregating the valve chamber collectively defined by the seat and cap members 140, 142 into a pilot section 172 and an exhaust section 174. The pilot section 172 of the valve chamber is located between the diaphragm 144 and the inner surface 156 of the base portion 154 of the cap member 142. The exhaust section 174 of the valve chamber is located between the diaphragm 144 and both the exhaust vents 152 and the seating surface 149 of the wall portion 146 of the seat member 140. In this regard, the outlet conduit 147 defined by the wall portion 146 fluidly communicates with the exhaust section 174 of the valve chamber. In addition, the lumens 164 of the tube portions 162 of the cap member 142 each fluidly communicate with the pilot section 172 of the valve chamber.

The diaphragm 144 (and hence the exhalation valve 112) is selectively moveable between an open position (shown in FIGS. 17-19 and 24-25) and a closed position. When in its normal, open position, the diaphragm 144 is in a relaxed, unbiased state. Importantly, in either of its open or closed positions, the diaphragm 144 is not normally seated directly against the inner surface 156 defined by the base portion 154 of the cap member 142. Rather, a gap is normally maintained between the body portion 166 of the diaphragm 144 and the inner surface 156 of the base portion 154. The width of such gap when the diaphragm 144 is in its open position is generally equal to the fixed distance separating the inner surface 156 of the base portion 154 from the shoulder of the flange portion 160 which engages the distal region of the flange portion 168 of the diaphragm 144. Further, when the diaphragm 144 is in its open position, the body portion 166 is itself disposed in spaced relation to the seating surface 149 defined by the wall portion 146 of the seat member 140. As such, when the diaphragm 144 is in its open position, fluid is able to freely pass through the through the exhaust vents 152, between the seating surface 149 and diaphragm 144, and through the outlet conduit 147 defined by the wall portion 146 to ambient air.

In the exhalation valve 112, the diaphragm 144 is resiliently deformable from its open position (to which it may be normally biased) to its closed position. An important feature of the present invention is that the diaphragm 144 is normally biased to its open position which provides a failsafe to allow a patient to inhale ambient air through the exhalation valve 112 and exhale ambient air therethrough (via the exhaust vents 52) during any ventilator malfunction or when the mask 110 is worn without the therapy being delivered by the ventilator. When the diaphragm 144 is moved or actuated to its closed position, the periphery of the body portion 166 is firmly seated against the seating surface 149 defined by the wall portion 146 of the seat member 140. The seating of the body portion 166 of the diaphragm 144 against the seating surface 149 effectively blocks fluid communication between the outlet conduit 147 defined by the wall portion 146 and the exhaust section 174 of the valve chamber (and hence the exhaust vents 152 which fluidly communicate with the exhaust section 174).

Figure 26:
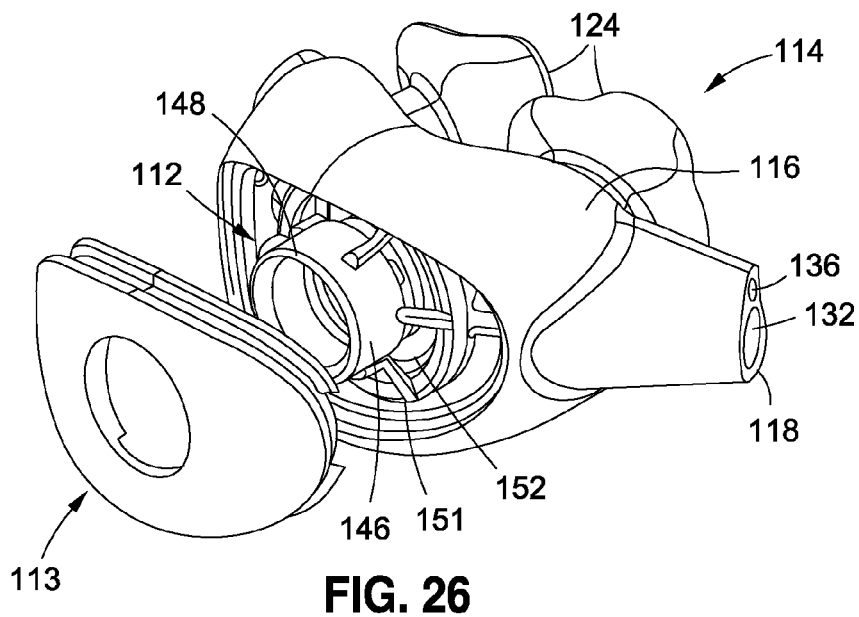
FIG. 26 is a an exploded view of the nasal pillows mask shown in FIG. 15 in a partially assembled state prior to the attachment of the frame member to the cushion, and depicting the separation of the strike plate of the exhalation valve subassembly from the exhalation valve thereof which is positioned within the cushion.

In the mask 110, the cooperative engagement between the exhalation valve 112 and the cushion 114 is facilitated by the advancement of the cap member 142 into the valve opening 126 defined by the cushion 114. Subsequent to such advancement, one of the two tube portions 162 of the cap member 142 is partially advanced into and frictionally retained within the pilot lumen 138 of the cushion 114 in the manner shown in FIG. 17. As is apparent from FIG. 17, the advancement of one tube portion 162 of the cap member 142 into the pilot lumen 138 facilitates the placement of the pilot lumen 138 into fluid communication with the pilot section 172 of the valve chamber via the lumen 164 of the corresponding tube portion 162. The remaining tube portion 162 of the cap member 142 (i.e., that tube portion 162 not advanced into the pilot lumen 138) is advanced into and frictionally retained within the above-described mounting aperture 139 in the manner shown in FIG. 18. Importantly, the resilient construction of the cushion 114, and in particular the main body 116 thereof, allows for the cushion 114 to be bent, twisted or otherwise manipulated as is needed to facilitate the advancement of the tube portions 162 of the cap member 142 into respective ones of the pilot lumen 138 and mounting aperture 139 in the aforementioned manner. The advancement of the tube portions 162 into respective ones of the pilot lumen 138 and mounting aperture 139 causes the exhalation valve 112 to assume a position within the fluid chamber 122 of the cushion 114 as is best shown in FIG. 26. In this regard, the majority of the exhalation valve 112 resides within the fluid chamber 122, with the exception of a small distal section of the wall portion 148 of the seat member 140 which protrudes from the valve opening 126 of the cushion 114.

Due to the positioning of the majority of the exhalation valve 114 within the fluid chamber 122, the exhaust section 174 of the valve chamber is placed into direct fluid communication with the fluid chamber 122 via the exhaust vents 152. Thus, irrespective of whether the diaphragm 144 of the exhalation valve 112 is in its open or closed positions, the pilot lumen 138 of the cushion 114 is maintained in a constant state of fluid communication with the pilot section 172 of the valve chamber. Additionally, irrespective of whether the diaphragm 144 is in its open or closed positions, the fluid chamber 122 is maintained in a constant state of fluid communication with the exhaust section 174 of the valve chamber via the exhaust vents 152. When the diaphragm 144 is in its open position, the fluid chamber 122 is further placed into fluid communication with both the outlet conduit 147 (and hence ambient air) via the open flow path defined between the body portion 166 of the diaphragm 144 and the seating surface 149 of the wall portion 146 of the seat member 140. However, when the diaphragm 144 is moved to its closed position, the fluid communication between the fluid chamber 122 and outlet conduit 147 is effectively blocked by the sealed engagement of the body portion 166 of the diaphragm 144 against the seating surface 149 of the wall portion 146.

As indicated above, in addition to the exhalation valve 112, the exhalation valve subassembly 111 includes the shield plate 113. The shield plate 113 has a generally oval, slightly arcuate profile, and includes a circularly configured opening 175 within the approximate center thereof. Additionally, formed within the peripheral side surface of the shield plate 113 is an elongate groove or channel 176. In the mask 110, the shield plate 113 is adapted to be advanced into the valve opening 126 subsequent to the cooperative engagement of the exhalation valve 112 to the cushion 114 in the aforementioned manner. More particularly, the advancement of the shield plate 113 into the valve opening 126 is facilitated in a manner wherein the wall portion 146 of the seat member 140 is advanced into and through the opening 175 of the shield plate 113. In this regard, the wall portion 146 and the opening 175 have complimentary configurations, with the diameter of the opening 175 only slightly exceeding that of the outer diameter of the wall portion 148.

Subsequent to the advancement of the wall portion 148 into the opening 175, that peripheral edge or lip of the main body 116 of the cushion 114 defining the valve opening 126 is advanced into and firmly seated within the complimentary channel 176 formed in the peripheral side surface of the shield plate 113. The receipt of such edge or lip of the cushion 114 into the channel 176 maintains the shield plate 113 in firm, frictional engagement to the cushion 114. As is seen in FIGS.

17 and 18, the spatial relationship between the exhalation valve 112 and shield plate 113 when each is cooperatively engaged to the cushion 114 in the aforementioned manner is such that the distal section of the wall portion 146 which defines the outer rim 148 thereof protrudes slightly from the exterior surface of the shield plate 113.

As will be recognized, the shield plate 113, when cooperatively engaged to the cushion 114, effectively encloses that portion of the fluid chamber 122 which would otherwise be directly accessible via the valve opening 126. Importantly, by virtue of the attachment of the shield plate 113 to the main body 116 of the cushion 114, virtually the entirety of the exhalation valve 112 is completely enclosed or contained within the fluid chamber 122 of the cushion 114. As indicated above, only a small distal section of the wall portion 146 of the seat member 140 protrudes from the shield plate 113, and in particular the opening 175 defined thereby. As a result, the exhaust vents 152 which facilitate the fluid communication between the fluid chamber 122 and the exhaust section 174 of the valve chamber, and between the fluid chamber 122 and the outlet conduit 147 (and hence ambient air) when the diaphragm 144 is in the open position, are effectively enclosed within the fluid chamber 122 as provides noise attenuation advantages which will be discussed in more detail below.

Figure 15:
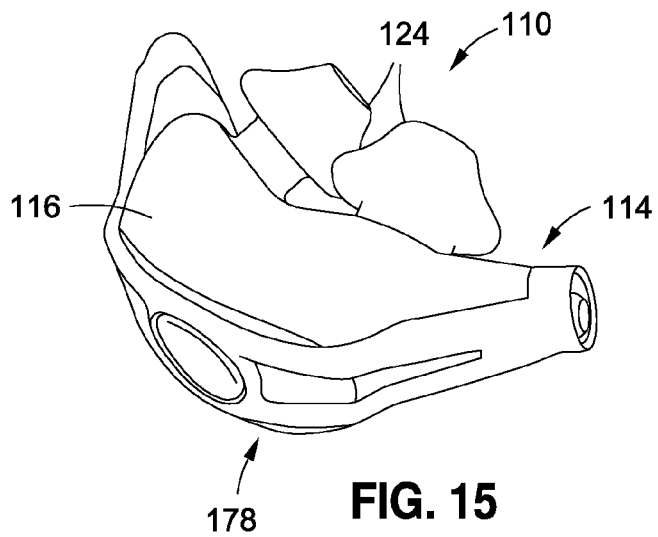
FIG. 15 is top perspective view of a nasal pillows mask constructed in accordance with another embodiment of the present invention and including an integrated diaphragm-based piloted exhalation valve.

To assist in maintaining the cooperative engagement between the exhalation valve subassembly 111 and the cushion 114, the mask 110 is further preferably provided with an elongate reinforcement frame member 178 which is attached to the cushion 114. The frame member 178 has a generally U-shaped configuration, with a central portion thereof including a circularly configured opening 179 formed therein which is adapted to accommodate that aforementioned distal section of the wall portion 146 of the seat member 140 which protrudes from the shield plate 113. In this regard, the diameter of the opening 179 is sized so as to only slightly exceed the outer diameter of the wall portion 146. As seen in FIG. 15, the thickness of the central portion of the frame member 178 is such that when attached to cushion 114 subsequent to the advancement of the wall portion 146 into the complementary opening 179, the outer rim 148 defined by the wall portion 146 is substantially flush or continuous with the exterior surface of the frame member 178.

Figure 17:
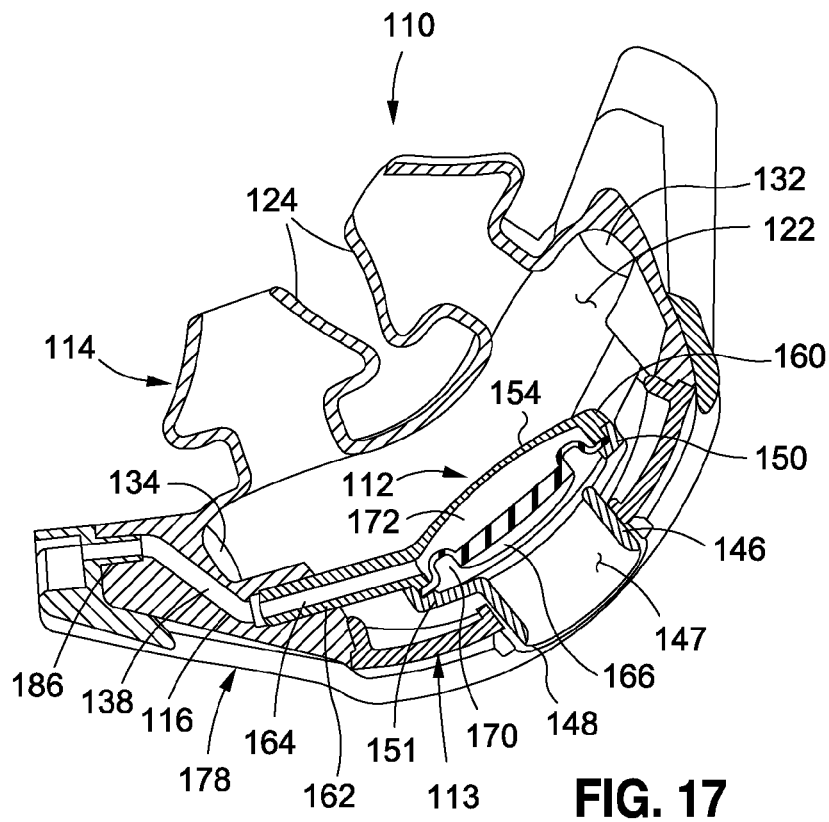
FIG. 17 is a partial cross-sectional view of the nasal pillows mask shown in FIG. 15 taken along lines 17-17 thereof, and depicting the valve pilot lumen extending through the cushion of the mask.

As shown in FIGS. 17 and 18, the opposed end portions of the frame member 178 are cooperatively engaged to respective ones of the first and second outer end surfaces 118, 120 of the cushion 114. More particularly, the frame member 178 includes an identically configured pair of first and second connectors 180, 182 which are formed on respective ones of the opposed end portions thereof. An inner portion of the first connector 180 is advanced into and frictionally retained within the first gas delivery lumen 132 of the cushion 114. Similarly, an inner portion of the second connector 182 is advanced into and frictionally retained within the second gas delivery lumen 134 of the cushion 114. In addition to the inner portions advanced into respective ones of the first and second gas delivery lumens 132, 134, the first and second connectors 180, 182 of the frame member 178 each further include an outer portion which is adapted to be advanced into and frictionally retained within a corresponding lumen of a respective one of a pair of bi-lumen tubes fluidly coupled to the mask 110, in the same manner as described in detail above in relation to the mask 10.

The frame member 178 further includes a tubular, cylindrically configured pressure port 184 which is disposed adjacent the first connector 180. The pressure port 184 is aligned and fluidly communicates with the pressure sensing lumen 136 of the cushion 114. Similarly, the frame member 178 is also provided with a tubular, cylindrically configured pilot port 186 which is disposed adjacent the second connector 182. The pilot port 186 is aligned and fluidly communicates with the valve pilot lumen 138 of the cushion 114. The pressure and pilot ports 184, 186 of the frame member 78 are adapted to be placed into fluid communication with corresponding lumens of respective ones of the aforementioned pair of bi-lumen tubes which are fluidly connected to the mask 110 within a ventilation system incorporating the same, also in the same manner as described in detail above in relation to the mask 10. The receipt of the wall portion 146 of the seat member 140 into the opening 179 of the frame member 178 ensures that the cushion 114, the exhalation valve subassembly 111 and the frame member 178 are properly aligned, and prevents relative movement therebetween.

In the mask 110, the exhalation valve 112 is piloted, with the movement of the diaphragm 144 to the closed position described above being facilitated by the introduction of positive fluid pressure into the pilot section 172 of the valve chamber. More particularly, it is contemplated that during the inspiratory phase of the breathing cycle of a patient wearing the mask 110, the valve pilot lumen 138 will be pressurized by a pilot line fluidly coupled to the pilot port 186, with pilot pressure being introduced into that portion of the pilot section 172 of the valve chamber via the pilot lumen 138 and the lumen 164 of that tube portion 162 of the cap member 142 advanced into the pilot lumen 138. The fluid pressure level introduced into the pilot section 172 of the valve chamber will be sufficient to facilitate the movement of the diaphragm 144 to its closed position described above. When the diaphragm 144 is in its closed position, fluid pressure introduced into the fluid chamber 122 via the gas delivery lumens 136, 138 is prevented from being exhausted to ambient air. In this regard, though such fluid may flow from the fluid chamber 122 into the exhaust section 174 of the valve chamber via the exhaust vents 152, the engagement of the diaphragm 144 to the seating surface 149 defined by the wall portion 146 of the seat member 140 effectively blocks the flow of such fluid into the outlet conduit defined by the wall portion 146 and hence to ambient air.

Conversely, during the expiratory phase of the breathing cycle of the patient wearing the mask 110, it is contemplated that the discontinuation or modulation of the fluid pressure through the valve pilot lumen 138 and hence into the pilot section 172 of the valve chamber, coupled with the resiliency of the diaphragm 144 and/or positive pressure applied to the body portion 166 thereof, will facilitate the movement of the diaphragm 144 back to the open position or to a partially open position. In this regard, positive pressure as may be used to facilitate the movement of the diaphragm 144 to its open position may be provided by air which is exhaled from the patient during the expiratory phase of the breathing circuit and is applied to the body portion 166 of the diaphragm 144 via the pillows portions 124 of the cushion 114, the fluid chamber 122, the exhaust vents 152, and the exhaust section 174 of the valve chamber. As will be recognized, the movement of the diaphragm 144 to the open position allows the air exhaled from the patient into the fluid chamber 122 via the pillow portions 124 to be vented to ambient air after flowing from the fluid chamber 122 into the exhaust section 174 of the valve chamber via the exhaust vents 152, and thereafter flowing from the exhaust section 174 between the diaphragm 144 and seating surface 149 of the wall portion 146 into the outlet conduit 147 also defined by the wall portion 146.

As will be recognized, based on the application of pilot pressure thereto, the diaphragm 144 travels from a fully open position through a partially open position to a fully closed position. In this regard, the diaphragm 144 will be partially open or partially closed during exhalation to maintain desired ventilation therapy. Further, when pilot pressure is discontinued to the diaphragm 144, it moves to an open position wherein the patient can inhale and exhale through the mask 110 with minimal restriction and with minimal carbon dioxide retention therein. This is an important feature of the present invention which allows a patient to wear the mask 110 without ventilation therapy being applied to the mask 110, the aforementioned structural and functional features of the mask 110 making it more comfortable to wear, and further allowing it to be worn without carbon dioxide buildup. This feature is highly advantageous for the treatment of obstructive sleep apnea wherein patients complain of discomfort with ventilation therapy due to mask and pressure discomfort. When it is detected that a patient requires sleep apnea therapy, the ventilation therapy can be started (i.e., in an obstructive sleep apnea situation).

To succinctly summarize the foregoing description of the structural and functional features of the mask 110, during patient inhalation, the valve pilot lumen 138 is pressurized, which causes the diaphragm 144 to close against the seating surface 149, thus effectively isolating the fluid chamber 122 of the mask 110 from the outside ambient air. The entire flow delivered from a flow generator fluidly coupled to the mask 110 is inhaled by the patient, assuming that unintentional leaks at the interface between the cushion 114 and the patient are discarded. This functionality differs from what typically occurs in a conventional CPAP mask, where venting to ambient air is constantly open, and an intentional leak flow is continuously expelled to ambient air. During patient exhalation, the pilot pressure introduced into the valve pilot lumen 138 is controlled so that the exhaled flow from the patient can be exhausted to ambient air through the exhalation valve 112 in the aforementioned manner. In this regard, the pilot pressure is "servoed" so that the position of the diaphragm 144 relative to the seating surface 149 is modulated, hence modulating the resistance of the exhalation valve 112 to the exhaled flow and effectively ensuring that the pressure in the fluid chamber 122 of the mask 110 is maintained at a prescribed therapeutic level throughout the entire length of the exhalation phase. When the valve pilot lumen 138 is not pressurized, the exhalation valve 112 is in a normally open state, with the diaphragm 144 being spaced from the seating surface 149 in the aforementioned manner, thus allowing the patient to spontaneously breathe in and out with minimal pressure drop (also referred to as back-pressure) in the order of less than about 2 cm H2O at 60 l/min. As a result, the patient can comfortably breathe while wearing the mask 110 and while therapy is not being administered to the patient. Importantly, the effective containment of the exhaust vents 152 within the fluid chamber 122 substantially mitigates or suppresses the noise generated by the mask 110 attributable to the flow of fluid into the exhaust section 174 of the valve chamber via the exhaust vents 152.

Those of ordinary skill in the art will recognize that the functionality of the exhalation valve 112 during use of the mask 110 by a patient can be characterized with the same three parameters described above in relation to the mask 10 and shown in FIGS. 11A, 11B and 11C. However, based on the structural features of the exhalation valve 112 in comparison to the exhalation valve 12, the parameters Pt which is the treatment pressure (i.e., the pressure in the mask 110 used to treat the patient; Pp which is the pilot pressure (i.e., the pressure used to pilot the diaphragm 144 in the exhalation valve 112); and Qv which is vented flow (i.e., flow that is exhausted from inside the exhalation valve 112 to ambient are labeled in FIG. 18 as Pt, Pp and Qv in the context of the exhalation valve 112. As such, when the patient is ventilated, Pt is greater than zero, with the functionality of the exhalation valve 112 being described by the family of curves in the first and second quadrants of FIG. 11A. In this regard, as apparent from FIG. 11A, for any given Pt, it is evident that by increasing the pilot pressure Pp, the exhalation valve 112 will close and the vented flow will decrease. A decrease in the pilot pressure Pp will facilitate the opening of the exhalation valve 112, thereby increasing vented flow. The vented flow will increase until the diaphragm 144 touches or contacts the inner surface 156 of the base portion 154 of the cap member 142, and is thus not able to open further. Conversely, when the patient is not ventilated, the inspiratory phase can be described by the third and fourth quadrants. More particularly, Qv is negative and air enters the mask 110 through the exhalation valve 112, with the pressure Pt in the mask 110 being less than or equal to zero. Pilot pressure Pp less than zero is not a configuration normally used during ventilation of the patient, but is depicted for a complete description of the functionality of the exhalation valve 112. The family of curves shown in FIG. 11A can be described by a parametric equation. Further, the slope and asymptotes of the curves shown in FIG. 11A can be modified by, for example and not by way of limitation, changing the material used to fabricate the diaphragm 144, changing the thickness of the diaphragm 144, changing the area ratio between the side of the diaphragm 144 facing the pilot section 172 and the side facing the exhaust section 174, changing the clearance between the diaphragm 144 and the seating surface 149, and/or changing the geometry of the exhaust vents 152.

As also discussed above in relation to the mask 10, an alternative representation of the functional characteristics of the valve 112 can be described by graphs in which $\Delta P = Pt - Pp$ is shown. For example, the graph of FIG. 11B shows that for any given Pt, the vented flow can be modulated by changing $\Delta P$. In this regard, $\Delta P$ can be interpreted as the physical position of the diaphragm 144. Since the diaphragm 144 acts like a spring, the equation describing the relative position d of the diaphragm 144 from the seating surface 149 of the seat member 140 is $k \cdot d + Pt \cdot At = Pp \cdot Ap$, where At is the area of the diaphragm 144 exposed to treatment pressure Pt and Ap is the area of the diaphragm 144 exposed to the pilot pressure Pp. A similar, alternative representation is provided in the graph of FIG. 11C which shows Pt on the x-axis and $\Delta P$ as the parameter. In this regard, for any given $\Delta P$, the position d of the diaphragm 144 is determined, with the exhalation valve 112 thus being considered as a fixed opening valve. In this scenario Pt can be considered the driving pressure pushing air out of the exhalation valve 112, with FIG. 11C further illustrating the highly non-linear behavior of the valve 112.

The mask 110 may also be integrated into each of the above-described ventilation systems 88, 100 in substitution for the mask 10. In this regard, as will be recognized by those of ordinary skill in the art, the first and second bi-lumen tubes 96, 98 of such ventilation systems 88, 100 would simply be cooperatively engaged to corresponding ones of the first and second connectors 180, 182, pressure port 184 and pilot port 186 of the frame member 178 in the same manner described above regarding the engagement to the first and second connectors 80, 82, pressure port 84 and pilot port 86 of the frame member 78.

In the mask 110, it is contemplated that exhalation vale subassembly 111, and in particular the exhalation valve 112, may be detached from the cushion 114 and removed from within the fluid chamber 122 as needed for periodic cleaning or replacement thereof. As will be recognized, such removal is facilitated by first detaching the shield plate 113 from the cushion 114 by removing the lip of the cushion 114 defining the valve opening 126 from within the channel 176 of the shield plate 113. Thereafter, the exhalation valve 112 is simply grasped and pulled from within the fluid chamber 122, the flexibility/resiliency of the cushion 114 allowing for the easy removal of the tube portions 162 of the cap member 142 from within respective ones of the pilot lumen 138 and mounting aperture 139. The re-attachment of the exhalation valve subassembly 111 to the cushion 114 occurs in the reverse sequence, the exhalation valve 112 being advanced into the fluid chamber 122 and attached to the cushion 114 in the aforementioned manner prior to the attachment of the shield plate 113 to the cushion 114 in the aforementioned manner.

Figure 27:
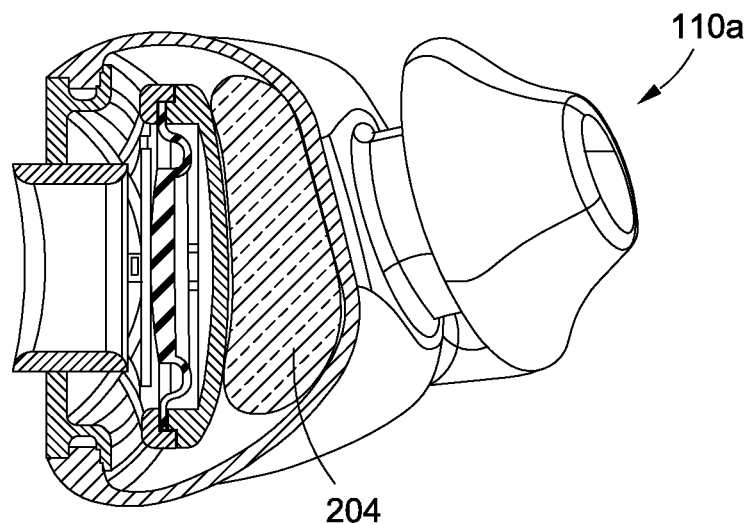
FIG. 27 is a cross-sectional view similar to FIG. 19, but depicting a variant of the nasal pillows mask shown in FIG. 15 wherein an HME is integrated into the cushion thereof.
Figure 28:
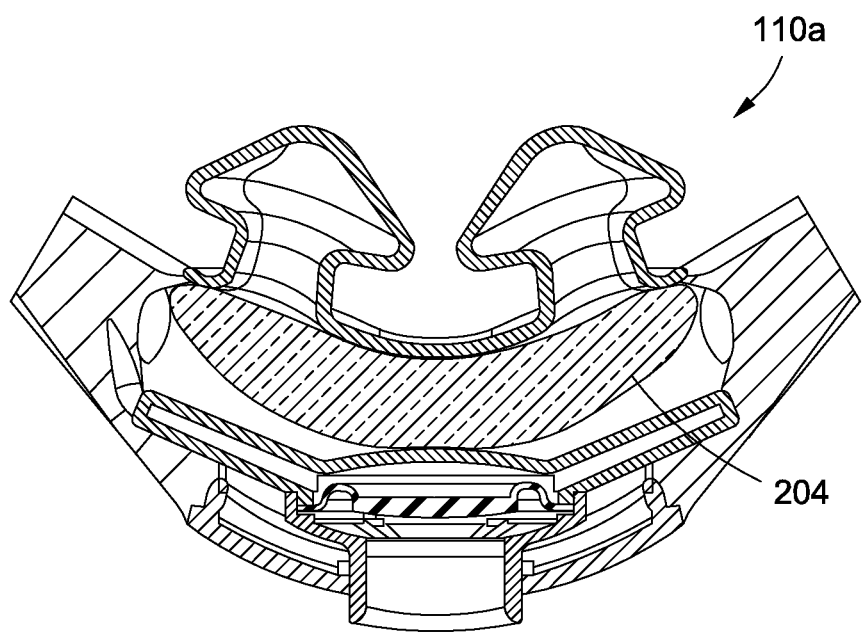
FIG. 28 is a cross-sectional view similar to FIGS. 17 and 18, but depicting a variant of the nasal pillows mask shown in FIG. 15 wherein an HME is integrated into the cushion thereof.

Referring now to FIGS. 27 and 28, there is shown a mask 110a which comprises a variant of the mask 110. The sole distinction between the masks 110, 110a lies in the mask 110a including a heat and moisture exchanger or HME 204 which is positioned within the fluid chamber 122 of the cushion 114. The HME 204 is operative to partially or completely replace a humidifier (cold or heated pass-over; active or passive) which would otherwise be fluidly coupled to the mask 110a. This is possible because the average flow through the system envisioned to be used in conjunction with the mask 110a is about half of a prior art CPAP mask, due to the absence of any intentional leak in such system.

The HME 204, as a result of its positioning within the fluid chamber 122, is able to interact with the flow delivered from the flow generator to the patient in order to humidify it, and is further able to capture humidity and heat from exhaled flow for the next breath. The pressure drop created by the HME 204 during exhalation (back-pressure) must be limited, in the order of less than 5 cm H2O at 60 l/min, and preferably lower than 2 cm H2O at 60 l/min. These parameters allow for a low back-pressure when the patient is wearing the mask 110a and no therapy is delivered to the patient.

It is contemplated that the HME 204 can be permanently assembled to the cushion 114, or may alternatively be removable therefrom and thus washable and/or disposable. In this regard, the HME 204, if removable from within the cushion 114, could be replaced on a prescribed replacement cycle. As will be recognized, the removal of the HME 204 from within the fluid chamber 122 would follow the detachment of the exhalation valve subassembly 111 from the cushion 114 in the manner described above. Similarly, the placement of the HME 204 back into the fluid chamber 122 would precede the reattachment of the exhalation valve subassembly 111 to the cushion 114 in the manner also described above. Additionally, it is contemplated that the HME 204 can be used as an elastic member that adds elasticity to the cushion 114. In this regard, part of the elasticity of the cushion 114 may be attributable to its silicone construction, and further be partly attributable to the compression and deflection of the HME 204 inside the cushion 114.

The integration of the exhalation valve 12, 112 into the cushion 14, 114 and in accordance with the present invention allows lower average flow compared to prior art CPAP masks. As indicated above, normal masks have a set of apertures called "vents" that create a continuous intentional leak during therapy. This intentional leak or vented flow is used to flush out the exhaled carbon dioxide that in conventional CPAP machines, with a standard ISO taper tube connecting the mask to the flow generator or blower, fills the tubing up almost completely with carbon dioxide during exhalation. The carbon dioxide accumulated in the tubing, if not flushed out through the vent flow, would be inhaled by the patient in the next breath, progressively increasing the carbon dioxide content in the inhaled gas at every breath. The structural/functional features of the exhalation valve 12, 112, in conjunction with the use of small inner diameter, high pneumatic resistance tubes in the system in which the mask 10, 10a, 110, 110a is used, ensures that all the exhaled gas goes to ambient. As a result, a vent flow is not needed for flushing any trapped carbon dioxide out of the system. Further, during inspiration the exhalation valve 12, 112 can close, and the flow generator of the system needs to deliver only the patient flow, without the additional overhead of the intentional leak flow. In turn, the need for lower flow rates allows for the use of smaller tubes that have higher pneumatic resistance, without the need for the use of extremely powerful flow generators. The pneumatic power through the system can be kept comparable to those of traditional CPAP machines, though the pressure delivered by the flow generator will be higher and the flow lower.

The reduced average flow through the system in which the mask 10, 10a, 110, 110a is used means that less humidity will be removed from the system, as well as the patient. Conventional CPAP systems have to reintegrate the humidity vented by the intentional leak using a humidifier, with heated humidifiers being the industry standard. Active humidification introduces additional problems such as rain-out in the system tubing, which in turn requires heated tubes, and thus introducing more complexity and cost into the system. The envisioned system of the present invention, as not having any intentional leak flow, does not need to introduce additional humidity into the system. As indicated above, the HME 104, 204 can be introduced into the cushion 14, 114 of the mask 10a, 110a so that exhaled humidity can be trapped and used to humidify the air for the following breath.

In addition, a big portion of the noise of conventional CPAP systems is noise conducted from the flow generator through the tubing up to the mask and then radiated in the ambient through the vent openings. As previously explained, the system described above is closed to the ambient during inhalation which is the noisiest part of the therapy. The exhaled flow is also lower than the prior art so it can be diffused more efficiently, thus effectively decreasing the average exit speed and minimizing impingement noise of the exhaled flow on bed sheets, pillows, etc.

As also explained above, a patient can breathe spontaneously when the mask 10, 10a, 110, 100a is worn and not connected to the flow generator tubing, or when therapy is not administered. In this regard, there will be little back pressure and virtually no carbon dioxide re-breathing, due to the presence of the exhalation valve 12, 112 that is normally open and the inner diameters of the tubes integrated into the system. This enables a zero pressure start wherein the patient falls asleep wearing the mask 10, 10a, 110, 110a wherein the flow generator does not deliver any therapy. Prior art systems can only ramp from about 4 m H2O up to therapy pressure. A zero pressure start is more comfortable to patients that do not tolerate pressure.

Figure 14:
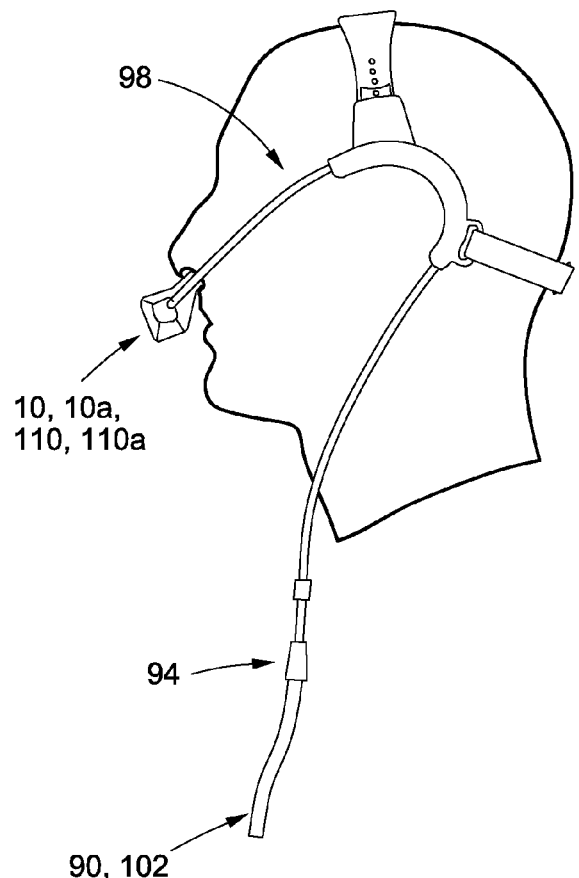
FIG. 14 is a side-elevational view of any nasal pillows mask constructed in accordance with the present invention as cooperatively engagement in an exemplary manner to a patient through the use of a headgear assembly.

As seen in FIG. 14, due to the reduced diameter of the various tubes (i.e., the tri-lumen tube 90 and bi-lumen tubes 96, 98, 102) integrated into the system 88, 100, such tubes can be routed around the patient's ears similar to conventional O2 cannulas. More particularly, the tubing can go around the patient's ears to hold the mask 10, 10a, 110, 110a to the patient's face. This removes the "tube drag" problem described above since the tubes will not pull the mask 10, 10a away from the face of the patient when he or she moves. As previously explained, "tube drag" typically decreases mask stability on the patient and increases unintentional leak that annoys the patient. In the prior art, head gear tension is used to counter balance the tube drag, which leads to comfort issues. The tube routing of the present invention allows for lower head gear tension and a more comfortable therapy, especially for compliant patients that wear the mask 10, 10a, 110, 110a approximately eight hours every night. The reduction in tube drag in accordance with the present invention also allows for minimal headgear design (virtually none), reduced headgear tension for better patient comfort as indicated above, and reduced cushion compliance that results in a smaller, more discrete cushion 14, 114. The tube dangling in front of the patient, also commonly referred to as the "elephant trunk" by patients, is a substantial psychological barrier to getting used to therapy. The tube routing shown in FIG. 14, in addition to making the mask 10, 10a, 110, 110a more stable upon the patient, avoids this barrier as well. Another benefit to the smaller tubing is that the mask 10, 10a, 110, 110a can become smaller because it does not need to interface with large tubing. Indeed, large masks are another significant factor leading to the high non-compliance rate for CPAP therapy since, in addition to being non-discrete, they often cause claustrophobia.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A ventilation mask, comprising:
   a housing sized and configured to be positionable between a patient's nose and mouth in contact with the patient's nose, the housing defining an internal fluid chamber, at least one gas delivery lumen which fluidly communicates with the fluid chamber, and a valve pilot lumen; and
   a piloted exhalation valve attached to the housing and at least partially residing within the fluid chamber thereof, the exhalation valve comprising:
   a valve housing defining a valve chamber which fluidly communicates with the fluid chamber, the pilot lumen and ambient air; and
   a diaphragm disposed within the valve chamber, the diaphragm normally being biased to an open position wherein the fluid chamber fluidly communicates with ambient air via the valve chamber, and a closed position wherein fluid communication between the fluid chamber and ambient air is blocked thereby, the movement of the diaphragm from the open position to the closed position being facilitated by the selective pressurization of at least a portion of the valve chamber via the pilot lumen.

2. The ventilation mask of claim 1 wherein the housing further defines a pressure sensing lumen which fluidly communicates with the fluid chamber.

3. The ventilation mask of claim 1 wherein the housing is a resilient cushion including a spaced pair of hollow pillow portions which each fluidly communicate with the fluid chamber and are adapted to engage respective ones of the nostrils of the patient's nose.

4. The ventilation mask of claim 3 further comprising a heat and moisture exchanger disposed within the fluid chamber between the exhalation valve and the pillow portions of the cushion.

5. The ventilation mask of claim 3 wherein the valve housing comprises:
   a seat member; and
   a cap member attached to the seat member, the seat and cap members collectively defining the valve chamber;
   the diaphragm being captured between the seat and cap members in a manner wherein the diaphragm effectively segregates the valve chamber into a pilot section which fluidly communicates with the pilot lumen and an exhaust section which fluidly communicates with the fluid chamber in ambient air.

6. The ventilation mask of claim 5 wherein the diaphragm and the seat member define complimentary seating surfaces which are sized and configured relative to each other such that the movement of the diaphragm to the closed position facilitates the placement of the seating surfaces into sealed engagement with each other in a manner blocking fluid communication between the fluid chamber and ambient air.

7. The ventilation mask of claim 6 wherein the seat member includes a plurality of vents which are disposed therein and collectively define a fluid conduit between the fluid chamber and the exhaust section of the valve chamber.

8. The ventilation mask of claim 7 wherein the vents of the seat member reside within the fluid chamber of the cushion.

9. The ventilation mask of claim 8 further comprising a shield plate attached to the cushion and partially defining the fluid chamber, the shield plate including an opening therein which is sized and configured to accommodate a portion of the seat member.

10. The ventilation mask of claim 9 further comprising a reinforcement frame member which is attached to the cushion, the frame member spanning the shield plate and including an opening therein which is coaxially aligned with the opening of the shield plate and is size and configured to accommodate a portion of the seat member.

11. A ventilation mask, comprising:
    a housing sized and configured to be positionable between a patient's nose and mouth in contact with the patient's nose, the housing defining an internal fluid chamber; and
    an exhalation valve attached to the housing and at least partially residing within the fluid chamber thereof, the exhalation valve comprising:
    a valve housing defining a valve chamber which fluidly communicates with the fluid chamber via at least one vent and with ambient air via at least one outlet conduit; and
    a diaphragm disposed within the valve chamber, the diaphragm being selectively movable between an open position wherein the fluid chamber fluidly communicates with ambient air via the valve chamber, and a closed position wherein fluid communication between the fluid chamber and ambient air is blocked thereby;
    the vent of the valve housing residing and being enclosed within the fluid chamber, with the outlet conduit of the valve housing protruding from the fluid chamber.

12. The ventilation mask of claim 11 wherein the housing is a resilient cushion including a spaced pair of hollow pillow portions which each fluidly communicate with the fluid chamber and are adapted to engage respective ones of the nostrils of a patient's nose.

13. The ventilation mask of claim 12 further comprising a heat and moisture exchanger disposed within the fluid chamber between the exhalation valve and the pillow portions of the cushion.

14. The ventilation mask of claim 12 wherein the valve housing comprises:

a seat member defining the vent and the outlet conduit; and a cap member attached to the seat member, the seat and cap members collectively defining the valve chamber;

the diaphragm being captured between the seat and cap members in a manner wherein the diaphragm effectively segregates the valve chamber into at least two sections, one of which fluidly communicates with the vent and the outlet conduit.

15. The ventilation mask of claim 14 wherein the diaphragm and the seat member define complimentary seating surfaces and are sized and configured relative to each other such that the movement of the diaphragm to the closed position facilitates the placement of the seating surfaces into sealed engagement with each other in a manner blocking fluid communication between the vent and the outlet conduit.

16. The ventilation mask of claim 15 wherein the seat member includes a plurality of vents which collectively define a fluid conduit.

17. The ventilation mask of claim 15 further comprising a shield plate attached to the cushion and partially defining the fluid chamber, the shield plate including an opening therein which is sized and configured to accommodate a portion of the seat member which defines the outlet conduit thereof.

18. The ventilation mask of claim 17 further comprising a reinforcement frame member which is attached to the cushion, the frame member spanning the shield plate and including an opening therein which is coaxially aligned with the opening of the shield plate and is sized and configured to accommodate the portion of the seat member which defines the outlet conduit thereof.

19. A ventilation mask, comprising:

a housing sized and configured to be positionable between a patient's nose and mouth in contact with the patient's nose, the housing defining an internal fluid chamber, at least one gas delivery lumen which fluidly communicates with the fluid chamber, and a valve pilot lumen; and an exhalation valve at least partially residing within the fluid chamber of the housing, the exhalation valve including:

a valve chamber which fluidly communicates with the fluid chamber, the pilot lumen and ambient air; and a diaphragm which is disposed within the valve chamber, the diaphragm being movable between an open position wherein the fluid chamber fluidly communicates with ambient air via the valve chamber, and a closed position wherein fluid communication between the fluid chamber and ambient air is blocked thereby;

the movement of the diaphragm from the open position to the closed position being facilitated by the selective pressurization of at least a portion of the valve chamber via the pilot lumen.

20. The ventilation mask of claim 19 wherein the housing further defines a pressure sensing lumen which fluidly communicates with the fluid chamber.

* * * * *